(12) United States Patent
Reich et al.

(10) Patent No.: US 10,697,958 B2
(45) Date of Patent: *Jun. 30, 2020

(54) UNMASKING ENDOTOXINS IN SOLUTION

(71) Applicant: HYGLOS INVEST GMBH, Bernried (DE)

(72) Inventors: Johannes Reich, Weilheim (DE);
Holger Grallert, Weilheim (DE)

(73) Assignee: HYGLOS INVEST GMBH, Bernried (DE)

( * ) Notice: Subject to any disclaimer, the term of this patent is extended or adjusted under 35 U.S.C. 154(b) by 239 days.

This patent is subject to a terminal disclaimer.

(21) Appl. No.: 15/318,086

(22) PCT Filed: Jun. 12, 2015

(86) PCT No.: PCT/EP2015/063154
§ 371 (c)(1),
(2) Date: Dec. 12, 2016

(87) PCT Pub. No.: WO2015/189379
PCT Pub. Date: Dec. 17, 2015

(65) Prior Publication Data
US 2017/0131265 A1    May 11, 2017

Related U.S. Application Data

(60) Provisional application No. 62/011,818, filed on Jun. 13, 2014.

(30) Foreign Application Priority Data

Jun. 12, 2014 (EP) ..................................... 14172151

(51) Int. Cl.
*G01N 33/53* (2006.01)
*G01N 33/92* (2006.01)
*G01N 33/50* (2006.01)

(52) U.S. Cl.
CPC ......... *G01N 33/5306* (2013.01); *G01N 33/50* (2013.01); *G01N 33/92* (2013.01); *G01N 2400/50* (2013.01)

(58) Field of Classification Search
CPC .... G01N 33/92; G01N 33/50; G01N 33/5306; G01N 2400/50
See application file for complete search history.

(56) References Cited

U.S. PATENT DOCUMENTS

| 4,276,050 A | 6/1981 | Firca et al. |
| 4,909,940 A | 3/1990 | Horowitz et al. |
| 5,962,428 A | 10/1999 | Carrano et al. |
| 7,750,199 B1* | 7/2010 | Tucker .................. A61K 31/14 588/320 |
| 8,399,633 B2* | 3/2013 | Ropp .................. B01D 15/362 435/961 |

| 2003/0194412 A1 | 10/2003 | Baker et al. |
| 2005/0282202 A1 | 12/2005 | Brolaski et al. |
| 2009/0275097 A1 | 11/2009 | Sun et al. |
| 2010/0028857 A1 | 2/2010 | Schutz et al. |
| 2011/0003976 A1 | 1/2011 | Ropp et al. |
| 2011/0053188 A1 | 3/2011 | Meyer et al. |
| 2011/0319341 A1 | 12/2011 | Awada et al. |
| 2013/0331466 A1 | 12/2013 | Gross et al. |

FOREIGN PATENT DOCUMENTS

| EP | 0308239 | 3/1989 |
| EP | 0 322 786 | 7/1989 |
| EP | 1917976 | 5/2008 |
| GB | 425216 | 3/1935 |
| JP | H01-156910 | 6/1989 |
| JP | H01-294629 | 11/1989 |
| JP | H07-255462 | 10/1995 |
| JP | 2005-530991 | 10/2005 |
| JP | 2006-194606 | 7/2006 |
| JP | 2008-514771 | 5/2008 |
| JP | 2009-155613 | 7/2009 |
| WO | WO 2002/057789 | 7/2002 |
| WO | WO 2006/129662 | 5/2006 |
| WO | WO 2009/152384 | 12/2009 |

OTHER PUBLICATIONS

English translation of Office Communication issued in Japanese Patent Application No. 2016-572422, dated Dec. 6, 2017.
Office Communication issued in Australian Patent Application No. 2015273432, dated Jan. 15, 2018.
Reich et al., "Low Endotoxin recovery in Bio-Pharmaceuticals: Comparison of Naturally Occurring Endotoxins (NOE) and Commercial Standards," Poster, PDA Annual Meeting, San Antonio, USA, Apr. 7-10, 2014.
Reich et al., "Low endotoxin recovery in common protein formulations," PDA, 6th workshop on Monoclonal Antibodies, Poster, Basel, Switzerland, Sep. 11-12, 2013.
Reich, "Reliability of Endotoxin-Detection: Mechanistical Principles of Endotoxin-Masking and Strategies for De-Masking," Presentation, PDA Pharmaceutical Microbiology, Berlin, Germany, Feb. 18-19, 2014.
Williams, "Low endotoxin recovery (LER) in drug products", PDA Letter, p. 26-27, Jul./Aug. 2013.
Hyglos, "Introduction: Endotoxin Detection Technology," FDA presentation, Silver Spring, Maryland, presented Jun. 19, 2014.
Hyglos, "Package Insert EndoLisa," 2013.
Jürgens et al.: "Investigation into the interaction of recombinant human serum albumin with re-lipopolysacchardie and lipid A," *Journal of Endotoxin Research*, 8:115-126, 2002.
Mutter, "Masking and De-masking of endotoxin in biopharmaceutical formulations," BIO International Convention presentation, San Diego, presented on Jun. 23-26, 2014.

(Continued)

*Primary Examiner* — Shafiqul Haq
(74) *Attorney, Agent, or Firm* — Parker Highlander PLLC

(57) ABSTRACT

The invention relates to unmasking endotoxins in compositions so that previously present, but undetectable endotoxins are rendered detectable.

12 Claims, 15 Drawing Sheets

(56) References Cited

OTHER PUBLICATIONS

Ohno et al., "Lipopolysaccharide interaction with lysozyme," *Journal of Biological Chemistry*, 264(8):4434-4441, Mar. 15, 1989.
Petsch et al., "Proteinase K digestion of proteins improves detection of bacterial endotoxins by the Limulus Amebocyte Lysate Assay: Application for endotoxin removal from cationic proteins," *Analytical Biochemistry* 258:42-47, 1998.
Reich et al., "Low Endotoxin recovery in Bio-Pharmaceuticals: Comparison of Naturally Occurring Endotoxins (NOE) and Commercial Standards," Poster, PDA Annual Meeting, 7-10, San Antonio, USA, Apr. 2014.
Reich et al., "Low endotoxin recovery in common protein formulations," PDA, 6th workshop on Monoclonal Antibodies, Poster, 11-12, Basel, Switzerland, Sep. 2013.
Reich, "Endotoxin masking and de-masking," FDA Presentation, non-public, Jun. 19, 2014.
Reich, "Reliability of Endotoxin-Detection: Mechanistical Principles of Endotoxin-Masking and Strategies for De-Masking," Presentation, PDA Pharmaceutical Microbiology, 18-19, Berlin, Germany, Feb. 2014.
Stauffer, "LER concerns create debate between industry, regulators", PDA Letter L(1), Jan. 2014.
Williams, "Endotoxin test concerns of biologics part II: Developing new tools," *Review of American Pharmaceutical Business & Technology*, Mar. 31, 2014.
Williams, "Endotoxin test concerns of biologics," *Review of American Pharmaceutical Business & Technology*, Oct. 28, 2013.
Williams, "Low endotoxin recovery (LER) in drug products", PDA Letter, Jul./Aug. 26-27, 2013.
Office Communication issued in Japanese Patent Application No. 2016-572419, dated Jan. 17, 2017. (English translation of Japanese text).
Office Communication issued in European Patent Application No. 14172151.4, dated Jan. 22, 2018.
Office Communication issued in Australian Patent Application No. 2015273431, dated Oct. 10, 2017.
Bauduin et al., "The influence of structure and composition of a revere SDS microemulsion on enzymatic activities and electrical conductivities," *Journal of Colloid and Interface Science*, 292(2):244-254, 2005.
English translation of Office Communication issued in Japanese Patent Application No. 2018-216248, dated Aug. 28, 2019.
Extended European Search Report issued in European Patent Application No. 19164891.4, dated Apr. 26, 2019.
Extended European Search Report issued in European Patent Application No. 18210611.2, dated Jan. 9, 2019.
Merino et al., "Enhancement of nortriptyline penetration through chemical enhancers and iontophoresis," *Journal of Pharmacy and Pharmacology*, 60(4):415-420, 2008.
English translation of Office Communication issued in Chinese Patent Application No. 201580043199.9, dated Nov. 27, 2018.
Office Communication issued in U.S. Appl. No. 15/316,884, dated Jun. 19, 2018.
Office Communication issued in U.S. Appl. No. 15/316,884, dated Dec. 4, 2018.
"Fatty alcohol," *Wikipedia*, Wikipedia Foundation, Mar. 24, 2014, https://en.wikipedia.org/w/index.php?title+Fatty_alcohol&oldid=601090872.
"Lipid," *Wikipedia*, Wikipedia Foundation, Jan. 20, 2020, https://en.wikipedia.org/w/index.php?title=Lipid&oldid=936653209.
Franken et al., "Purification of His-tagged proteins by immobilized chelate affinity chromatography: The benefits from the use of organic solvent," *Protein Expression and Purification*, 18:95-99, 2000.
IUPAC. Compendium D. of Chemical Terminology, $2^{nd}$ ed. (the "Gold Book"). Compiled by A. D. McNaught and A. Wilkinson. Blackwell Scientific Publications, Oxford (1997). Online version (2019-) created by S. J. Chalk. ISBN 0-9678550-9-8. https://doi.org/10.1351/goldbook.
Jager et al., "Sodium dodecyl sulfate," *Encyclopedia of Reagents for Organic Synthesis*, pp. 1-2, 2001.
Notice of Opposition issued in European patent application No. 14172151.4, dated Feb. 19, 2020.
Notice of Opposition issued in European patent application No. 15727685.8, dated Feb. 5, 2020.
Yu and Wright, "Catalytic Properties of Lipopolysaccharide (LPS) Binding Protein," *The Journal of Biological Chemistry*, 271(8):4100-4105, 1996.

\* cited by examiner

Step 1

| Unmasking approach | Chaotropic salt [CaCl2] (M) | Adsorbing modulator [BSA] (mg/ml) | Displacing modulator [SDS] (%) | Reconfiguring modulator [1-Dodecanol] (mM) |
|---|---|---|---|---|
| A | - | - | - | 100 |
| A | - | - | - | 10 |
| A | - | - | - | 1 |
| B | - | 100 | - | 100 |
| B | - | 100 | - | 10 |
| B | - | 100 | - | 1 |
| C | 1 | 100 | 1 | 100 |
| C | 1 | 100 | 1 | 10 |
| C | 1 | 100 | 1 | 1 |

Step 2

| Unmasking approach | Adsorbing modulator [BSA] (mg/ml) |
|---|---|
| B or C | 100 |
| B or C | 10 |
| B or C | 1 |

Step 3

| Unmasking approach | Displacing modulator [SDS] (%) |
|---|---|
| C | 1 |
| C | 0.1 |
| C | 0.01 |

Step 4

| Unmasking approach | H-bonding influencer [CaCl2] (mM) |
|---|---|
| C | 1000 |
| C | 100 |
| C | 10 |

UNMASKING ENDOTOXINS IN SOLUTION

This application is a national phase application under 35 U.S.C. § 371 of International Application No. PCT/EP2015/063154, filed Jun. 12, 2015, which claims the benefit of U.S. Provisional Patent Application No. 62/011,818, filed Jun. 13, 2014, and claims the benefit of European Patent Application No. 14172151.4, filed Jun. 12, 2014. The entirety of each of the above-referenced disclosures are incorporated herein by reference.

The present invention relates to unmasking endotoxins in compositions, preferably pharmaceutical compositions, so that present but undetectable endotoxins are rendered detectable. Specifically, the invention relates to a method of unmasking an endotoxin in a composition. The invention further relates to a method of detecting an endotoxin in a composition. The invention further relates to a kit for unmasking an endotoxin in a composition. The invention further relates to the use of a modulator capable of unmasking an endotoxin, e.g. by releasing an endotoxin from a complex between said endotoxin and an endotoxin masker, to unmask an endotoxin in a composition.

BACKGROUND OF THE INVENTION

Endotoxins are part of the outer membrane of the cell wall of Gram-negative bacteria. Endotoxin is invariably associated with Gram-negative bacteria regardless of whether the organisms are pathogenic or not. Although the term "endotoxin" is occasionally used to refer to any cell-associated bacterial toxin, in bacteriology it is properly reserved to refer to the lipopolysaccharide (LPS) complex associated with the outer membrane of Gram-negative pathogens such as *Escherichia coli, Salmonella, Shigella, Pseudomonas, Neisseria, Haemophilus influenzae, Bordetella pertussis* and *Vibrio cholerae*.

The presence of endotoxins in aqueous compositions is an intractable problem which severely threatens and/or limits the application of many compositions, in particular if intended for pharmaceutical use. This is especially true of compositions comprising protein products, e.g. recombinant protein products. Naturally occurring endotoxins, especially endotoxins belonging to the class of compounds characterized as lipopolysaccharides (LPS) are molecules produced by certain types of bacteria, for example gram-negative bacteria. Generally, endotoxins such as LPS comprise an extended polysaccharide O-antigen, a core antigen polysaccharide including an outer core component and an inner core component, and a lipid A domain comprising aliphatic amides and aliphatic acid esters. Such endotoxins are found in the outer membrane of gram-negative bacteria, where they contribute to bacterial structural integrity by shielding the organism from chemical attack. Such endotoxins increase the negative charge of the cell membrane of these bacteria, and help to stabilize the overall membrane structure. Such endotoxins elicit strong responses from normal animal, e.g. human, immune systems because normal serum contains lipooligosaccharide (LOS) receptors which normally direct the cytotoxic effects of the immune system against invading bacterial pathogens bearing such endotoxins.

When present in the human blood in a form disassociated from their source bacteria, endotoxins such as LPS can cause endotoxemia which in severe cases can lead to septic shock. This reaction is due to the endotoxin lipid A component, which can cause uncontrolled activation of the mammalian immune system, in some instances producing inflammatory mediators such as toll-like receptor (TLR) 4, which is responsible for immune system cell activation.

Bacteria, as well as the endotoxins they produce, are also ubiquitous. For instance, endotoxin contaminants are known to exist in the pipes and hoses of water supply systems, including those of laboratories and facilities for preparing pharmaceutical formulations. The surfaces of containers such as fermentors and glassware used in the process of formulating pharmaceuticals are also commonly contaminated. In addition, as humans carry bacteria and therefore endotoxins on their bodies, so the staff of such facilities in which pharmaceuticals are formulated also represent a possible source of endotoxin contaminants.

Of course, in addition to the above, gram-negative bacteria themselves find wide use in the production of i.a. recombinant therapeutic proteins, so there is always a danger that endotoxin contamination of aqueous compositions, e.g. pharmaceutical formulations, containing such therapeutic proteins may also arise directly from such bacteria used in the production process.

To safeguard against potentially hazardous incorporation of endotoxin contaminants, whatever their source, measures must normally be taken to exclude endotoxin from all steps and products used in the production process of such proteins before such solutions may be administered for therapeutic purposes. In fact, the exclusion and/or removal and verifiable absence of all traces of (detectable) endotoxin are among the requirements which much must be met when seeking regulatory approval for any new therapeutic, in particular those containing products produced in bacteria, or which have come into contact with bacteria at any point in the production process (see e.g. EMEA, Q6B, Specifications: Test Procedures and Acceptance Criteria for Biotechnological/Biological Products; 2.1.4 Purity, Impurities and Contaminants; Contaminants; 4.1.3 Purity and impurities; 2) FDA, Q6B, Specifications: Test Procedures and Acceptance Criteria for Biotechnological/Biological Products; II.A.4. Purity, Impurities and Contaminants; IV.A.3. Purity and Impurities). For instance, all containers holding and/or transferring solutions intended for eventual administration must be rendered endotoxin-free prior to contact with the solution. A depyrogenation oven is used for this purpose, in which temperatures in excess of 200° C. are required to break down endotoxins. Based on primary packaging material as syringes or vials, a glass temperature of 250° C. and a holding time of 30 minutes is typical to achieve a reduction of endotoxin levels by a factor of 1000. Usually, liquids can not be depyrogenated by heat, therefore different methods are used, such as chromatography (e.g. anion exchange), phase extraction (e.g. Trition X-114), filtration (e.g. ultrafiltration).

One common assay for detecting the activity of endotoxin is the limulus amebocyte lysate (LAL) assay, which utilizes blood from the horseshoe crab. Very low levels of endotoxin can cause coagulation by the limulus lysate due to a powerful amplification through an enzyme cascade. However, due to the dwindling population of horseshoe crabs, efforts have been made to develop alternative, e.g. recombinant, Factor C assays for detecting the presence of endotoxin in solution. The most promising of such methods are enzyme-linked affinitysorbent assays, using a solid phase for endotoxin capturing and subsequent detection by recombinant version of a protein in the LAL assay, Factor C. The EndoLISA® kit is one such affinitysorbent assay.

However, even the best available tests for detecting the presence of pyrogens, such as endotoxin, in particular LPS, are often unable to detect LPS in solution. This implies the danger that solutions which are reasonably—in the absence of any detectable endotoxin—thought to be endotoxin-free in fact contain endotoxin which is simply masked so as to be rendered undetectable. Such solutions, e.g. pharmaceutical formulations will not be barred from regulatory approval (at least not due to containing endotoxin), because by all diagnostic appearances, these solutions are endotoxin-free, therefore fulfilling—or at least appearing to fulfill—this regulatory requirement. Clearly, however, administration of such ostensibly endotoxin-free solutions to subjects risks triggering the types of reactions mentioned above. In such instances, one may learn of the presence of masked endotoxin in such solutions too late, after subjects have already developed the types of adverse and potentially life-threatening reactions described above. In addition, from a hygenic standpoint, drug regulatory authorities place great value on positively knowing which substances are contained in pharmaceutical compositions and which are not. This ultimately comes down to the ability to reliably detect all components in a given composition, and one's ability to believe the results obtained in reference to both the presence and absence of all substances tested.

It should be noted that the terms "masking" and "unmasking", as pertain to endotoxins, have been used with various meanings in the literature. On the one hand, the literature uses the term "endotoxin unmasking" or "endotoxin demasking" to describe removal of endotoxin from certain solutions (e.g. protein solutions). In this case, a certain endotoxin content is detectable before and after using common procedures for endotoxin removal (e.g. chromatography). Where the available techniques are inadequate for complete removal of endotoxin from the particular sample, the endotoxin which cannot be removed is referred to as "masked" endotoxin; any endotoxin which can be removed by available techniques is referred to as "unmasked" or "demasked" endotoxin. According to this usage of the term, "masked" endotoxin thus denotes endotoxin which cannot be removed, and implies insufficient removal of (detectable) endotoxin.

On the other hand, the literature also uses the term "endotoxin masking" in the case of inadequate endotoxin detection. In this case, only a fractional amount or, in many cases, no endotoxin whatsoever can be detected, although endotoxin is present. According to this usage of the term, "masked" endotoxin thus denotes endotoxin which cannot be detected, or can only barely be detected, and implies insufficient endotoxin detection.

Inadequate detection of endotoxin can occur in various compositions. For example in protein solutions (Petsch et al., Analytical Biochemistry 259, 42-47, 1998), drug products (J. Chen and K. Williams, Follow-Up on Low Endotoxin Recovery in Biologics PDA Letter, October 2013), or even in common formulation components of drug products (J. Reich et al., Poster: Low Endotoxin Recovery in Common Protein Formulations, 6th Workshop on Monoclonal Antibodies, Basel, Switzerland, 2013; J. Reich et al., Poster: Low Endotoxin Recovery in Biologics: Case Study—Comparison of Natural Occurring Endotoxin (NOE) and Commercially Available Standard Endotoxin, PDA Annual meeting, San Antonio, USA, 2014).

EP 308 239 A2 relates to a method of reducing a bacterial endotoxin contaminant in a biologically useful macromolecule solution. This document mentions "unmasking" endotoxins. An important aspect of that document's disclosure is that the endotoxin, even when "masked", remains detectable. The experimenter thus knows that endotoxin, even when masked, is present because it can be detected. This is a different meaning of the term "masked" then used in the present invention. According to the invention, and as explained below, "masked" endotoxin is undetectable.

Similarly, US 2010/0028857 A1 relates to a method of detecting endotoxin, with subsequent removal of the same. This document does not address how to render previously undetectable endotoxin detectable.

Reich et al. (Poster: Low Endotoxin Recovery in Common Protein Formulations, 6th Workshop on Monoclonal Antibodies, Basel, Switzerland, 2013) describe the evaluation of time-dependent masking effects on solutions known to contain endotoxin. While this document mentions "de-masking approaches", no specific measures for unmasking endotoxin are disclosed.

Similarly, Reich and Grallert (Poster: Low Endotoxin Recovery in Biologics: Case Study—Comparison of Natural Occurring Endotoxin (NOE) and Commercially Available Standard Endotoxin, PDA Annual meeting, San Antonio, USA, 2014) investigate the mechanism of endotoxin masking in solutions known to contain endotoxin. While this poster states that "de-masking is possible", no measures for unmasking endotoxin are disclosed. In particular, this document mentions de-masking with "additives", however mentions nothing about a modulator which is capable of unmasking an endotoxin or any measures which should be employed to unmask endotoxin.

Finally, a presentation by Reich ("Reliability of endotoxin-detection: Mechanistic principles of endotoxin-masking and strategies for de-masking", PDA Pharmaceutical Microbiology, Berlin, Germany, 2014) investigates the mechanism of endotoxin masking in solutions known to contain endotoxin. While this presentation mentions "additives" in the context of "de-masking", it mentions nothing about a modulator which is capable of unmasking endotoxin, or any measures which should be employed to unmask endotoxin.

There thus exists a strong motivation to provide ways in which all endotoxin present in compositions, including endotoxin which is undetectable because it is being masked by certain other composition components, may be unmasked such that it is rendered detectable. Providing a way to unmask and/or detect hitherto undetectable endotoxin in a composition would greatly assist in promoting patient safety. It is an aim of the present invention to address such needs.

BRIEF SUMMARY OF THE INVENTION

Accordingly, one aspect the invention relates to a method of unmasking an endotoxin in a composition, preferably a pharmaceutical composition, comprising an endotoxin masker and suspected of comprising said endotoxin, said method comprising the step of adding to said composition a modulator capable unmasking said endotoxin, e.g. by of releasing said endotoxin, if present, from a complex between said endotoxin and said endotoxin masker. The pharmaceutical composition will in most cases be an aqueous composition.

In a further aspect, the present invention relates to a method of detecting an endotoxin in a composition, preferably a pharmaceutical composition, comprising an endotoxin masker and suspected of comprising said endotoxin, said method comprising the steps of adding to said composition a modulator capable of unmasking said endotoxin, e.g. by releasing said endotoxin, if present, from a complex between said endotoxin and said endotoxin masker; and detecting said endotoxin by means of a detection method. The pharmaceutical composition will in most cases be an aqueous composition.

In certain embodiments, the above methods of unmasking and/or detecting may further comprise the step of adding to said composition an agent which influences hydrogen bonding stability in solution. In certain embodiments, it is preferable to add said agent which influences hydrogen bonding stability in solution to said solution prior to the addition of said modulator.

In a further aspect, the present invention relates to a kit for unmasking an endotoxin in a composition, preferably a pharmaceutical composition, comprising an endotoxin masker and suspected of comprising said endotoxin, said kit comprising a) a modulator capable of unmasking said endotoxin, e.g. by releasing said endotoxin from a complex between said endotoxin and said endotoxin masker; and b) an agent which influences hydrogen bonding stability in solution; wherein components (a) and (b) are in same or different packages.

In a further aspect, the present invention relates to a use of a modulator capable of unmasking endotoxin, e.g. by releasing an endotoxin from a complex between said endotoxin and an endotoxin masker, to unmask an endotoxin in a composition, preferably a pharmaceutical composition suspected of comprising said endotoxin and said endotoxin masker.

Other embodiments of this invention will be readily apparent from the following disclosure.

BRIEF DESCRIPTION OF THE FIGURES

FIG. 1 schematically shows the effects of adding a single-component modulator which breaks up these micelles, liberating embedded endotoxin, while not forming new micelles of its own. Following breakup of the detergent micelles, the single-component modulator then serves as a chaperone to the liberated endotoxin, stabilizing it in solution. An equilibrium exists between individual and aggregated endotoxin moieties, and the detection of the endotoxin aggregate proceeds based on the aggregated form ("Aggregates are the biologically active units of endotoxins". Mueller, M., Lindner, B., Kusomoto, S., Fukase, K., Schromm, A. B. and Seydel, U. (2004) The Journal of Biological Chemistry, Vol. 279, No. 25, pp. 26307-26313. Endotoxin in the form shown in panel (a) is not susceptible to detection, whereas endotoxin in the form shown in panel (c) is detectable. The scenario depicted in FIG. 1 is discussed in further detail below.

FIG. 2 schematically shows the effects of adding a dual-component modulator comprising protein and non-protein components. This dual-component modulator is assumed to break apart the detergent micelle in which the endotoxin was previously inserted and masked. The non-protein component of the modulator transiently stabilizes the endotoxin outside of the detergent micelle, while the protein component of the modulator destabilizes the detergent micelle by binding i.a. molecules of detergent. The scenario depicted in FIG. 2 is discussed in further detail below.

FIG. 3 schematically shows the effects of adding a multiple-component modulator, as well as an agent influencing hydrogen bonding stability. Together, the multiple-component modulator and the agent influencing hydrogen bonding stability destabilize the detergent micelle initially masking the endotoxin, and promote endotoxin aggregation such that it is rendered detectable. The scenario depicted in FIG. 3 is discussed in further detail below.

FIG. 4 schematically shows the effects of adding a multiple-component modulator such that the previously masked endotoxin aggregates and is rendered detectable. The scenario depicted in FIG. 4 is discussed in further detail below.

FIG. 5 schematically shows the effects of adding an agent influencing hydrogen bonding stability as well as a multiple-component modulator including protein and non-protein components. Together, these destabilize the endotoxin in its complex with the masking protein, transiently stabilize endotoxin outside of the complex with the masking protein, and promote aggregation of the liberated endotoxin, rendering it detectable. The scenario depicted in FIG. 5 is discussed in further detail below.

FIG. 6 schematically shows the effects of adding an agent influencing hydrogen bonding stability as well as a multiple-component modulator including protein and non-protein components. Together, these destabilize the endotoxin in its complex with the masking protein and/or in the masking detergent micelle, transiently stabilize endotoxin outside of the complex with the masking protein and/or in the masking detergent micelle, and promote aggregation of the liberated endotoxin, rendering it detectable. The scenario depicted in FIG. 6 is discussed in further detail below.

GENERAL

Figure 1:
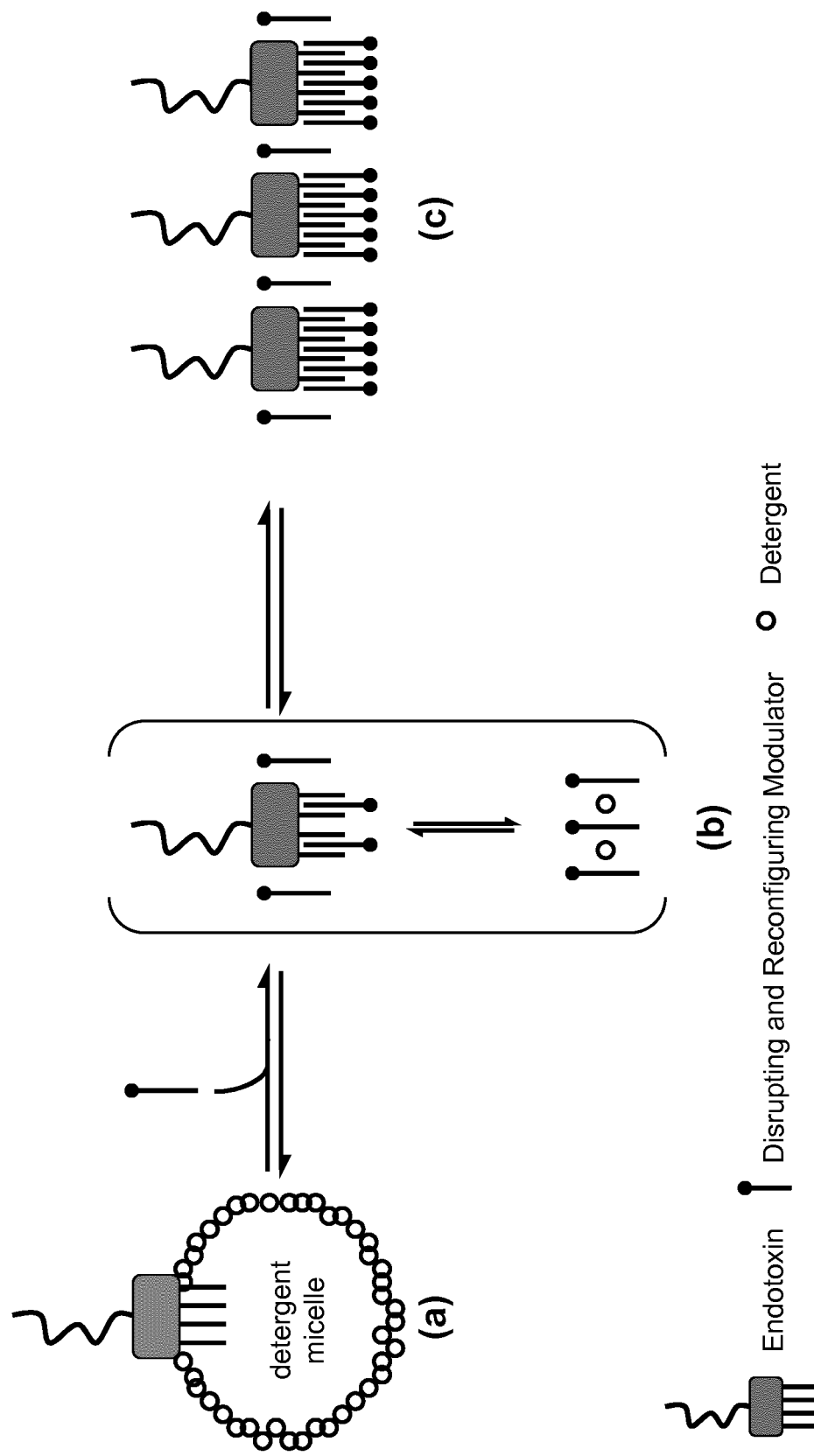
FIG. 1 illustrates a mechanism assumed to underlie the unmasking of endotoxin according to an embodiment of the present invention. In the scenario depicted in FIG. 1, the endotoxin is present in solution with a detergent (capable of acting as an endotoxin masker), which forms detergent micelles in which endotoxin is embedded and thus masked from detection.

It is to be understood that the foregoing general description as well as the following detailed description are exemplary and explanatory only and are not restrictive of the invention as claimed. In this application, the use of the singular includes the plural unless specifically stated otherwise. In this application, the use of "or" means "and/or" unless stated otherwise. Further, the use of the term "including" as well as other grammatical forms such as "includes" and "included", is not limiting. In the same sense, the use of the term "comprising" as well as other grammatical forms such as "comprises" and "comprised" is not limiting. Section headings throughout the description are for organizational purposes only. They are in particular not intended as limiting for the various embodiments described therein, and it is to be understood that elements and embodiments described under one subheading may be freely combined with elements and embodiments described under another subheading.

In the foregoing, subsequent description the claims, the features of any one embodiment are intended as being combinable with those of any other embodiment. Such combinations of one or more features in any one embodiment with one or more features in any other embodiment belong to the disclosure of the present application as filed.

All documents or portions of documents cited in this application, including but not limited to patents, patent applications, articles, monographs, books, treaties and regulations, are hereby expressly incorporated by reference in their entirety for any purpose.

DETAILED DESCRIPTION OF THE INVENTION

As mentioned above, one aspect of the invention relates to a method of unmasking an endotoxin in a composition, preferably a pharmaceutical composition, comprising an endotoxin masker and suspected of comprising said endotoxin, said method comprising the step of adding to said composition a modulator capable of unmasking said endotoxin, e.g. by releasing said endotoxin, if present, from a complex between said endotoxin and said endotoxin masker. The pharmaceutical composition will in most cases be an aqueous composition.

A further aspect of the invention relates to a method of detecting an endotoxin in a composition, preferably a pharmaceutical composition, comprising an endotoxin masker and suspected of comprising said endotoxin, said method comprising the steps of: adding to said composition a modulator capable of unmasking said endotoxin, e.g. by releasing said endotoxin, if present, from a complex between said endotoxin and said endotoxin masker; and detecting said endotoxin by means of a detection method. The pharmaceutical composition will in most cases be an aqueous composition.

Endotoxin

The term "endotoxin" refers to a molecule produced on the surface of bacteria in particular gram-negative bacteria, that is bacteria which, because of their thin peptidoglycan layer sandwiched between an inner cell membrane and a bacterial outer membrane, do not retain the crystal violet stain used in the Gram staining method of bacterial differentiation and therefore evade positive detection by this method. Specifically, endotoxins are biologically active substances present in the outer membrane of gram-negative bacteria. One common class of endotoxins is lipopolysaccharides (LPS). For the purposes of the present application, the terms "endotoxin" and "LPS" are used interchangeably. As is discussed elsewhere herein, however, it is understood that there exist different types of LPS, e.g. derived from different sources, and that the terms "endotoxin" and "LPS" are intended to encompass these different types of LPS. Endotoxins are located on the surface of bacteria and, together with proteins and phospholipids, form the outer bacterial membrane. Generally, LPS is made up of two parts with different chemical and physical properties; a hydrophilic sugar domain (the polysaccharide) and a hydrophobic lipid domain (lipid A). Two distinct regions can be recognized in the polysaccharide: the core oligosaccharide and the O-specific polysaccharide (M. A. Freudenberg, C. Galanos, Bacterial Lipopolysaccharides: Structure, Metabolism and Mechanisms of Action, Intern. Rev. Immunol. 6, 1990).

The lipid A is highly hydrophobic and is the endotoxically active part of the molecule. Lipid A is typically composed of a beta-D-GlcN-(1-6)-alpha-D-GlcN disaccharide carrying two phosphoryl groups. Up to four acyl chains are attached to this structure. These chains can then in turn be substituted by further fatty acids, which can vary quite considerably between species in their nature, number, length, order and saturation. Covalently attached to the lipid A is the core section of the molecule which can itself be formally divided into inner and outer core. The inner core is proximal to the lipid A and contains unusual sugars like 3-deoxy-D-manno-octulosonic acid (KDO). The outer core extends further from the bacterial surface and is more likely to consist of more common sugars such as hexoses and hexosamines. Onto this is attached, in most cases, a polymer of repeating saccharide subunits called the O-polysaccharide, also typically composed of common sugars. This O-polysaccharide is not ubiquitous, however, as it is seen to be truncated or lacking in a number of Gram-negative strains. In addition, certain strains carry mutations in the otherwise well-conserved locus and are termed "rough mutants" to differentiate them from the wild-type "smooth" strains which express O-polysaccharide bearing LPS (C. Erridge, E. Bennett-Guerrero, I. Poxton, Structure and function of lipopolysaccharides, Microbes and Infection, 2002). Copious information relating to endotoxins, e.g. LPS, as well as their impact on health may be found in the book "Endotoxin in Health and Disease", edited by Helmut Brade, Steven M. Opal, Stefanie N. Vogel and David C. Morrison, 1999, published by Marcel Dekker, Inc., ISBN 0-8247-1944-1.

As mentioned above, endotoxin may derive from different bacterial sources. The chemical nature of endotoxin may vary slightly from source to source. For instance, endotoxins derived from different bacterial sources may differ slightly in the length of the aliphatic chains in the aliphatic amides and aliphatic acid esters of the lipid A domain. However, despite slight variations in endotoxin structure from source to source, the same basic structure as described herein above applies for most if not all endotoxins, implying a similar mode of action, and a correspondingly similar mode of influencing endotoxin behavior regardless of the bacterial species of origin. Examples of known endotoxins include those derived from e.g. *E. coli*, e.g. *E. coli* O55:B5 (such as available from Sigma as product number L2637-5MG) or *E. coli* K 12; *S. abortus* equi (such as available from Acila as product number 1220302); *Klebsiella pneumonia; Morganella morganii; Yersinia enterocolitica; Serratia marcescens; Neisseria*, e.g. *Neisseria* meningitis; *Acinetobacter baumanni; Enterobacter cloacae*, e.g. naturally occurring endotoxin (NOE); *Pseudomonas*, e.g. *Pseudomonas aeruginosa; Salmonella*, e.g. *Salmonella* enteric; *Shigella; Haemophilus* influenza; *Bordatella pertussis*; and *Vibrio cholerae*. It is to be understood that this list is merely exemplary and in no way restricts the term "endotoxin" as used herein.

Endotoxin Masker

The term "endotoxin masker" refers to a substance which, in solution with the endotoxin, renders the endotoxin undetectable by available detection methods, e.g. by limulus amebocyte lysate (LAL) tests. Typically, endotoxin is detectable when it exists in solution in aggregated form, i.e. in a form in which multiple, or least two endotoxin moieties are held together in spatial proximity by non-covalent interactions such as electrostatic interactions, hydrophobic interactions, Van der Waals interactions or any combination thereof. However, endotoxin becomes significantly less active (undetectable) as measured by common detection systems, i.e. is masked, when its active aggregation state is changed such that the endotoxin becomes solubilized as individual molecules of endotoxin. It can be assumed that discrete molecular entities of endotoxin are stabilized, for example, by detergents present in the solution. Such detergents are assumed to stabilize individual endotoxin moieties by forming detergent micelles in which the individual endotoxin moieties become embedded and are no longer capable of reacting with Factor C in commercially available endotoxin assays. Certain proteins may also effect or contribute to stabilization of endotoxin in undetectable soluble form. For instance, such proteins may present the endotoxin with binding clefts offering individual endotoxin molecules a suitable environment for stable binding, thereby breaking up otherwise detectable endotoxin aggregates and/or preventing the endotoxin molecules from interacting with Factor C in available endotoxin assays.

It is assumed that at least two molecules of endotoxin, that is at least two molecules of LPS, must form an aggregate in order to be detectable by commercially available endotoxin tests such as the EndoLISA® test kit available from Hyglos GmbH and LAL-based tests.

In fact, several publications show that endotoxin aggregates are significantly more biologically active than disaggregated endotoxins (M. Mueller, B. Lindner, S. Kusumoto, K. Fukase, A, B. Schromm, U. Seydel, Aggregates are the biologically active units of endotoxin, The Journal of biological Chemistry, 2004; A. Shnyra, K. Hultenby, A. Lindberg, Role of the physical state of *Salmonella* Lipopolysaccharide in expression of biological and endotoxic properties, Infection and Immunity, 1993). Furthermore, the activation of Factor C, described by Tan et al. (N. S. Tan, M. L. P. NG, Y. H Yau, P. K. W. Chong, B Ho, J. L. Ding, Definition of endotoxin binding sites in horseshoe crab Factor C recombinant sushi proteins and neutralization of endotoxin by sushi peptides, The FASEB Journal, 2000), is indicated as a cooperative binding mechanism. Here, as mentioned above, at least two LPS molecules are required for activation of Factor C, which is the key factor in limulus based detection methods such as the EndoLISA kit available from Hyglos GmbH.

Examples of endotoxin maskers which are detergents include anionic detergents, cationic detergents, nonionic detergents and amphoteric detergents, and any combination thereof.

Examples of anionic detergents which may function as detergent endotoxin maskers in the sense of the invention include alkyl sulfates such as for example ammonium lauryl sulfate or sodium lauryl sulfate (SDS); alkyl-ether sulfates such as for example sodium laureth sulfate or sodium myreth sulfate; cholesterol sulfate; sulfonates such as for example dodecylbenzensulfonate, sodiumlauryl sulfoacetate or xylene sulfonate; alkyl sulfo succinates such as for example disodium lauryl sulfosuccinate; sulfoxides such as for example dodecyl methyl sulfoxide; phosphates such as for example trilaureth-4 phosphate; and carboxylates such as for example sodium stearate or sodium lauroyl sarcosinate.

Examples of cationic detergents which may function as endotoxin maskers in the sense of the invention include primary amines; secondary amines; tertiary amines; and quaternary ammonium cations such as for example alkyltrimethylammonium salts (e.g. cetyl trimethylammonium bromide (CTAB) or cetyl trimethylammonium chloride (CTAC)); cetylpyridinium chloride (CPC); quaternary ammonium detergents such as for example tris[2-(2-hydroxyethoxy)ethyl]-octadecyl-ammonium phosphate (Quaternium 52); and hydroxyethylcellulose ethoxylate, quaternized (Polyquaternium-10).

Nonionic detergents which may function as detergent endotoxin maskers in the sense of the invention include polyoxyethylene glycol sorbitan alkyl esters (polysorbates) such as for example polysorbate 20 (Tween-20), polysorbate 40, polysorbate 60 or polysorbate 80 (Tween-80); polyoxyethylene glycol alkyl ethers; polyoxypropylene glycol alkyl ethers; glucoside alkyl ethers; polyoxyethylene glycol octylphenol ethers; polyoxyethylene glycol alkylphenol ethers; glycerol alkyl esters; sorbitan alkyl esters; block copolymers of polyethylene glycol and polypropylene glycol; cocamide MEA; sterols such as for example cholesterol; cyclodextrans; poloxamers such as for example Pluronic block polymers (for example $HO-(CH_2CH_2O)_{n/2}-(CH_2CH(CH_3)O)_m-(CH_2CH_2O)_{n/2}-H$, with n=200 and m=65 for F127 and n=4.5 and m=31 for F61) and cocamide DEA.

Amphoteric detergents which may function as detergent endotoxin maskers in the sense of the invention include CHAPS (3-[(3-Cholamidopropyl)dimethylammonio]-1-propanesulfonate); sultaines, such as for example cocamidopropyl hydroxysultaine; betaines, such as for example cocamidopropyl betaine; amine oxides such as for example palmitamine oxide, laurylamine oxide and amine oxide of general formula $R^3N^+O^-$, wherein $R^3$ is $C_8$-$C_{18}$ alkyl, $C_8$-$C_{18}$ alkenyl or $C_8$-$C_{18}$ alkynyl; and lecithin. Specifically, $R^3$ in the above general formula $R^3N^+O^-$ may be any of $C_8$ alkyl, $C_9$ alkyl, $C_{10}$ alkyl, $C_{11}$ alkyl, $C_{12}$ alkyl, $C_{13}$ alkyl, $C_{14}$ alkyl, $C_{15}$ alkyl, $C_{16}$ alkyl, $C_{17}$ alkyl or $C_{18}$ alkyl; or $C_8$ alkenyl, $C_9$ alkenyl, $C_{10}$ alkenyl, $C_{11}$ alkenyl, $C_{12}$ alkenyl, $C_{13}$ alkenyl, $C_{14}$ alkenyl, $C_{15}$ alkenyl, $C_{16}$ alkenyl, $C_{17}$ alkenyl or $C_{18}$ alkenyl; or $C_8$ alkynyl, $C_9$ alkynyl, $C_{10}$ alkynyl, $C_{11}$ alkynyl, $C_{12}$ alkynyl, $C_{13}$ alkynyl, $C_{14}$ alkynyl, $C_{15}$ alkynyl, $C_{16}$ alkynyl, $C_{17}$ alkynyl or $C_{18}$ alkynyl.

Alternatively or in addition to any of the endotoxin maskers indicated above (alone or in combination), the endotoxin masker may also be an active pharmaceutical ingredient (API). This API may exist in solution together with or without any of the detergent endotoxin maskers indicated above. If the API exists together with a detergent endotoxin masker in solution, the masking effect may be more pronounced, and more stringent measures may be necessary to liberate masked endotoxin from the endotoxin masker, as is discussed in greater detail below. APIs which may especially engender or augment the masking of endotoxin present in the solution are protein APIs, for example an antibody; an antibody fragment; a hormone; an enzyme; a fusion protein; a protein conjugate; and any combination thereof. When the protein API is an antibody fragment, the antibody fragment may be preferably chosen from the group consisting of: Fab; a Fab'; a F(ab')2; an Fv; a single chain antibody; and any combination thereof. When the protein API is an antibody, the antibody may be preferably chosen from the group consisting of: a fully human antibody; an anti-idiotype antibody; a humanized antibody; a bispecific antibody; a chimeric antibody; a CDR-grafted antibody; a monoclonal antibody; a polyclonal antibody; and any combination thereof. Alternatively or in addition to the above, the API may also be a small organic molecule. The skilled person understands what is meant by the term "small organic molecule" or "small molecule". This is a molecule with a molecular weight of no more than 300 g/mol, 400 g/mol, 500 g/mol, 600 g/mol, 700 g/mol, 800 g/mol, 900 g/mol or, preferably, 1000 g/mol.

Generally, an endotoxin masker, whether a detergent or a protein, will have the characteristic of shifting the equilibrium between solubilized and aggregated endotoxin in the direction of solubilized endotoxin which is not detectable by available endotoxin assays. It is this shifting of endotoxin into an undetectable form which is referred to as "masking" herein. As mentioned above, the form in which the endotoxin is solubilized may for example include endotoxin a) being embedded in the lipid layer of a micelle formed by a detergent; b) being bound on or in a protein, e.g. in a suitable binding cleft of appropriate steric and electrostatic environment formed on the surface of an active pharmaceutical agent, e.g. a protein; or c) participating in a combination of these two possibilities. Regardless of the form in which endotoxin is solubilized so as to energetically disfavor the aggregate form, however, the net effect is that individual molecules of endotoxin which would otherwise be aggregated and therefore detectable, are individually stabilized and, in this individualized (solubilized) form, become and remain undetectable, i.e. masked.

Although undetectable, however, such stabilized endotoxin molecules in solution can nevertheless engender and/or contribute to the sorts of pyrogenic and/or toxic reactions outlined above when administered to subjects. This danger is especially acute in pharmaceutical formulations, since pharmaceutical formulations often contain a detergent to solubilize an API, e.g. a protein API, which, without the detergent, would be insoluble at the concentrations provided in the pharmaceutical formulation. In rendering the API, e.g. protein API, soluble by including detergent, then, one often unwittingly destroys the very aggregation of endotoxin which is needed for detection of this endotoxin. Thus, when the endotoxin masker is a detergent, the very measure employed to formulate the API, e.g. protein API, in acceptable form and concentration also has the potential to mask endotoxin in solution.

As mentioned above the endotoxin masker may also be a protein, for instance the API itself. This scenario may arise in conjunction with the presence of a detergent endotoxin masker or, in the event that no detergent is present, may also arise in the absence of a detergent endotoxin masker. In this latter case, the API, in particular a protein API, may offer the endotoxin a sufficient environment for stable binding on or in such protein such that the endotoxin is masked by the API alone, i.e. without any detergent being necessary to mask endotoxin, rendering it undetectable. In the event that the endotoxin masker is a protein, this protein may be the API itself, or may alternatively or additionally be a protein in solution which is different from the API. Generally, any protein having an appropriate steric and electrostatic environment to stabilize individual molecules of endotoxin, for instance individual molecules of LPS could potentially effect or contribute to the masking of endotoxin.

It is a hallmark of the invention that when the endotoxin masker is a protein, either alone or together with an additional endotoxin masker such as e.g. a detergent endotoxin masker, unmasking the endotoxin leaves the protein endotoxin masker chemically unaltered following unmasking. In particular, unmasking the endotoxin does not cleave or otherwise degrade the protein endotoxin masker (e.g. protein API).

In scenarios of the type described above, individual molecules of endotoxin which would otherwise remain in aggregates and therefore detectable, are stabilized at one or more such surface locations on or in said protein. As is the case for detergent micelles, such stabilization shifts the equilibrium existing between solubilized (undetectable) and aggregated (detectable) in the direction of solubilized (undetectable) endotoxin. As mentioned above, one may imagine such a shift of equilibrium toward the solubilized (undetectable) form as being especially pronounced in the event that a solution comprises both detergent and one or more proteins with the above characteristics, since in such cases the stabilization of individual molecules of endotoxin out of its aggregate form by the endotoxin masker may ensue both in the form of stabilization in micelles as well as on the surface of proteins. In such scenarios, more stringent measures may be required to shift said equilibrium toward the aggregate endotoxin form which is then detectable. These are discussed in more detail in the context of illustrative scenarios further below (FIGS. 1-6).

Modulator

The term "modulator" as used herein refers to one or more compounds which, alone or in concert, render(s) a masked endotoxin susceptible to detection by an endotoxin assay (such as the EndoLISA® detection assay available from Hyglos GmbH). The term "modulator" as used herein may encompass both single as well as multiple components which achieve this end. In some instances herein below, reference is made to a "modulator system", although the term "modulator" is sometimes used to designate multiple modulator substances which are intended to work in concert. This refers to a multi-component modulator comprising multiple substances which act in concert to render a masked endotoxin detectable by an endotoxin assay. The different components of a modulator system may be incorporated for different reasons, i.e. to take advantage of different functions of modulator substances which affect the stability of a complex between endotoxin and endotoxin masker in different ways. For ease of reference, one may for example refer to different kinds of modulator which may be employed alone or together to unmask endotoxin:

"Disrupting modulator": A "disrupting modulator" is a modulator which completely or partially breaks up a complex between an endotoxin masker and an endotoxin. When the endotoxin masker is a detergent, and the endotoxin is masked in solubilized form inserted in the lipid layer of a masking detergent micelle, then a modulator which disrupts such a detergent micelle so as to liberate the endotoxin would be referred to as a disrupting modulator. As discussed in greater detail below, 1-dodecanol is one such disrupting modulator. A disrupting modulator, for example 1-dodecanol, 1-decanoic acid or sodium octyl sulfate (SOS) may advantageously be used in a concentration range of 0.01-100 mM, preferably in a concentration range of 0.1-10 mM, preferably at a concentration of 10 mM in the unmasking process. In some cases, the disrupting modulator may also simultaneously function as a reconfiguring modulator, described below.

"Adsorbing modulator": An "adsorbing modulator" is a modulator which has the ability to bind substances which would otherwise stabilize the endotoxin in solubilized and therefore non-detectable form. For instance, when the endotoxin masker is a detergent as e.g. contained in some pharmaceutical compositions, then a modulator which binds molecules of the detergent and in this way contributes to the breakdown of endotoxin-stabilizing micelles would be referred to as an adsorbing modulator. As discussed in greater detail below, BSA is one such adsorbing modulator. An adsorbing modulator, for example BSA may advantageously be used in a concentration range of 0.1-20 mg/mL, preferably in a concentration range of 1-10 mg/mL, preferably at a concentration of 10 mg/ml in the unmasking process.

"Displacing modulator": A "displacing modulator" is a modulator which has the ability to completely or partially displace a molecule of endotoxin from its stable binding position in or on an endotoxin masker. For instance, when the endotoxin masker is a protein, and the endotoxin is bound in or on a protein which stabilizes the endotoxin in undetectable form, then a modulator which has the ability to replace the endotoxin in or on the protein, e.g. by means of hydrophobic interactions, would be referred to as a displacing modulator. As discussed in greater detail below, SDS is one such displacing modulator. A displacing modulator, for example SDS, may advantageously be used in a concentration range of 0.01-1 wt %, preferably in a concentration range of 0.05-0.5 wt %, preferably in a concentration range of 0.02-0.2 wt %, preferably at a concentration of 0.1 wt % in the unmasking process.

"Reconfiguring modulator": A "reconfiguring modulator" is a modulator which has the ability to transiently stabilize endotoxin following its liberation from the endotoxin masker (e.g. by a disrupting modulator or displacing modulator, as discussed above), thus helping the liberated, solubilized (undetectable) endotoxin to adopt an aggregated (detectable) form. With the help of the reconfiguring modulator, solubilized endotoxin becomes reconfigured as aggregated endotoxin. As discussed in greater detail below, 1-dodecanol is one such reconfiguring modulator. A reconfiguring modulator, for example 1-dodecanol, 1-decanoic acid or sodium octyl sulfate (SOS) may advantageously be used in a concentration range of 0.01-100 mM, preferably in a concentration range of 0.1-10 mM in the unmasking process. In some cases, the reconfiguring modulator may also simultaneously function as a disrupting modulator, described above.

As will become clear herein below, the above types of modulator are not mutually exclusive; that is, it is possible for a given substance to have functionality as different kinds of modulators above. One example is 1-dodecanol, which may be classified as both a disrupting modulator (breaking up a detergent micelle) as well as a reconfiguring modulator (transiently stabilizing the micelle-liberated endotoxin so it can aggregate and become detectable). Similarly SDS may be classified as a disrupting modulator (breaking up existing micelles of another, non-SDS detergent) and a displacing modulator (liberating endotoxin from binding sites in or on any masking protein which may be present). The classification as to the type of modulator depends on the function that a substance in question plays in a particular composition. However, since it is assumed that reconfiguring of the endotoxin from solubilized into aggregated form will generally be required in order to render the endotoxin detectable, the modulator will normally comprise at least one component qualifying as a "reconfiguring modulator".

As a further example, a substance which functions as a "displacing modulator" when the endotoxin masker is a protein may in some cases function as a "disrupting modulator" when the endotoxin masker is a detergent. SDS is one example of such a substance, the classification of which as to the type of modulator component depends on the prevailing conditions. For instance, when the endotoxin masker is a protein, SDS will generally function as a displacing modulator, since it helps to displace the endotoxin bound in or on the masking protein. However, when the endotoxin masker is a detergent, then SDS, alone or together with another modulator component, may function more as a disrupting modulator, since in this case it promotes the liberation of endotoxin from the lipid layer of detergent micelles by disrupting the micelles.

A modulator may contain one or more substances within the above classifications. For instance, a single component modulator may comprise only a disrupting modulator such as 1-dodecanol. A dual-component modulator may comprise a mixture of a disrupting modulator such as 1-dodecanol (also possibly functioning as a reconfiguring modulator) and, depending on the nature of the masking complex between endotoxin and endotoxin masker, one of an adsorbing modulator such as BSA or a displacing modulator such as SDS. A multi-component modulator may comprise a mixture of a disrupting modulator such as 1-dodecanol (also possibly functioning as a reconfiguring modulator) and, depending on the nature of the masking complex between endotoxin and endotoxin masker, one each of an adsorbing modulator such as BSA and a displacing modulator such as SDS. As will be discussed in detail below, the complexity of the modulator system chosen will depend on the nature of the complex between endotoxin and endotoxin masker, and the surrounding solution conditions which contribute to the stability of that complex. From the above, it is clear that each new composition to be analyzed for the presence of endotoxin may require its own customized modulator composition in order to render the masked endotoxin susceptible to detection. The identification of a suitable modulator for a given composition or formulation to be tested can however be accomplished by routine experimentation, as will be shown further below.

As mentioned above, in its most general sense, the modulator is assumed to destabilize a complex between endotoxin and an endotoxin masker and to promote the liberation of the endotoxin from the endotoxin masker. In this way, the modulator or modulator system effectively shifts the equilibrium from a solubilized (undetectable) state toward an aggregated (detectable) state.

The present inventors have surprisingly found that endotoxin which is present but undetectable in solution remains undetectable because, as assumed, the endotoxin remains stably solubilized in detergent micelles and/or bound to surface structures of proteins present in the solution. Individually stabilized in this form, the endotoxin molecules evade detection. However, the present inventors have found that solution conditions can be manipulated such that solubilized endotoxin is rendered into a form which can be detected. In some instances, multiple manipulations of solution conditions may be required to reach this end and the stringency of the measure or measures taken to effect the desired shift in equilibrium toward an aggregated state will vary depending on the degree to which the endotoxin masker stabilizes the endotoxin in solubilized form, as mentioned above. But generally, the manipulations performed in accordance with the invention as described herein should be understood in the context of the overall aim of shifting the equilibrium of endotoxin from a solubilized state to an aggregated state such that it can be detected.

In order to accomplish the above, the "modulator" will generally include an amphiphilic molecule which competes for binding between the lipid component of endotoxin and the endotoxin masker, thus weakening the interaction between the former and the latter. Such competitive binding will generally be accomplished by providing at least one component of the modulator system in a form which is structurally similar to the (amphiphilic) lipid component of the endotoxin such that the former may displace the latter in its stabilized interaction with the endotoxin masker.

For instance, in the event the endotoxin masker is a detergent, a suitable disrupting modulator will generally include an amphiphilic compound capable of stably inserting i.e. between the amphiphilic detergent molecules and the similarly amphiphilic lipid portion of the endotoxin. When the endotoxin masker is a detergent, an amphiphilic disrupting modulator will therefore elicit several effects in parallel which are conducive to an overall shift in equilibrium from a solubilized toward an aggregated form of endotoxin. First, providing a modulator system comprising at least one amphiphilic disrupting modulator disrupts the lipophilic interactions underlying the detergent micelles such that these micelles are broken up. Since endotoxin was previously solubilized (and therefore masked) by insertion of its lipid component into the lipid layer of the detergent micelles, the breakup of the micelles removes this stabilizing force and results in the liberation of previously embedded endotoxin. The role of the disrupting modulator in the event that the endotoxin masker is or includes a detergent is thus to break up detergent micelles.

Further, the amphiphilic character of the disrupting modulator may also enable it to associate with the lipid component of the endotoxin, once the endotoxin is liberated from its detergent micelles as described above. This interaction between the amphiphilic disrupting modulator and the lipid component of the endotoxin has the effect of chaperoning the endotoxin in aqueous solution following its liberation from the stabilizing detergent micelles. In this event, the disrupting modulator would have a double function as a reconfiguring modulator. When the disrupting modulator is amphiphilic in character, it is not excluded that it may be capable for forming micelles of its own. However, the unmasking effect will generally be greatest when the amphiphilic disrupting modulator does not form micelles of its own which might simply swap one solubilized and therefore masked endotoxin state for another. A key role of the reconfiguring modulator is thus to transiently stabilize liberated endotoxin (albeit less than in its previous complex with the endotoxin masker), effectively chaperoning the endotoxin into an aggregated and therefore detectable state.

Thus temporarily chaperoned in solution, the liberated endotoxin is then free to aggregate into a form which is detectable and therefore "unmasked". Whether or not further manipulation of solution conditions beyond addition of the modulator or modulator system is necessary to shift equilibrium towards this aggregated, detectable form will generally depend on the conditions prevailing in solution and the initial stability of the endotoxin as complexed with the endotoxin masker.

In another scenario already contemplated above, the endotoxin masker is not, or not only a detergent, but may also be or comprise a protein with binding clefts on its surface suitable to stably bind individual moieties of endotoxin such that it cannot be detected. In this event, similar considerations pertaining to the modulator apply as set out above. For instance, use of a disrupting (amphiphilic) modulator and/or a displacing modulator in the event that the endotoxin is or comprises a protein has the effect that the modulator disrupts the lipophilic interactions existing between lipophilic amino acid side chains of the protein (endotoxin masker) and the lipid component of the endotoxin. Because the disrupting modulator and/or displacing modulator is/are likely to be amphiphilic in character, the modulator(s) would also be able to disrupt electrostatic interactions existing between polar and/or ionized side chains within the protein (endotoxin masker) and polar groups within the core and/or O-antigen polysaccharide regions of the endotoxin. With these stabilizing interactions disrupted, the endotoxin which was previously masked by a protein endotoxin masker is thus displaced from its previous complex with the protein, and is chaperoned in solution into an aggregated state by association with a reconfiguration modulator as described above.

As described above for the case in which the endotoxin masker is a detergent in the absence of a protein endotoxin masker, the liberated and reconfiguation modulator-chaperoned endotoxin is then free to aggregate into a form which is detectable and therefore "unmasked". Whether or not further manipulation of solution conditions beyond addition of the components of the modulator system is necessary to shift equilibrium towards this aggregated, detectable endotoxin form will generally depend on the conditions prevailing in solution and the initial stability of the endotoxin as complexed with the endotoxin masker.

The modulator, e.g. the disrupting modulator, the displacing modulator and/or the reconfiguring modulator may in certain embodiments comprise a first heteroatom-substituted aliphatic, wherein the main chain of the first heteroatom-substituted aliphatic comprises 8 to 16 carbon atoms. As used herein, the term "main chain" refers to the longest chain of the first heteroatom-substituted aliphatic comprising 8 to 16 carbon atoms, as numbered by standard IUPAC nomenclature. Specifically, the main chain of the first heteroatom-substituted aliphatic may comprise 8, 9, 10, 11, 12, 13, 14, 15 or 16 carbon atoms. As used herein, the term "heteroatom" refers to any atom other than carbon, to which a carbon atom in the first heteroatom-substituted aliphatic is covalently bound. Representative heteroatoms include oxygen, nitrogen and sulfur atoms. In a further preferred embodiment, the oxygen-substituted aliphatic is an aliphatic alcohol, in particular, 1-dodecanol, that is the molecule given by the formula $HO-(CH_2)_{11}-CH_3$. As mentioned above, 1-dodecanol is especially well suited in many instances as a disrupting modulator as well as, in most if not all instances, as a reconfiguring modulator.

The reconfiguring modulator is assumed to play an especially important, if not indispensible role in promoting an aggregated, detectable form of endotoxin. The reconfiguring modulator may be a heteroatom-substituted aliphatic comprising 8, 9, 10, 11, 12, 13, 14, 15 or 16 carbon atoms in its main chain. The term "main chain" refers to the longest chain of the reconfiguring modulator, as numbered by standard IUPAC nomenclature. As used herein, the term "heteroatom" refers to any atom other than carbon, to which a carbon atom in the first heteroatom-substituted aliphatic is covalently bound. Representative heteroatoms include oxygen, nitrogen and sulfur atoms. It is especially suitable when the heteroatom is oxygen. Furthermore, the reconfiguring modulator may be branched or unbranched, with the branched variants comprising substitutions along the "main chain" as defined above. Said substitutions may be e.g. methyl, ethyl, propyl and/or butyl. An unbranched chain is preferred. The reconfiguring modulator may be saturated to various extents, and may for example comprise a $C_8$ alkyl, $C_9$ alkyl, $C_{10}$ alkyl, $C_{11}$ alkyl, $C_{12}$ alkyl, $C_{13}$ alkyl, $C_{14}$ alkyl, $C_{15}$ alkyl or $C_{16}$ alkyl moiety; or a $C_8$ alkenyl, $C_9$ alkenyl, $C_{10}$ alkenyl, $C_{11}$ alkenyl, $C_{12}$ alkenyl, $C_{13}$ alkenyl, $C_{14}$ alkenyl, $C_{15}$ alkenyl or $C_{16}$ alkenyl moiety; or a $C_8$ alkynyl, $C_9$ alkynyl, $C_{10}$ alkynyl, $C_{11}$ alkynyl, $C_{12}$ alkynyl, $C_{13}$ alkynyl, $C_{14}$ alkynyl, $C_{15}$ alkynyl or $C_{16}$ alkynyl moiety. Furthermore, the reconfiguring modulator may contain any mixture of single, double and triple carbon-carbon bonds. Especially suitable reconfiguring modulators are saturated, i.e. comprise $C_8$ alkyl, $C_9$ alkyl, $C_{10}$ alkyl, $C_{11}$ alkyl, $C_{12}$ alkyl, $C_{13}$ alkyl, $C_{14}$ alkyl, $C_{15}$ alkyl or $C_{16}$ alkyl. Especially suitable reconfiguring modulators comprise $C_{12}$ alkyl. Furthermore, the heteroatom may be of various oxidation states.

For instance, when the heteroatom is oxygen, the oxygen may be in the form of an alcohol, an aldehyde or a carboxylic acid. Especially suitable as reconfiguring modulators are molecules in unbranched alkanols, in particular unbranched 1-alkanols. Among these, especially suitable are $C_{12}$ alkanols, especially 1-dodecanol having the formula $HO-(CH_2)_{11}-CH_3$.

In further embodiments, the modulator system may include other components in addition to said first heteroatom-substituted aliphatic comprising 8 to 16 carbon atoms. For example, the modulator system may additionally comprise a second heteroatom-substituted aliphatic, e.g. as a disrupting modulator, a displacing modulator and/or a reconfiguring modulator, wherein the main chain of said second heteroatom-substituted aliphatic comprises 8 to 16 carbon atoms. The "main chain" of the second heteroatom-substituted aliphatic is defined as described above for the first heteroatom-substituted aliphatic. Specifically, the main chain of the second heteroatom-substituted aliphatic may comprise 8, 9, 10, 11, 12, 13, 14, 15 or 16 carbon atoms. The first heteroatom-substituted aliphatic comprising 8 to 16 carbon atoms is different than the second heteroatom-substituted aliphatic comprising 8 to 16 carbon atoms. In a preferred embodiment, the second heteroatom-substituted aliphatic which may be part of the modulator is an oxygen-substituted aliphatic. In certain preferred embodiments, this oxygen-substituted aliphatic is an aliphatic sulfate, wherein it is especially preferred that this aliphatic sulfate is sodium dodecyl sulfate (SDS). Thus, in a particularly preferred embodiment of the invention, the modulator system includes a first heteroatom-substituted aliphatic which is 1-dodecanol (e.g. as a disrupting modulator and/or a reconfiguring modulator), and a second heteroatom-substituted aliphatic which is SDS (as a further disrupting modulator and/or a displacing modulator).

In a further embodiment, the modulator system as described above may further comprise a protein capable of binding a detergent so as to break up micelles formed by said detergent. Generally, the detergent bound will be the endotoxin masker (when said endotoxin masker is or comprises a detergent), and the principle by which the protein capable of binding a detergent binds the detergent is analogous to the principle described above, according to which a protein which functions as an endotoxin masker sequesters portions of the endotoxin molecule in or on its surface. In the present embodiment, the protein capable of binding a detergent, when used as part of the modulator, also bears on its surface areas of steric and electrostatic compatibility with a portion or portions of detergent molecules present in solution, which are sufficient to bind or sequester detergent molecules, thus rendering them unavailable for participation in micelles and thus breaking up any detergent micelles which may be harbor endotoxin, or which may serve to shift equilibrium away from an aggregated form of endotoxin.

The inventors have found that albumin molecules are exceptionally good at binding detergent. Thus, it is contemplated that in addition to the first heteroatom-substituted aliphatic alone, or in addition to the first heteroatom-substituted aliphatic in combination with the second heteroatom-substituted aliphatic, the modulator may additionally comprise a protein (adsorbing modulator) capable of binding a detergent so as to break up micelles formed by said detergent. In certain embodiments, the protein component of the modulator may be an albumin, preferably human serum albumin (HSA), bovine serum albumin (BSA) or ovalbumin (OVA).

It is additionally contemplated that the modulator may contain one or more of each of the first heteroatom-substituted aliphatic comprising 8 to 16 carbon atoms, the said second heteroatom-substituted aliphatic comprising 8 to 16 carbon atoms and said protein capable of binding a detergent so as to break up micelles formed by said detergent. In a preferred embodiment of the invention, the modulator comprises 1-dodecanol alone. In a further preferred embodiment of the invention, the modulator comprises 1-dodecanol and SDS. In a further preferred embodiment of the invention, the modulator comprises 1-dodecanol, SDS and HSA. In a further preferred embodiment of the invention, the modulator comprises 1-dodecanol, SDS and BSA.

Composition

As used herein, the term "composition" refers to a mixture comprising (at least) an endotoxin masker. The endotoxin, even if present and masked, remains undetectable in the composition.

The composition is preferably a pharmaceutical composition, e.g. a composition comprising an active pharmaceutical ingredient, or API. The term "composition" may be e.g. an extract; vaccine; any composition suitable for parenteral administration, i.e. parentalia; any composition suitable for intraperitoneal, transdermal, subcutaneous or topical administration; a blood product; a cell therapy solution, e.g. intact, living cells, for example, T cells capable of fighting cancer cells; a gene therapy solution, e.g. a solution capable of nucleic acid polymer delivery into a patient's cells as a drug to treat disease; an implant or medical device; or a composition resulting from rinsing or wiping the surface of an object, said object for instance being a medical device, an implant or a filling machine.

Detection Method

As used herein, the term "detection method" refers to a method which is suitable for detecting endotoxin in solution. For example, suitable methods in this regard are limulus based detection methods, or is an enzyme linked immunosorbent assays (ELISA). The limulus methods can be performed classically by using natural derived lysate (J. Jorgensen, R. Smith, Preparation, Sensitivity, and Specificity of Limulus Lysate for Endotoxin Assay, Applied Microbiology, 1973) or recombinantly prepared Factor C (J. L. Ding, B. Ho, A new era in pyrogen testing, Trends in Biotechnology, 2001). The most promising of such methods are enzyme-linked affinitysorbent assays, using a solid phase for endotoxin capturing and subsequent detection by recombinant version of a protein in the LAL assay, Factor C. The EndoLISA® kit is one such affinitysorbent assay (H. Grallert, S. Leopoldseder, M. Schuett, P. Kurze, B. Buchberger, EndoLISA®: a novel and reliable method for endotoxin detection, Nature Methods, 2011). The EndoLISA® detection system is for example described in the book "Pharmazeutische Mikrobiologie—Qualitätssicherung, Monitoring, Betriebshygiene" by Michael Rieth, October 2012, Wiley-VCH, Weinheim, ISBN 978-3-527-33087-4.

Agent which Influences Hydrogen Bonding Stability in Solution

According to a further embodiment of the invention, the above methods of unmasking an endotoxin and/or the method of detecting an endotoxin may further comprise the step of adding to said composition an agent which influences hydrogen bonding stability in solution. Generally, as used herein, an agent which influences hydrogen bonding stability in solution modifies solution conditions so as to destabilize the complex in which an individual molecule or multiple molecules of endotoxin is/are solubilized and therefore masked.

Not all complexes between endotoxin and endotoxin masker are the same. In particular, the energy minima governing endotoxin stabilization in certain masking complexes are different than those governing endotoxin stabilization in other masking complexes. All other things being equal, the lower an energy minimum governing the stabilization of endotoxin in a given complex with an endotoxin masker is, the more difficult it will be, i.e. the more stringent the modulator must be, to liberate endotoxin from its solubilized state. Yet as mentioned above, such liberation is an important step in the eventual aggregation of endotoxin into a detectable, i.e. unmasked, form. Thus, the more stable the complex between endotoxin and endotoxin masker, the more rigorous must be the measures taken to ultimately unmask the endotoxin.

In instances where the complex between endotoxin and endotoxin masker is especially stable, addition of a single- or even multiple-component modulator may sometimes not be enough to destabilize the masking complex and liberate the endotoxin. It may in such instances be helpful to promote endotoxin liberation from its complex with endotoxin masker by adjusting solution conditions so as to destabilize the endotoxin-endotoxin masker complex.

As mentioned above, an agent which influences hydrogen bonding stability in solution may assist in this aim. Some, if not most of the stabilization of endotoxin in complex with an endotoxin masker normally arises from non-covalent interactions between the endotoxin moiety and the endotoxin masker. These interactions may for instance take the form of hydrophobic, ionic, hydrogen bonding and/or Van der Waals interactions between regions of the endotoxin molecule and regions on the molecule or molecules of the endotoxin masker. As the strength of these endotoxin-endotoxin masker interactions is influenced by the surrounding hydrogen bonding network in solution, it conversely follows that influencing the hydrogen bonding stability in solution will modulate the strength of these interactions. Addition of an agent which influences hydrogen bonding stability in solution can therefore help to weaken the noncovalent bonding interactions between endotoxin and endotoxin masker, essentially raising the free energy of the complex and thus rendering it more susceptible to disruption by the modulator so that the endotoxin is liberated and rendered detectable.

Besides the destabilizing effect discussed above, an agent which influences hydrogen bonding stability in solution may also have a further effect promoting endotoxin unmasking. By altering hydrogen bonding stability in solution, the agent may also foster aggregation of the endotoxin moieties once liberated from their complex with endotoxin masker. There will generally exist an equilibrium between endotoxin in solubilized and aggregated forms. The agent which influences hydrogen bonding stability in solution can be helpful in shifting this equilibrium towards the aggregated (and thus detectable). Suitable substances are those which would tend to decrease the hydrogen bonding stability in solution surrounding the chaperoned endotoxin moities, and/or compounds which tend to increase the ionic strength of the solution, thus driving the reconfiguring modulator-chaperoned endotoxin moieties together into a lipophilic aggregate.

It should be noted that it may not always be necessary to add an agent which influences hydrogen bonding stability in solution. Whether or not addition of such an agent will be indicated will depend, for instance, on the stability of endotoxin in complex with the endotoxin masker and/or on the position of equilibrium between solubilized, chaperoned and aggregated forms of endotoxin moieties once liberated from the endotoxin masker. For instance, in solutions containing higher concentrations of salt, it is conceivable that the complex of the endotoxin and endotoxin masker may already be instable enough to be broken up by the disrupting modulator alone, and that the endotoxin moieties present in solution following liberation from the endotoxin masker will be instable enough so as to form aggregates without any further assistance. In such situations, an agent which influences hydrogen bonding stability in solution may not be required to achieve unmasking.

On the other hand, there may exist situations, for instance in solutions containing lower concentrations of salt, where the endotoxin-endotoxin masker complex may be of such great stability that a disrupting modulator alone cannot break it up to liberate endotoxin, or where—even if liberated by disrupting modulator alone—the equilibrium between solubilized and aggregated endotoxin lies towards the solubilized form so that the aggregation needed for detection does not occur. In such situations incorporation of an agent which influences hydrogen bonding stability in solution may help to influence the energetics of complexation and/or aggregation so as to favor endotoxin in detectable form.

In general, it can be said that the degree of destabilization of the complex between the endotoxin and endotoxin masker will depend on the amount of salt in solution, with this complex being destabilized to an extent directly proportional to the amount of salt present in solution. As a general rule though, reference may be made to the Hofmeister series, according to which the more chaotropic a salt is, the lower the amount of such a salt will be needed to destabilize a complex between endotoxin and endotoxin masker to a given extent. Merely as an illustrative example, in order to achieve approximately the same degree of destabilization of a complex between endotoxin and endotoxin masker achievable with, say, 100 mM $CaCl_2$, one may need to use, say, 500 mM NaCl. In this example, $CaCl_2$ is more chaotropic than NaCl, so less $CaCl_2$ would be required to achieve the same degree of destabilization.

In certain embodiments of the invention, the agent which influences hydrogen bonding stability in solution may be a chaotropic agent, a cation or a combination thereof. In certain embodiments, the chaotropic agent may be chosen from the group consisting of urea, guanidinium chloride, butanol, ethanol, lithium perchlorate, lithium acetate, magnesium chloride, phenol, a propanol (e.g. 1-propanol or 2-propanol, i.e. isopropanol) and thiourea. In certain embodiments, the cation is a divalent cation, for example $Ca^{2+}$, $Mg^{2+}$, $Sr^{2+}$ and/or $Zn^{2+}$. An especially preferred divalent cation is $Ca^{2+}$.

The agent which influences hydrogen bonding stability in solution, e.g. a divalent cationic salt, e.g. $CaCl_2$, may advantageously be used in a concentration range of 1-400 mM, preferably in a concentration range of 10-200 mM, preferably at a concentration range of 50-100 mM in the unmasking process.

The agent which influences hydrogen bonding stability in solution, e.g. a chotropic agent, e.g. guanidinium chloride, may advantageously be used in a concentration range of 1 mM-1 M, preferably in a concentration range of 25-200 mM, preferably at a concentration range of 10-100 mM in the unmasking process.

Without being bound by theory, and merely to illustrate the principles and possible mechanisms which the present inventors believe underlie the observed advantageous effect of unmasking endotoxin in solution, thereby rendering previously masked an undetectable endotoxin detectable, the following describes several mechanisms of interaction between endotoxin and further components of a given composition containing at least one endotoxin masker. To illustrate these mechanisms, reference is made to FIGS. 1-6.

Unmasking Endotoxin Masked by a Detergent Masker with a Single-Component Modulator, in which the Single Component Functions as Both a Disrupting Modulator and a Reconfiguring Modulator FIG. 1 depicts the scenario in which endotoxin resides in solution together with a detergent which is masking it in individualized form in a detergent micelle. Panel (a) of FIG. 1 shows a single endotoxin moiety which is inserted in the lipid layer of such a detergent micelle via its lipid tail. The detergent molecules constituting the lipid layer of the detergent micelle are symbolized as open circles in panel (a). Because this single moiety of endotoxin is stably inserted in individual form in the lipid layer of the micelle rather than in multimeric, aggregated form, it evades detection using available detection methods (e.g. the EndoLISA® assay of Hyglos GmbH). If the solution shown in panel (a) of FIG. 1 were a pharmaceutical formulation additionally containing an API, it would appear to be endotoxin-free and therefore safe for administration, even though endotoxin is present in the solution. Administering such an ostensibly endotoxin-free formulation to a patient would thus risk unwittingly eliciting the types of dangerous immunological and toxic responses to endotoxin mentioned above.

Above the equilibrium arrows between panels (a) and (b) of FIG. 1, one sees the addition of a disrupting and reconfiguring modulator capable of releasing the endotoxin from a complex between the endotoxin and the endotoxin masker. In the scenario shown in FIG. 1, this "complex" is the endotoxin embedded, via its lipid component, in the lipid layer of a detergent micelle. The disrupting and reconfiguring modulator shown here (an amphiphilic molecule used as a single-component modulator having capacity as both a disrupting and reconfiguring modulator) exhibits the dual properties of breaking up the detergent micelle so as to liberate inserted molecules of endotoxin, as well as of stabilizing the endotoxin once it is liberated from its complex with the endotoxin masker. This latter characteristic is schematically depicted in the upper portion of panel (b) of FIG. 1, showing a molecule of endotoxin stabilized by the disrupting and reconfiguring modulator such that the molecule of endotoxin can exist in chaperoned form outside of the micelles once these are broken up by the modulator. The lower portion of panel (b) makes clear that the disrupting modulator exists in equilibrium, associated with both the liberated endotoxin moiety and detergent previously making up the lipid layer of the detergent micelle prior to the micelles disruption by the disrupting (and reconfiguring) modulator.

As mentioned above, in one embodiment of the present invention, the disrupting and/or reconfiguring modulator may be 1-dodecanol, bearing a polar alcohol moiety, followed by a saturated hydrocarbon tail of 12 carbon atoms. Both the steric and electrostatic configuration of 1-dodecanol is thus similar to that of the lipid moieties of the endotoxin, so that 1-dodecanol can efficiently interact with, and therefore stabilize, the endotoxin after it has been liberated from the detergent micelle.

Another reason why 1-dodecanol is especially suitable for use as a disrupting and/or reconfiguring modulator is that 1-dodecanol, although amphiphilic, does not form micelles. Thus, once the detergent micelle depicted in panel (a) of FIG. 1 is broken up by 1-dodecanol, new micelles of modulator do not reform, which might otherwise remask endotoxin by shifting equilibrium away from its aggregated form. The characteristic of the modulator that it does not form micelles itself thus contributes to the stabilization of endotoxin in solution, aided by the modulator, as depicted in panel (b) of FIG. 1. In the scenario depicted in FIG. 1, the hypothetical prevailing solution conditions are such that equilibrium between the chaperoned moieties of endotoxin shown in panel (b) and the aggregated endotoxin shown in panel (c) already lies in the direction of the aggregate of panel (c). With the aggregate form of endotoxin favored, the endotoxin is already in, or predominantly in an aggregated form which is amenable to detection by known means, e.g. the EndoLISA® test kit of Hyglos GmbH.

Overall, then, FIG. 1 shows the transition from individual endotoxin moieties (solubilized) which are stably inserted in and therefore masked by detergent micelles to a scenario in which the individual moieties of endotoxin have aggregated so as to become detectable. Previously masked endotoxin in panel (a) has been unmasked in panel (c), thereby allowing one to determine that a solution previously thought to be free of endotoxin actually contains this contaminant.

Unmasking Endotoxin Masked by a Detergent Masker with a Dual-Component Modulator Comprising a Disrupting and Reconfiguring Modulator and an Adsorbing Modulator (Protein)

Figure 2:
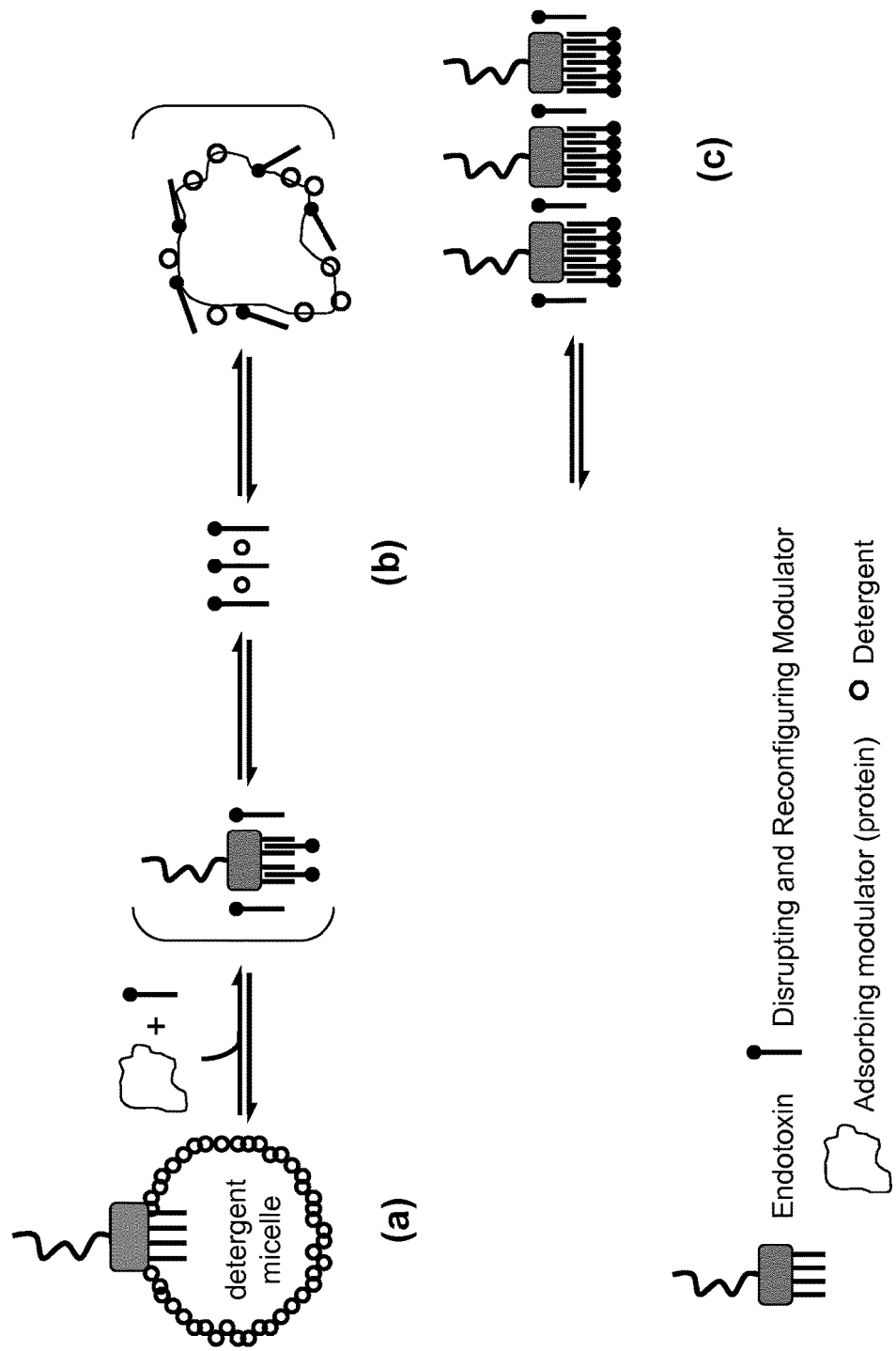
FIG. 2 illustrates a mechanism assumed to underlie the unmasking of endotoxin according to a further embodiment of the present invention. In the scenario depicted in FIG. 2, the endotoxin is present in solution with a detergent (capable of acting as an endotoxin masker), which forms detergent micelles in which endotoxin is embedded and thus masked from detection.

The initial scenario depicted in FIG. 2 is much like that depicted in FIG. 1: a single molecule of endotoxin is inserted in a detergent micelle (symbolized by a ring of open circles representing the individual detergent molecules) and, thus stably individualized, is masked such that it evades detection. Between panels (a) and (b), one sees the addition of a dual-component modulator system comprising both a non-protein component functioning simultaneously as a disrupting and reconfiguring modulator and a protein component functioning as an adsorbing modulator. The disrupting and reconfiguring modulator may be as described as above for FIG. 1, e.g. 1-dodecanol, which helps to disrupt the detergent micelle and stabilize/reconfigure the liberated endotoxin, without forming micelles of its own. The adsorbing modulator may for example be added as part of the modulator in order to promote the disruption of detergent micelles which are more stable than those depicted in FIG. 1, and for which a disruption modulator alone may not suffice to achieve the desired disruption.

As explained above, the adsorbing modulator may for instance be bovine serum albumin (BSA) or human serum albumin (HSA), among other things. Such proteins have the ability to act as "molecular sponges" which adsorb on their surface molecules of the previously micelle-forming detergent. Of course, in the event that such an adsorbing modulator is employed, there will exist a certain equilibrium between other detergent-like molecules in solution, such as the disrupting and reconfiguring modulator. This would be expected to engender an equilibrium as shown in panel (b), in which the disrupting and reconfiguring modulator exists in forms bound to liberated endotoxin (right portion of panel (b)), bound to detergent previously constituting the detergent micelle, as well as bound to the surface of the adsorbing modulator, along with additional detergent from the (now disrupted) detergent micelle.

Under the solution conditions prevailing in the scenario shown in FIG. 2, endotoxin which has been liberated from the masking detergent micelle combine into detectable aggregates, shown in panel (c). In fact, the use of an adsorbing modulator as shown in FIG. 2 can promote such aggregate formation. This is assumed to be because the adsorbing modulator binds molecules of the disrupting and reconfiguring modulator on its surface, thereby removing these otherwise endotoxin-stabilizing species from solution such that equilibrium is driven to the right toward the aggregate of panel (c).

Overall, then, FIG. 2 shows the transition from individual endotoxin moieties which are embedded in detergent micelles and, due to their individualization in these micelles, remain masked, to a scenario in which the individual moieties of endotoxin have been forced to aggregate so as to become detectable. That is, previously masked endotoxin in panel (a) has been unmasked in panel (c), thereby allowing one to determine that a solution previously thought (in panel (a)) to be free of endotoxin actually contains this contaminant (panel (c)).

Unmasking Endotoxin Masked by a Detergent Masker with a Multi-Component Modulator System in Combination with an Agent which Influences Hydrogen Bonding Stability in Solution In the scenarios depicted in FIGS. 1 and 2, the solution conditions were such that use of a modulator system alone suffices to disrupt masking detergent micelles. Looked at another way, neither of the masking micelles of detergent shown in FIGS. 1 and 2 have been so stable as to resist disruption using a disrupting modulator alone. In addition, the conditions in FIGS. 1 and 2 have also been such that the equilibria between the solubilized and aggregated forms of endotoxin lay toward the aggregated form, so that detection of this aggregated form was possible under the solution conditions shown without any further measures needing to be taken.

Figure 3:
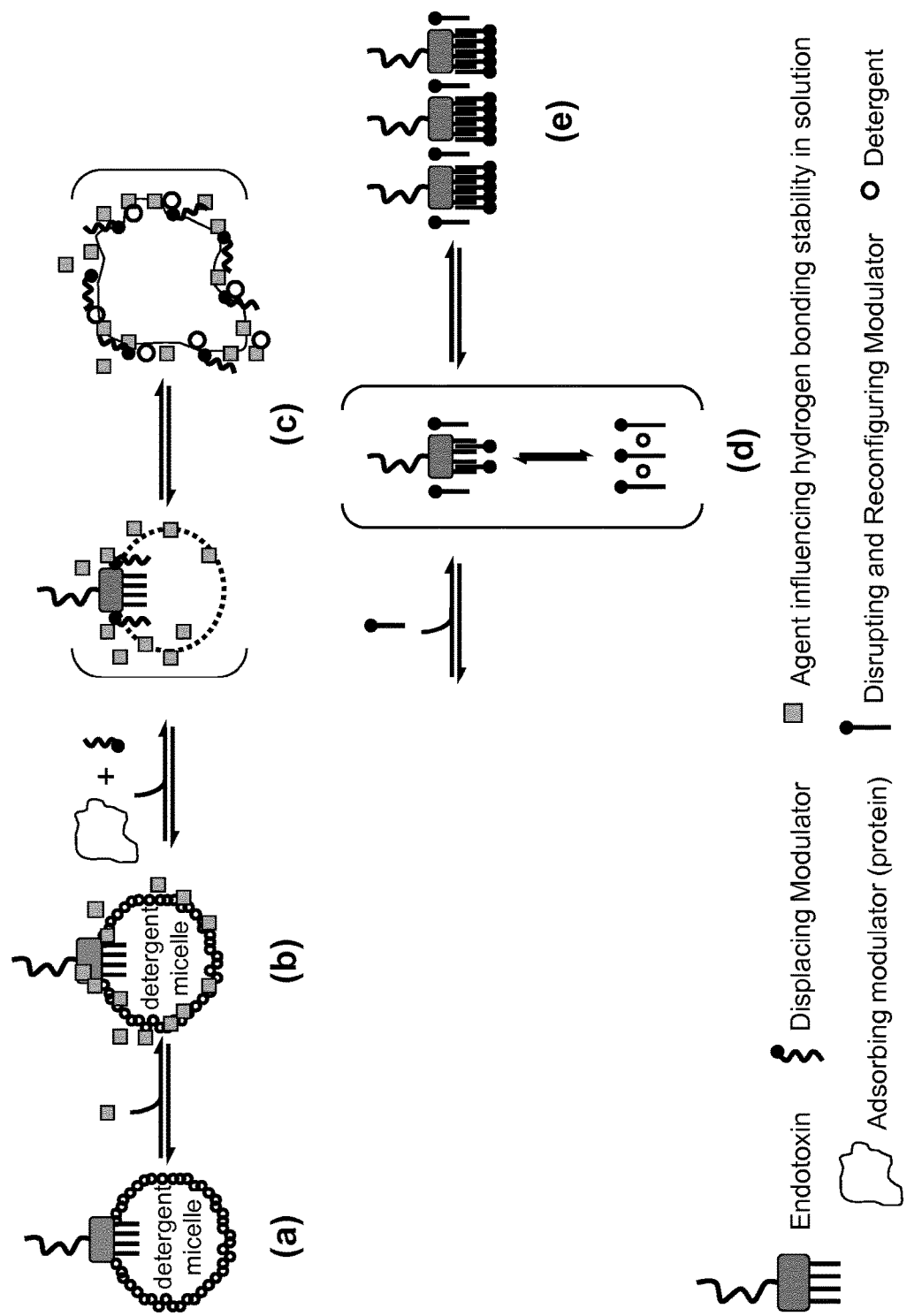
FIG. 3 illustrates a mechanism assumed to underlie the unmasking of endotoxin according to a further embodiment of the present invention. In the scenario depicted in FIG. 3, the endotoxin is present in solution with a detergent (capable of acting as an endotoxin masker), which forms detergent micelles in which endotoxin is embedded and thus masked from detection.

The conditions underlying the scenario shown in FIG. 3 are now different. Here, individual molecules of endotoxin are inserted in the lipid layer of detergent micelles (again symbolized by a ring of open circles representing the individual detergent molecules), but whether due to solution conditions, the nature of the interaction of the masking detergent with the endotoxin, or a combination of these things, the endotoxin inserted in the detergent micelle in panel (a) is more stable, and therefore less resistant to disruption with disrupting modulator, than either of the initial situations in FIGS. 1 and 2. Additional measures are required to destabilize the detergent-endotoxin complex so that, once destabilized, the modulator system can disrupt the micelle and liberate the inserted endotoxin.

To this end, the scenario shown in FIG. 3 entails using an agent which influences hydrogen bonding stability in solution, symbolized by small squares added above the equilibrium arrows between panels (a) and (b), and shown in their interaction with the micelle-endotoxin complex in panel (b). As mentioned above, one substance useful as an agent which influences hydrogen bonding stability in solution is divalent calcium.

With the complex between the detergent masker and the masked endotoxin thus destabilized, a modulator system comprising both an adsorbing modulator and a displacing modulator is added (see above equilibrium arrows between panels (b) and (c)) to displace the endotoxin from the already destabilized micelle of masking detergent. As mentioned above, the displacing modulator may be sodium-dodecyl sulfate (SDS), itself a detergent. The possibility that the modulator system contains a component which is itself a detergent and which may form new micelles of its own, is represented in panel (c) of FIG. 3 by a dotted circle, in which the endotoxin is inserted. Under the conditions prevailing in FIG. 3, however, any micelle formed by the displacing modulator is not as stable as the micelle formed by the masking detergent shown in panel (a). This is at least partly because the adsorbing modulator, e.g. BSA shown in FIG. 3 also binds the displacing modulator on its surface, establishing an equilibrium between protein-bound and micelle-forming populations of the displacing modulator which effectively destabilizes any micelle formed by the displacing modulator.

The presence of a disrupting and reconfiguring modulator, for instance a non-micelle-forming amphiphilic species such as 1-dodecanol, is shown over the equilibrium arrows between panels (c) and (d) of FIG. 3. The remainder of the schematic shown in FIG. 3 is analogous to what has already been discussed in detail above in the context of FIGS. 1 and 2. Briefly, the disrupting and reconfiguring modulator shown between panels (c) and (d) of FIG. 3 liberates and solubilizes endotoxin transiently inserted in micelles formed by the displacing modulator, at the same time establishing an equilibrium between solubilized (non-detectable) and aggregated (detectable) endotoxin species. This equilibrium may be shifted to the right (toward aggregated form) by the agent which influences hydrogen bonding stability in solution (e.g. a salt with a cation, preferably a divalent cation and/or a chaotropic agent).

Figure 4:
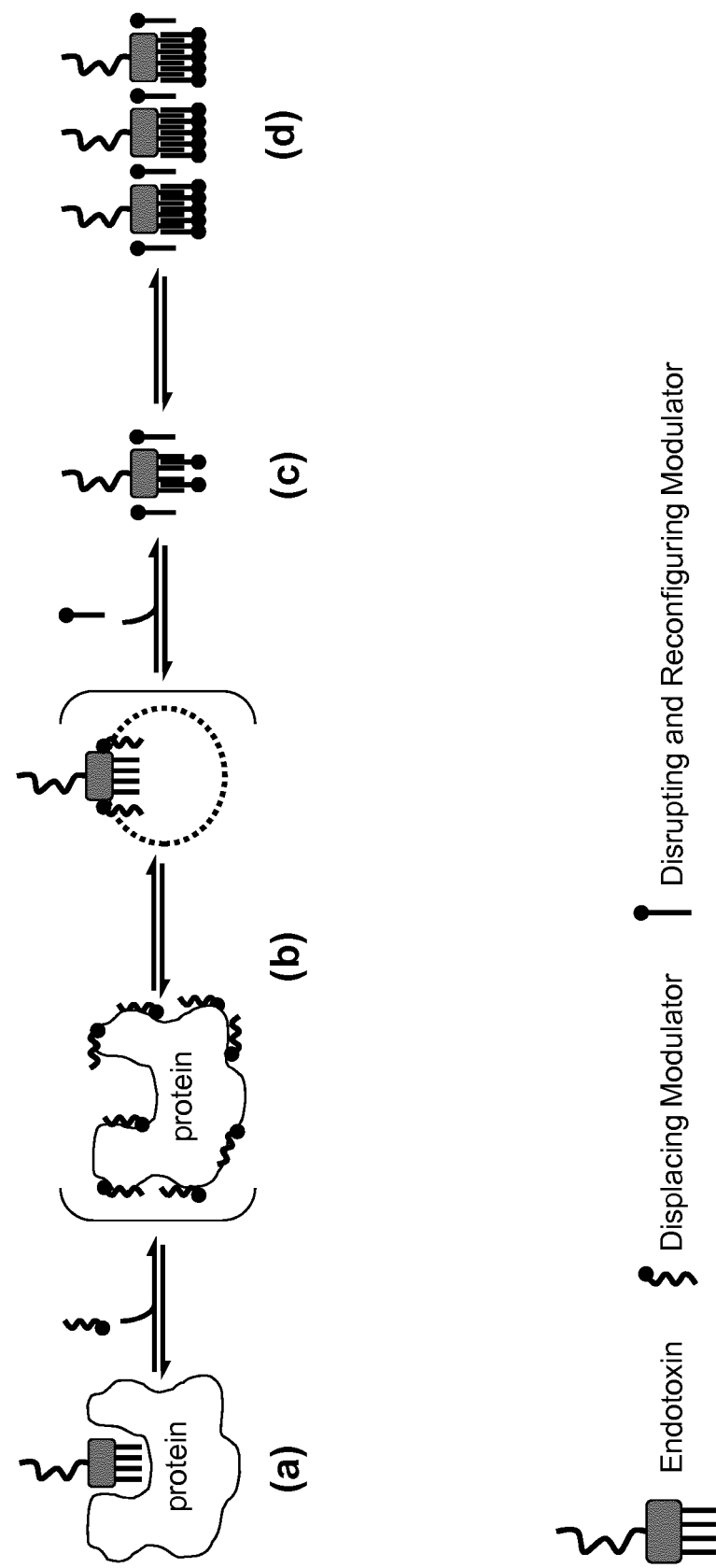
FIG. 4 illustrates a mechanism assumed to underlie the unmasking of endotoxin according to a further embodiment of the present invention. In the scenario depicted in FIG. 4, the endotoxin is present in solution, i.a. with a protein. The protein comprises a binding cleft in which endotoxin may stably bind and thus remain masked from detection.

Overall, FIG. 3 shows the liberation of a masked molecule of endotoxin from a stable complex with a micelle of a detergent masker. It uses an agent which influences hydrogen bonding stability in solution to destabilize this complex, and a multicomponent modulator which in total disrupts this complex and chaperones the liberated endotoxin through a series of energetic minima in the ultimate direction of an aggregated and therefore detectable complex of endotoxin.
Unmasking Endotoxin Masked by a Protein Masker with a Dual-Component Modulator Comprising a Displacing Modulator and a Disrupting and Reconfiguring Modulator FIG. 4 is a schematic depiction of a scenario in which an endotoxin is masked by a protein in solution. This is shown in panel (a) of FIG. 4. In the scenario depicted in FIG. 4, the protein, which may for example be an API in a pharmaceutical formulation, exhibits a binding cleft which is both sterically and electrostatically suitable to stably bind endotoxin. In this way, the protein masker binds molecules of endotoxin, rendering them undetectable. Addition of a modulator component, symbolized by the displacing modulator added above the equilibrium arrows between panels (a) and (b) of FIG. 4, displaces the endotoxin from its binding site on the protein masker. This displacing modulator might for instance be a "second heteroatom-substituted aliphatic comprising 8 to 16 carbon atoms" as discussed above. In the event that the displacing modulator would be e.g. sodium dodecyl sulfate, this displacing modulator might bind to the surface of the masking protein, displacing the molecule of endotoxin from its stable binding position within the protein's binding cleft. This is shown in the left portion of panel (b) of FIG. 4. In addition, as symbolized by the dotted circle in the right portion of panel (b), the displacing modulator component may also form transient micelles of its own, essentially chaperoning endotoxin liberated from the protein masker in a form stably inserted into the micelle's lipid layer. The exact position of the equilibrium shown in panel (b) of FIG. 4 depends on the effectiveness with which the displacing modulator binds to the surface of the masking protein (left portion of panel (b)), as well as the stability of the micelle formed (right portion of panel (b)).

Regardless of the exact position of this equilibrium, the important thing is that the displacing modulator depicted above the equilibrium arrows between panels (a) and (b) of FIG. 4 tends to liberate the endotoxin from its energetically stable binding position in or on the masking protein.

Once this endotoxin is freed from its masked state in or on the masking protein, a further modulator component (disrupting and reconfiguring modulator), depicted above the equilibrium arrows between panels (b) and (c) of FIG. 4 shifts the energetic relationships prevailing in solution such that the most stable state for endotoxin is in freely solubilized form, chaperoned in solution by the disrupting and reconfiguring modulator. This disrupting and reconfiguring modulator may for example be a "first heteroatom-substituted aliphatic comprising 8 to 16 carbon atoms" as discussed above, which may for example be 1-dodecanol. As discussed above, this disrupting and reconfiguring modulator will typically have the property of disrupting existing micelles (for example formed by the displacing modulator, and show in the right portion of panel (b)), while not forming micelles of its own. With any previous micelles of the displacing modulator thus disrupted, and with the disrupting and reconfiguring modulator unable to form corresponding micelles of its own, the most energetically stable form of the endotoxin becomes the solubilized form shown in panel (c) of FIG. 4, chaperoned by the disrupting and reconfiguring modulator.

The remainder of FIG. 4 is as previously discussed for the final equilibrium step in FIGS. 1 and 3. Briefly, there exists an equilibrium between individual, solubilized endotoxin (panel (c)) and aggregated endotoxin (panel (d)). To the extent that any appreciable population of aggregated endotoxin exists as part of this equilibrium, the endotoxin becomes detectable where, stably bound in or on the masking protein, it previously was not. Overall, endotoxin which was previously masked in individualized form by a protein has been unmasked and rendered detectable by adjusting the solution conditions such that the most energetically favorable state in which endotoxin can reside becomes its detectable aggregated form. As in previous figures discussed above, then, the "unmasking" is the result of manipulating solution conditions so as to shift equilibrium from a state in which endotoxin is stabilized in individualized form ("masked") toward a state in which endotoxin is aggregated and detectable ("unmasked").
Unmasking Endotoxin Masked by a Protein Using a Multi-Component Modulator Comprising an Adsorbing Modulator (Protein), a Displacing Modulator and a Disrupting/Reconfiguring Modulator, in Combination with an Agent which Influences Hydrogen Bonding Stability The initial scenario shown in FIG. 5 corresponds to that shown in FIG. 4: endotoxin is stably bound in or on a protein present in the composition. This protein in the composition, which may for example be an API, thus functions as an "endotoxin masker". As already discussed in the context of the scenario depicted in FIG. 3, the endotoxin is so stably complexed with the endotoxin masker in panel (a) of FIG. 5 that simple addition of modulator cannot alone liberate it. In FIG. 3, discussed above, the endotoxin masker was a detergent, which formed a micelle in which a single molecule of endotoxin was very stably inserted. Now in FIG. 5, the endotoxin masker is a protein with a binding site amenable for stable endotoxin binding. But the principle remains the same: Whether inserted in the lipid layer of a detergent micelle (FIG. 3) or residing stably in or on a protein, the endotoxin is stabilized to an extent that simple addition of a modulator is unable to overcome and the thus solubilized endotoxin remains undetectable.

As explained above for FIG. 3, this stable complex between endotoxin and endotoxin masker can be destabilized by addition of an agent which influences hydrogen bonding stability in solution, for example a salt or a chaotropic agent, for example divalent calcium. This agent which influences hydrogen bonding stability is symbolized in FIG. 5 by small squares starting over the equilibrium arrows between panels (a) and (b). This agent disrupts the hydrogen bonding network which is assumed to exist between endotoxin and the protein masker, thus raising the free energy of the complex to a level where the modulator components, which are shown above the equilibrium arrows between panels (b) and (c), can break up the complex to such an extent that the endotoxin is dislodged from the masking protein.

Figure 5:
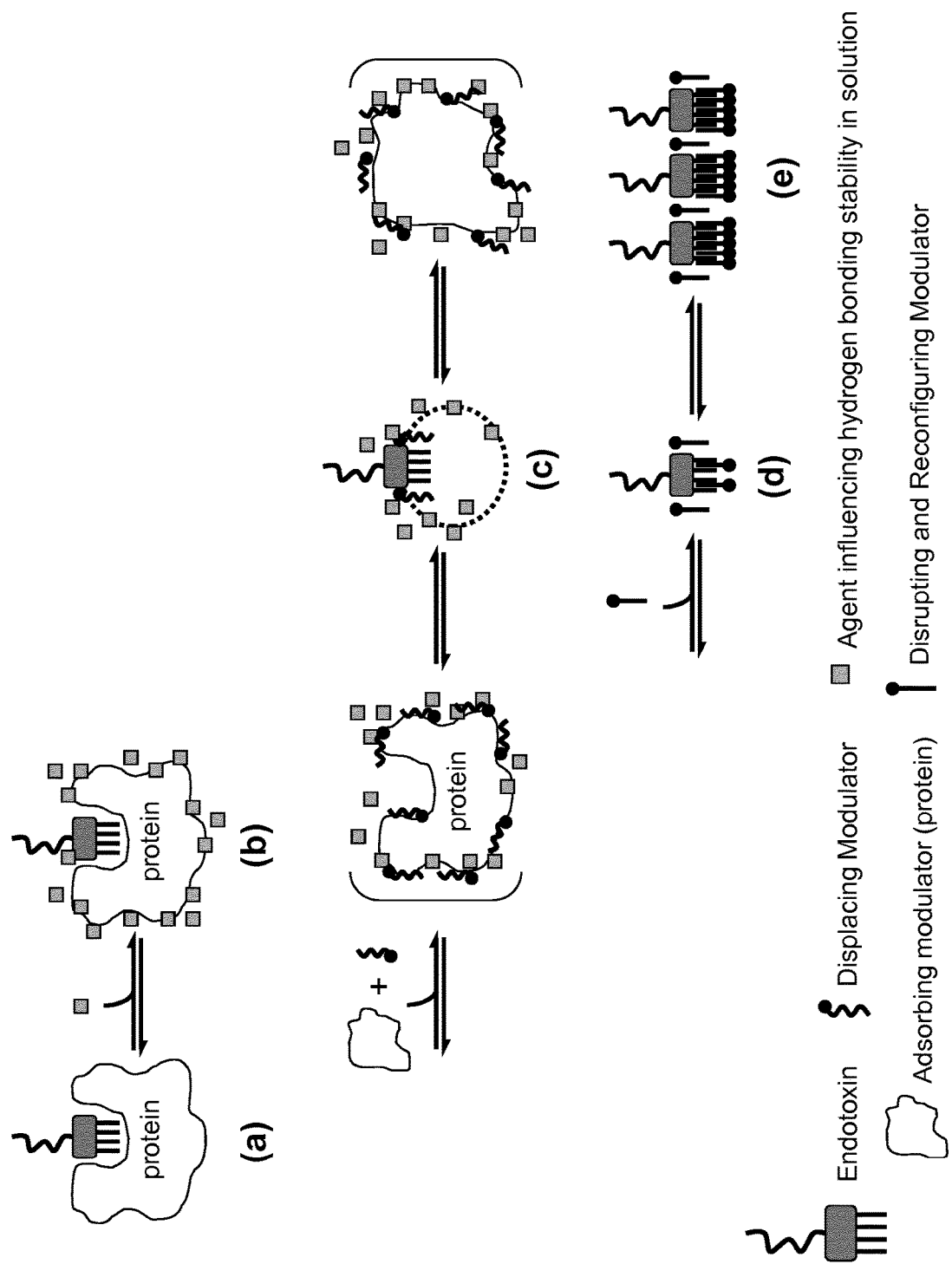
FIG. 5 illustrates a mechanism assumed to underlie the unmasking of endotoxin according to a further embodiment of the present invention. In the scenario depicted in FIG. 5, the endotoxin is present in solution with a protein (capable of acting as an endotoxin masker). The protein comprises a binding cleft in which endotoxin may stably bind and thus remain masked from detection.

Using a modulator system comprising both an adsorbing modulator (protein) and a displacing modulator as shown in FIG. 5 then is assumed to lead to the equilibrium situation shown in panel (c). In the left portion of panel (c) is the masking protein, now divested of the endotoxin previously bound. Molecules of the agent which influences hydrogen bonding stability in solution as well as of the displacing modulator, for example SDS, are shown bound to the surface of the masking protein, including in the binding site where endotoxin was previously bound. This depiction is intended to represent the fact that the displacing modulator effectively displaced endotoxin from its stable position in or on the masking protein. The middle portion of panel (c) of FIG. 5 shows a micelle which might be formed by the displacing modulator (e.g. SDS), with a molecule of endotoxin transiently inserted into the lipid layer of the micelle. Molecules of the agent which influences hydrogen bonding stability in solution are also shown bound to endotoxin and micelle, and serve to further destabilize this micelle, ensuring that the micelle in fact remains transient and does not present the endotoxin with an energy binding minimum from which it cannot be dislodged by a further disrupting modulator. Finally, the right portion of panel (c) shows the adsorbing modulator (protein) acting, as described briefly above, as a "molecular sponge" which adsorbs both the agent which influences hydrogen bonding stability in solution as well as the displacing modulator on its surface. This effectively depletes these species in solution, destabilizing the transient micelle shown in the middle portion of panel (c) to the extent that the displacing modulator is depleted, while stabilizing it to the extent that the agent which influences hydrogen bonding stability in solution is depleted. Generally, however, the amount of the agent which influences hydrogen bonding stability in solution will be high enough to destabilize the initial complex between masking protein and endotoxin that enough of this agent will persist in solution despite depletion by the adsorbing modulator, so that the transient micelle shown in panel (c) will be destabilized as desired.

Use of a disrupting and reconfiguring modulator, for example as shown over the equilibrium arrows between panels (c) and (d) of FIG. 5 (e.g. 1-dodecanol), will then break up the transient micelle shown in panel (c) so as to liberate the molecule of inserted endotoxin. As already discussed above the thus solubilized endototoxin (panel (d)) will then enter into an equilibrium relationship with a reconfigured, aggregated form of endotoxin (panel (e)) which can be detected as discussed above.

Figure 6:
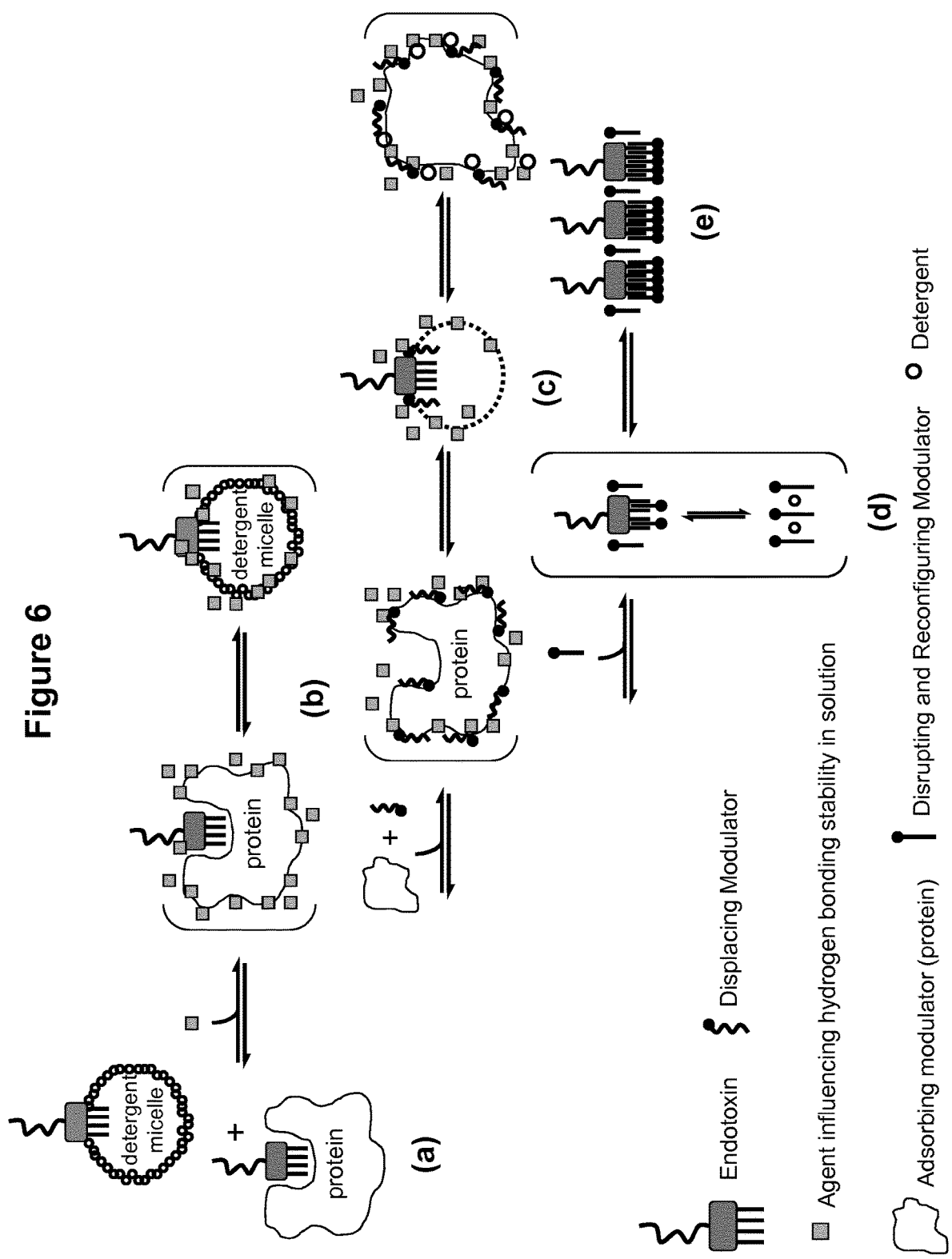
FIG. 6 illustrates a mechanism assumed to underlie the unmasking of endotoxin according to a further embodiment of the present invention. In the scenario depicted in FIG. 6, the endotoxin is present in solution with a protein as well as with a detergent (capable of acting as an endotoxin masker). The protein comprises a binding cleft in which endotoxin may stably bind and thus remain masked from detection. In addition, the detergent forms stable micelles in which molecules of endotoxin stably inserted are masked.

Unmasking Endotoxin Masked by Both Protein and Detergent Maskers with a Multi-Component Modulator Comprising an Adsorbing Modulator (Protein), a Displacing Modulator and a Disrupting/Reconfiguring Modulator, in Combination with an Agent which Influences Hydrogen Bonding Stability in Solution Many protein APIs, for example, antibodies, antibody fragments, hormones, enzymes, fusion proteins or protein conjugates are formulated and marketed at such high concentrations that detergents must be included in solution to avoid unwanted protein aggregation. The initial scenario shown in FIG. 6 is thus representative of one of the most relevant situations in the field of pharmaceutical formulation because both detergent and protein (e.g. API protein) maskers are present. The molecule of endotoxin is shown as inserted in the lipid layer of a detergent micelle (again symbolized by a ring of open circles representing the individual detergent molecules) as well as bound in or on the masking protein. In reality, these two species are likely to exist in equilibrium, with the relative position of this equilibrium, toward either a micelle- or a protein-bound species of endotoxin, being dictated by the relative stability of the respective complexes. All other things being equal, the complex of lower free energy, and therefore greater stability will generally prevail.

The discussion of FIG. 6 is analogous to that of FIG. 5 above, with the only difference being that panel (b) of FIG. 6 shows both the protein- and micelle-bound species of endotoxin in mutual equilibrium, each destabilized by the agent which influences hydrogen bonding stability in solution. Using an adsorbing modulator and a displacing modulator leads to the equilibrium situation depicted in panel (c) of FIG. 6. The discussion above for panel (c) of FIG. 5 applies here correspondingly. The use of a further disrupting and reconfiguring modulator (shown over the equilibrium arrows between panels (c) and (d)) which is capable of disrupting the transient micelle of panel (c) without forming micelles of its own, frees the endotoxin from its transiently bound state in a micelle of displacing modulator (middle portion of panel (c)), and engenders the equilibrium relationship between soluble (non-detectable) and aggregated (detectable) forms of endotoxin as discussed above. As explained above for previous figures, the disrupting and reconfiguring modulator shown in panel (d) is shown in equilibrium between states bound to the liberated endotoxin (upper portion of panel (d)) and detergent previously constituting the detergent micelle shown in panel (a) (lower portion of panel (d)).

It should be noted that the above scenarios are intended to illustrate the principles which the present inventors believe underlie the advantageous unmasking effect of the present invention in different situations. From the illustrative FIGS. 1-6, it will be clear that the processes discussed are all equilibrium processes, and that there is accordingly no prerequisite for the order of addition of different components of the modulator system or, if used, of the agent influencing hydrogen bonding stability and solution. The equilibria shown will thus be automatically established as soon as the components are present together in solution. The "order" of addition of these components as implied in the discussion above and shown in FIGS. 2-6 thus serves merely to illustrate the mechanisms which the present inventors believe underlie the advantageous technical effect of the present invention. Accordingly, unmasking a previously masked endotoxin might be accomplished by adding components at separate points in time as suggested by FIGS. 2-6, however the desired unmasking effect is also achievable when the components depicted in FIGS. 2-6 are added all at once.

In the most general sense, the scenarios depicted above in FIGS. 1-6 and the corresponding discussion should illustrate the following general principles, which are intended as general guidelines to the skilled person in implementing the present invention. Many solutions which test negative for endotoxin by conventional methods actually contain endotoxin in masked form. Conventional methods detect endotoxin in its aggregated form, so the fact that many existing solutions, such as pharmaceutical formulations, test negative for endotoxin does not necessarily mean that these solutions contain no endotoxin, but rather that they contain no endotoxin in detectable form.

In their most general form, the methods of the invention allow unmasking of endotoxin, e.g. by destabilizing complexes between endotoxin and endotoxin maskers so as to liberate, and ultimately aggregate individual molecules of endotoxin, thus rendering previously undetectable endotoxin detectable. Liberation of endotoxin from its masked complexes with endotoxin maskers may ensue directly using a disrupting and reconfiguring modulator to break up such complexes or, for especially stable complexes, these may be destabilized and then broken up with such a modulator or with a multi-component modulator system. However the bound endotoxin is liberated, the net effect is that endotoxin transitions from a stably bound form into a transient soluble form which may then aggregate. In its broadest sense, then, the methods of the present invention entail adjusting solution conditions as described above so as to usher previously masked endotoxin through a series of equilibria, wherein the final transition results in aggregation of endotoxin in a form which is detectable.

Since the unmasking and/or detection of endotoxin according to the methods described herein depend on a final reconfiguration of liberated endotoxin in solubilized (undetectable) form into aggregated form (detectable) a reconfiguring modulator will generally be needed. This reconfiguring modulator (e.g. 1-dodecanol) will generally have the characteristic of not forming micelles on its own, while stabilizing individual molecules of endotoxin such that these can enter into an equilibrium with aggregated forms of endotoxin. As is clear from the above, a reconfiguring modulator will sometimes, but need not necessarily, also function as a disrupting modulator which is able to break up an initial complex between endotoxin and a micelle of masking detergent and/or a complex of between endotoxin and a transient micelle of displacing modulator.

The following examples, including the experiments conducted and the results achieved, are provided for illustrative purposes only and are not construed as limiting the present invention.

EXAMPLES

Introduction

Endotoxin masking is a common phenomenon in pharmaceutical composition, especially biopharmaceutical drug products. Masking of endotoxin is driven by several factors, leading in the end to the non-detectability or at least a decreased detectability of the endotoxin in the drug product.

In one scenario, masking is not caused by the active pharmaceutical ingredient (API), e.g. protein, itself but by the formulation ingredients. Such ingredients are detergents, which are added to prevent aggregation of the protein, and buffer substances like citrate, phosphate, Tris, acetate, histidine, glycine which are added for pH-adjustment of the product.

Unsurprisingly, the kinetics of masking is influenced by temperature, with masking proceeding faster at higher temperatures than at lower temperatures. Unless otherwise specified, all experiments described below were performed at room temperature. This is the temperature at which production process steps of the active pharmaceutical ingredient (API) are often performed, and is therefore the most relevant temperature for assessing the applicability of the inventive methods described herein to industrial processes.

Example 1: Unmasking of Endotoxin from a Masking System of Polysorbate 20/Citrate Using a Disrupting and Reconfiguring Modulator (1-Dodecanol) Alone, and Together with a Further Adsorbing Modulator (BSA)

A masking system of polysorbate 20/citrate was chosen for the first experiment because citrate and polysorbate 20 are often included in biopharmaceutical formulations. These experiments are intended to determine whether masked endotoxin can be released from a complex with detergent masker by addition of a disrupting and reconfiguring modulator as described herein.

Materials and Methods

Endotoxin masking was performed as follows. 1 ml aqueous aliquots of 10 mM Citrate pH 7.5 containing 0.05% (w/v) of polysorbate 20 were prepared in endotoxin-free glass test tubes. Subsequently, 10 μl of a 10,000 EU/ml LPS stock solution (LPS 055 B5, Sigma L2637-5MG) were added, the resulting solution was vortexed for 1 min and was stored at room temperature for at least 24 hours. As a positive LPS control containing non-masked LPS, 10 μl of a 10,000 EU/ml LPS stock solution was added to 1 ml of endotoxin-free water, mixed and identically incubated as the masking preparations, but without polysorbate 20. The LPS-water positive control is described in more detail below.

Endotoxin unmasking was performed as follows. 100 μl of stock solutions of each of 1-dodecanol (disrupting and reconfiguring modulator) dissolved in 100% ethanol and 100 mg/ml BSA (adsorbing modulator) dissolved in endotoxin-free water were added. 1-dodecanol and BSA are used here as the two components of a dual-component modulator system. A separate unmasking experiment was performed identically as above, except that a single-component modulator was used. The single modulator in this experiment was 1-dodecanol alone, i.e. without BSA. Concentrations of the 1-dodecanol stock solutions were 400, 200, 100, 50, 25, 12.5 and 6.25 mM. For unmasking, the unmasking stock solutions of BSA and 1-dodecanol were sequentially added with 2 minutes mixing by vortexing after each addition. After mixing, the samples were incubated for 30 minutes at room temperature without mixing.

Endotoxin content was analyzed using EndoLISA® (Hyglos GmbH) according to the kit instructions. Sample dilutions were 1:10 and 1:100 in endotoxin-free water.

Endotoxin recovery was calculated as a percentage of recovery of a separate LPS-water control containing only water and LPS without any masking component. In the absence of any endotoxin masker, no LPS in this LPS.water control should be masked, that is all LPS present in this LPS-water control should be detectable. In this way, the LPS-water control serves as a standard to determine both qualitatively as well as quantitatively whether the EndoLISA® detection kit employed is functioning properly to detect LPS (qualitative control), and whether all LPS known to be present in the control is in fact detected (quantitative control).

Results

Figure 7:
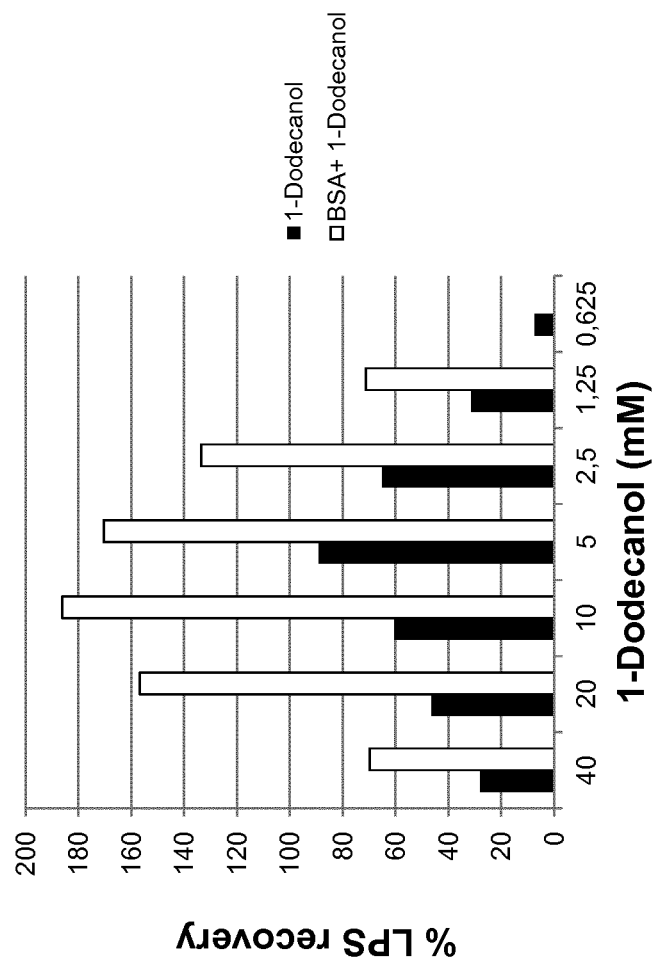
FIG. 7 is a graph showing the percent recovery of the endotoxin LPS from a detergent masker (polysorbate 20/citrate) using modulator systems of 1-dodecanol alone, and 1-dodecanol together with BSA.
Figure 8:
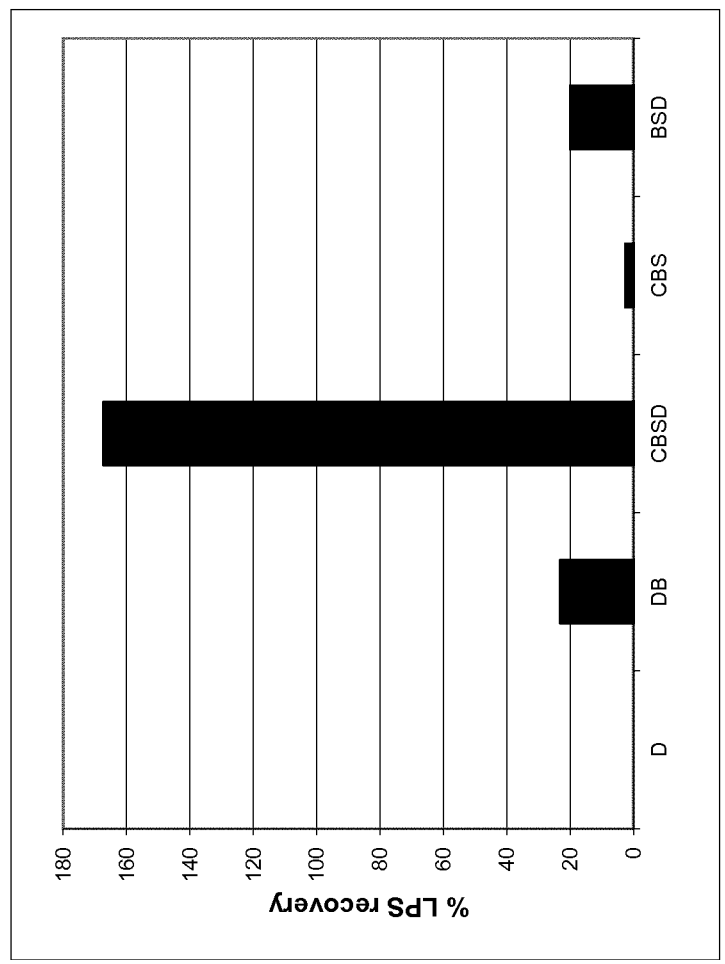
FIG. 8 is a graph showing the percent recovery of the endotoxin LPS from the detergent masker Triton X-100 using various modulator systems of various strengths.
Figure 9:
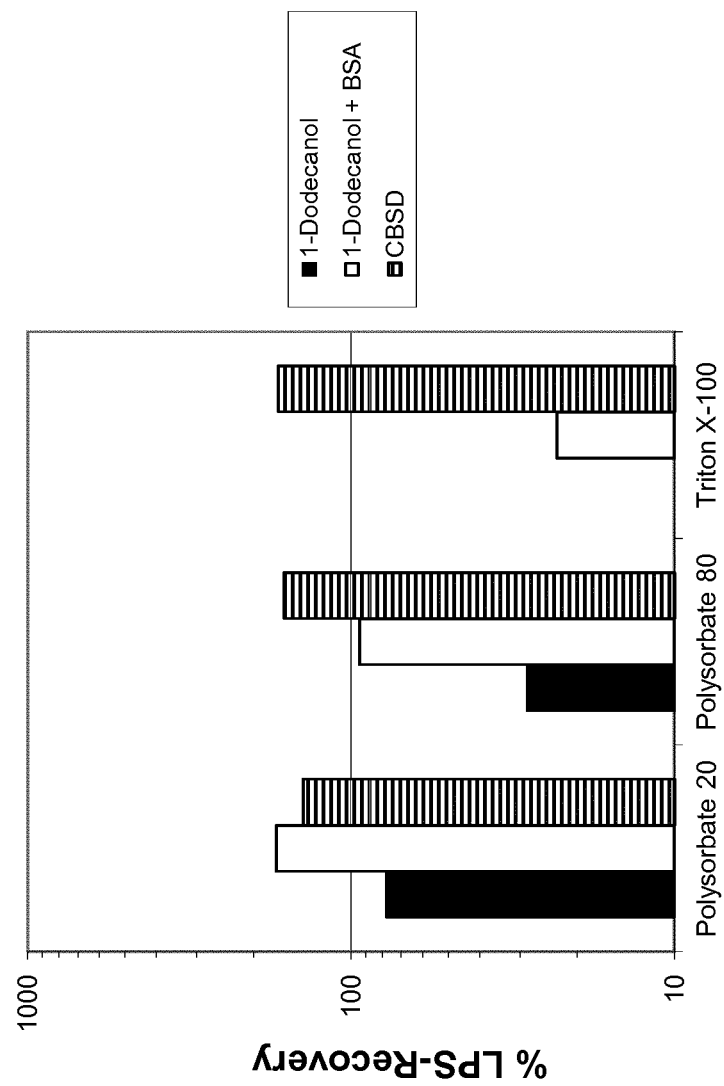
FIG. 9 is a graph showing the percent recovery of the endotoxin LPS from various detergent masking systems using a variety of modulator systems.

The recovery data in FIG. 7 and Table 1 (below) show that by the addition of BSA and/or 1-dodecanol in concentrations from 20 to 2.5 mM, masked endotoxin can be recovered to an extent greater than 100%. In the absence of BSA, 100% recovery cannot be achieved but, rather, greater than 50% in the range of 10 to 2.5 mM of 1-dodecanol with maximum recovery at 5 mM 1-dodecanol of approximately 90%.

In this and following examples, recoveries of greater than 100% of LPS should be interpreted in light of the following: The activity of LPS has been found to depend on both LPS form (e.g. extent and orientation of aggregation) as well as LPS structure (this structure varying slightly in LPS deriving from different bacterial species). The inventive unmasking methods described herein have the potential to alter both the form and the orientation of LPS aggregation (indeed, it is due to such alteration as promoted by the modulator, especially the reconfiguring modulator, that unmasking of LPS is possible at all). The change in form and orientation of LPS aggregation between the LPS-water control (not unmasked) and the unmasked samples may in some cases cause the activity detected following unmasking to exceed that measured in the positive LPS-water control. This does not mean that performing the inventive unmasking methods as described herein generates new LPS not previously present, but rather than in some cases, performing the inventive unmasking methods as described herein alter the form of existing LPS such that the apparent measured activity for a given amount of LPS increases.

TABLE 1

| 1-Dodecanol (mM) | BSA (mg/ml) | % LPS recovery |
| --- | --- | --- |
| 40 | — | 28 |
| 20 | — | 46 |
| 10 | — | 60 |
| 5 | — | 89 |
| 2.5 | — | 65 |
| 1.25 | — | 31 |
| 0.625 | — | 7 |
| 40 | 10 | 70 |
| 20 | 10 | 157 |
| 10 | 10 | 186 |
| 5 | 10 | 170 |
| 2.5 | 10 | 134 |
| 1.25 | 10 | 71 |
| 0.625 | 10 | 0 |

The results clearly demonstrate that masked endotoxin can be unmasked by the addition of the modulator 1-dodecanol (disrupting and reconfiguring modulator) alone. The results further show that this unmasking effect can be improved by the addition of a further adsorbing modulator (BSA). In this latter case in which 1-dodecanol and BSA are added as a dual-component modulator, the BSA helps to adsorb detergent, thus destabilizing the detergent micelle masking the endotoxin, the modulator 1-dodecanol, is capable of disrupting detergent micelles (in its capacity as disrupting modulator) and reconfiguring liberated endotoxin into an aggregate structure (in its capacity as reconfiguring modulator). In the case of polysorbate 20 in the absence of BSA an almost quantitative recovery is possible (89% at 5 mM 1-dodecanol). This may be due to the similarity in the length of the alkyl chains of 1-dodecanol and the LPS-masking detergent polysorbate 20. The unmasking is improved by the addition of BSA, which is assumed to shift the equilibrium of LPS from solubilized to aggregated form (see e.g. FIG. 2).

Example 2: Unmasking of Endotoxin from a Masking System of Polysorbate 20/Citrate Using Alcohols of Different Alkyl Chain Length as Disrupting and Reconfiguring Modulators This experiment investigates the use of various alkyl alcohols as disrupting and reconfiguring modulators. One aim of the experiments described in this example was to investigate the relationship between alkyl chain length in the alcohol and unmasking efficiency. To this end, unmasking was performed by the addition of alcohols with carbon atom chain lengths from C8-C18 in different concentrations.

Materials and Methods

Endotoxin masking was performed as described in Example 1. Unmasking was performed by the addition of stock solutions of unbranched 1-alcohols of different alkyl chain lengths ($C_8$, $C_{10}$, $C_{12}$, $C_{14}$, $C_{16}$, $C_{18}$) as modulators (disrupting and reconfiguring modulators) as described in Example 1 for 1-dodecanol (having a 12-carbon alkyl chain). Each of the stock solutions was dissolved in 100% ethanol. In contrast to certain of the experiments described above in Example 1, no other modulator components, e.g. BSA, were included in the present unmasking experiments. Analysis of endotoxin concentrations was performed using the EndoLISA® kit (Hyglos GmbH), and the subsequent calculation of endotoxin recovery was expressed as a percent of the LPS in the LPS-water control sample. The LPS-water positive control is explained in detail in Example 1, above.

Results

Table 2 (below) show the percentage of unmasked endotoxin as dependent on alcohol concentration and the length of the alkyl chain in the alcohol.

TABLE 2

| | % LPS Recovery | | | | | |
| --- | --- | --- | --- | --- | --- | --- |
| Conc. (mM) | 1-Octanol | 1-Decanol | 1-Dodecanol | 1-Tetradecanol | 1-Hexadecanol | 1-Octadecanol |
| 40 | 0 | 0 | 28 | 10 | nd | nd |
| 20 | 0 | 0 | 46 | 36 | 1 | 1 |
| 10 | 0 | 0 | 60 | 44 | 3 | 1 |
| 5 | 0 | 1 | 89 | 28 | 3 | 0 |
| 2.5 | 0 | 5 | 65 | 16 | 0 | 3 |
| 1.25 | 0 | 1 | 31 | 25 | 0 | 1 |
| 0.625 | 1 | 4 | 7 | 10 | 2 | 1 | nd = no data

Endotoxin recoveries of, i.e. unmasking endotoxin by, greater than 40% were achieved using 1-dodecanol and 1-tetradecanol. Recoveries using alcohols with alkyl chains lengths below or above C12 and C14 are below 10%.

The above results imply that the alkyl chain length of the alcohol used as a disrupting and reconfiguring modulator should ideally match the alkyl chain length of the acyl chains in the endotoxin as closely as possible. In the present case, the lengths of the acyl chains in the Lipid A component of LPS are C12 and C14, and it was the 1-alcohols having alkyl chain lengths in that range which, when used as disrupting and reconfiguring modulators, most effectively unmasked the endotoxin.

Example 3: Unmasking of Endotoxin from Masking Systems of Various Non-Ionic Surfactants Using 1-Dodecanol as a Disrupting and Reconfiguring Modulator Alone, and Together with the Adsorbing Modulator BSA To investigate the hypothesis that unmasking endotoxin from polysorbate 20 by 1-dodecanol alone is promoted by equivalent or similar alkyl chain length of the masking surfactant and 1-dodecanol, various experiments were designed using masking detergents of different chain lengths and different structure, and these were then unmasked using a disrupting and reconfiguring modulator of fixed alkyl chain length (1-dodecanol, with a $C_{12}$ alkyl chain). To this end, masked samples were prepared in polysorbate 80 and Triton X-100 and these were subsequently unmasked with 1-dodecanol or BSA/1-dodecanol using different concentrations of 1-dodecanol.

Materials and Methods

Endotoxin masking was performed as follows: 1 ml aliquots of 10 mM citrate pH 7.5 containing 0.05% of polysorbate 20, polysorbate 80 or Triton X-100 were prepared in endotoxin-free glass test tubes. Subsequently, 10 µl of a 10,000 EU/ml LPS stock solution (LPS 055 B5, Sigma L2637-5MG) were added, vortexed for 1 min and stored at room temperature for at least 24 hours. As a positive LPS control, 10 µl of a 10,000 EU/ml LPS stock solution was added to 1 ml of endotoxin-free water, mixed and identically incubated as the masking preparations. The positive LPS-water control is discussed in detail above in Example 1.

Unmasking was performed by the addition of stock solutions of 1-dodecanol (as a disrupting and reconfiguring modulator) in different concentrations as described in Example 1. Stock solutions of the respective alcohols were dissolved in 100% of ethanol. Unmasking was performed in both the absence and presence of 10 mg/ml BSA as described in Example 1.

Analysis of endotoxin concentrations was performed with the EndoLISA® kit (Hyglos GmbH), with subsequent calculation of recovery of endotoxin expressed as a percent of the endotoxin in the LPS/water control sample.

Results

Table 3 (below) shows the recoveries of LPS after unmasking from the respective polysorbate 20/citrate, polysorbate 80/citrate and Triton X-100/citrate masking systems as dependent on the 1-dodecanol (disrupting and reconfiguring modulator) concentration in the absence or presence of BSA (adsorbing modulator).

TABLE 3

| Dodecanol | BSA | % LPS recovery | | |
|---|---|---|---|---|
| (mM) | (mg/ml) | Polysorbate 20 | Polysorbate 80 | Triton X-100 |
| 40 | — | 28.0 | 4.9 | nd |
| 20 | — | 46.2 | 7.5 | 3.4 |
| 10 | — | 60.5 | 11.5 | nd |
| 5 | — | 89.1 | 25.2 | 0.0 |
| 2.5 | — | 64.9 | 28.5 | nd |
| 1.25 | — | 31.2 | 12.1 | 0.0 |
| 0.625 | — | 7.2 | 0.0 | nd |
| 0.313 | — | nd | nd | 0.0 |
| 40 | 10 | 69.7 | 19.4 | nd |
| 20 | 10 | 156.8 | 36.4 | 2.0 |
| 10 | 10 | 186.1 | 69.9 | nd |
| 5 | 10 | 170.5 | 86.9 | 23.0 |
| 2.5 | 10 | 133.5 | 94.2 | nd |
| 1.25 | 10 | 71.3 | 2.9 | 0.0 |
| 0.625 | 10 | 0.0 | 12.9 | nd |
| 0.313 | 10 | nd | nd | 0.0 | nd = no data

Unmasking with 1-dodecanol from the polysorbate 80/citrate masking system results in recovery of approximately 30% at an optimal concentration of 1-dodecanol of 2.5 mM. In the presence of BSA up to 90% can be recovered. Both unmasking approaches from the Triton X-100 masking system (i.e. with and without BSA) result in LPS recoveries below 20%, regardless of the concentration of 1-dodecanol.

Thus, unmasking using 1-dodecanol alone (as a disrupting and reconfiguring modulator) is sufficient to unmask LPS from masking systems such as in the polysorbate 20 masking system. The addition of BSA (as an adsorbing modulator) to adsorb the masking detergent improves unmasking recoveries in the polysorbate 20 and polysorbate 80 masking systems. Unmasking from the Triton X-100 system is not highly efficient even when BSA is added together with 1-dodecanol. Adding a further modulator component such as e.g. SDS (as a displacing modulator) can help improve recovery of LPS from Triton-X-100 masking formulations.

Example 4: Increasing Unmasking Efficiency by Addition of a Modulator and a Chaotropic Agent which Influences Hydrogen-Bonding Stability The weak recovery of LPS from the Triton X-100 masking system using the dual-modulator system of BSA (adsorbing modulator) and 1-dodecanol (disrupting and reconfiguring modulator) may be due to the high stability of the complex formed by Triton X-100 and LPS. This high stability may prevent the desired destruction of the endotoxin-masking micelles of Triton X-100 by the disrupting action of 1-dodecanol and adsorption of the detergent by BSA.

For this reason, the present experiments invertigate the possibility of destabilizing the masking complex by addition of a chaotropic salt together with a multi-component modulator. The hope was that by destabilizing an otherwise stable detergent micelle, destruction of this micelle using a multi-component modulator system of 1-dodecanol (as disrupting and reconfiguring modulator), BSA (as adsorbing modulator) and SDS (as displacing modulator) would then become possible.

Materials and Methods

Endotoxin masking was performed as follows: 1 ml aliquots of 10 mM citrate pH 7.5 containing 0.05% of Triton X-100 were prepared in endotoxin-free glass test tubes. Subsequently, 10 µl of a 10,000 EU/ml LPS stock solution (LPS 055 B5, Sigma L2637-5MG) were added, vortexed for 1 min and stored at room temperature for at least 24 hours. As a positive LPS control, 10 µl of a 10,000 EU/ml LPS stock solution was added to 1 ml of endotoxin free water, mixed and incubated in an identical manner as the masking preparations. The positive LPS-water control is discussed in detail above in Example 1.

Unmasking endotoxin was performed as follows: 100 µl of the following stock solutions were added as single component or as combinations to the 1 ml masked samples: 1 M $CaCl_2$ (dissolved in water), 100 mg/ml BSA (dissolved in water), 1% SDS (dissolved in water) and 50 mM 1-dodecanol (dissolved in 100% ethanol). In the case of addition of combinations, the agents were added sequentially, with a 2-minute vortexing step between each addition. The samples were then incubated at room temperature for 30 minutes without shaking.

Endotoxin content was analyzed using the EndoLISA® kit (Hyglos GmbH) according to the kit instructions. Sample dilutions were 1:10 and 1:100 in endotoxin-free water. Endotoxin recovery was calculated and expressed as a percentage of recovery of the LPS-water control. The positive LPS-water control is discussed in detail above in Example 1.

Results

FIG. 8 shows the percentage of LPS recovery as dependent on the addition of combinations of $CaCl_2$ (C), BSA (B; adsorbing modulator), SDS (S; displacing modulator) and 1-dodecanol (D; disrupting and reconfiguring modulator). 1-Dodecanol as the sole (disrupting and reconfiguring) modulator does not efficiently unmask LPS from a Triton X-100 masking complex. Addition of BSA (adsorbing modulator) and 1-dodecanol (disrupting and reconfiguring modulator) as a dual-component modulator system results in approximately 20% recovery. Further addition of either a chaotropic salt such as $CaCl_2$ or a further modulator such as SDS (displacing modulator) does not result in LPS recoveries greater than 20%. However, the addition of $CaCl_2$, BSA (adsorbing modulator), SDS (displacing modulator) and 1-dodecanol (disrupting and reconfiguring modulator) results in LPS recoveries of greater 100%.

Thus, additionally to BSA (adsorbing modulator) and 1-dodecanol (disrupting and reconfiguring modulator), a chaotropic salt and a further displacing modulator such as the detergent SDS help to break up the Triton X-100 masking complex. In this way, the combination of these 4 additives seems to break apart the masking complex and allows the formation of detectable LPS.

Example 5: Comparison of Different Unmasking Approaches from Various Masking Systems As efficient unmasking from the Triton X-100 masking system was observed using a combination of $CaCl_2$, BSA, SDS and 1-dodecanol, the question of unmasking efficiency of this approach starting from polysorbate masking systems remains. To answer this question, endotoxin was masked in polysorbate 20, 80 and Triton X-100/citrate masking systems and subsequently unmasked using 1-dodecanol alone; BSA and 1-dodecanol in combination; or $CaCl_2$, BSA, SDS and 1-dodecanol in combination. In these experiments, 1-dodecanol is used as a disrupting and reconfiguring modulator, BSA is used as an adsorbing modulator, SDS is used as a displacing modulator and $CaCl_2$ is used as an agent which influences hydrogen-bonding stability in solution.
Materials and Methods Endotoxin masking was performed as follows: 1 ml aliquots of 10 mM citrate pH 7.5 containing either 0.05% polysorbate 20, or 0.05% polysorbate 80 or 0.05% Triton X-100 were prepared in endotoxin-free glass test tubes. Subsequently, 10 µl of a 10,000 EU/ml LPS stock solution (LPS 055 B5, Sigma Aldrich L2637-5MG) were added, vortexed for 1 min and stored at room temperature for at least 24 hours. As a positive LPS control, 10 µl of a 10,000 EU/ml LPS stock solution were added to 1 ml of endotoxin-free water, mixed and identically incubated as the masking preparations. The function of the positive LPS-water control is as described above in Example 1.

Unmasking of endotoxin was performed as follows: Either 100 µl of a 50 mM 1-dodecanol stock solution; or 100 µl of 100 mg/ml BSA and 100 µl of a 50 mM 1-dodecanol stock solution; or 100 µl of a 1 M $CaCl_2$ solution, 100 ml of a 100 mg/ml BSA solution, 100 µl of a 1% SDS solution and 100 µl of a 50 mM 1-dodecanol solution were added to the solution containing masked LPS. In the case of addition of combinations, the agents were added sequentially with a 2-minute vortexing step between each addition. The samples were then incubated at room temperature for 30 minutes without shaking.

Endotoxin content was analyzed using the EndoLISA® kit (Hyglos GmbH) according to the kit instructions. Sample dilutions were 1:10 and 1:100 in endotoxin-free water. Endotoxin recovery was calculated as a percentage of recovery of the LPS-water control.

Results

Table 4 (below) and FIG. 9 show the percentages of LPS recovery using either 1-dodecanol alone; BSA and 1-dodecanol in combination; or $CaCl_2$, BSA, SDS and 1-dodecanol in combination (CBSD) for unmasking from various detergent masking systems.

TABLE 4

| | % LPS recovery | | |
|---|---|---|---|
| Masking detergent | 1-dodecanol | BSA/1-dodecanol | CBSD |
| Polysorbate 20 | 78 | 170 | 141 |
| Polysorbate 80 | 28 | 94 | 161 |
| Triton X-100 | 0 | 23 | 168 |

Efficient (~80%) unmasking from the polysorbate 20 masking system is achieved by 1-dodecanol, BSA/1-dodecanol and $CaCl_2$/BSA/SDS/1-dodecanol. In the case of a polysorbate 80 masking system, good unmasking efficiency is achieved in the presence of BSA/1-dodecanol and $CaCl_2$/BSA/SDS/1-dodecanol. In the case of a Triton X-100 masking system, the addition of $CaCl_2$/BSA/SDS/1-dodecanol results in good LPS recovery.

Thus, dependent on the stability of the masking complex, efficient endotoxin recoveries can be achieved using different unmasking approaches. However, the unmasking approach involving the combination of $CaCl_2$, BSA, SDS and 1-dodecanol may be the most universal method, due to its ability to achieve efficient unmasking, regardless of the masking system used. As is clear from the experiments described herein above, an optimal composition for unmasking LPS in any given formulation can be easily achieved by routine experimentation.

Example 6: Unmasking of Endotoxin from Different Endotoxin Sources

Endotoxin unmasking experiments in Examples 1-5 were performed with a commercially available, highly purified LPS preparation of *E. coli* O55:B5. As only the conserved Lipid A part of LPS is responsible for toxicity and for detectability in Factor C-based detection methods, it can be assumed that the unmasking approaches described above will work equally well using LPS preparations from bacteria other than *E. coli* O55:B5. However, the literature also describes differences in acyl chain length for the lipid A part of LPS, as well as modifications of side chains. Even more, the length of the O-sugar side chains of LPS could potentially impact the unmasking approach. Furthermore, it cannot be excluded that purified LPS and naturally occurring endotoxin (NOE) may differ in their unmasking behavior. To address these issues, and exclude the possibility, that the unmasking approaches are specific for the used LPS of *E. coli* O55:B5, LPS from different bacteria, different length in core- and O-sugar chains and different purity were masked in various detergent masking systems and subsequently unmasked using either 1-dodecanol alone, BSA/1-dodecanol or $CaCl_2$/BSA/SDS/1-dodecanol.

Materials and Methods

Masking of endotoxin was performed as follows: LPS samples of different types and from different sources were (approximately 50 EU/mL) added to 1 ml masking samples containing either 0.05% polysorbate 20, 0.05% polysorbate 80 or 0.05% Triton X-100 and 10 mM citrate pH 7.5. LPS source, type and the supplier are shown in Table 5 (below). NOEs were produced from bacterial culture supernatant after growth to stationary phase in LB media by sterile filtration. As a preservative, 0.05% sodium azide was added.

Lyophilized LPS was dissolved in endotoxin-free water. LPS solutions for which the supplier in Tables 5-7 is indicated as "LMU" were kind gifts of Dr. A. Wieser of the Ludwig-Maximilian University of Munich. Endotoxin content of the LPS stock solutions was determined using the EndoZyme® kit (Hyglos GmbH) and stock solutions of approx. 5000 EU/ml LPS in endotoxin-free water were produced. From these solutions 10 µl were added to 1 ml masking samples. Afterwards, the samples were allowed to mask the respective LPS for 7 days at room temperature.

Unmasking of endotoxin was performed by addition of 100 µl of either a 100 mM 1-dodecanol stock solution, or addition of 100 µl of a 100 mg/ml BSA and 100 µl of 100 mM 1-dodecanol stock solution or by addition of 100 µl of each of 1 M CaCl2, 100 mg/ml BSA, 1% SDS and 100 mM 1-Dodecanol solutions. Unmasking and determination of endotoxin content were performed as described in Examples 1-5.

Results

Tables 5-7 (below) show the percent of LPS recovery after masking and after unmasking of LPS from different sources and types out of different detergent masking systems. Specifically, Table 5 shows the results obtained for a masking system of Tween20/Citrate; Table 6 shows the results obtained for a masking system of Tween80/Citrate; and Table 7 shows the results obtained for a masking system of Triton X-100/Citrate.

TABLE 5

Tween 20/Citrate masking system

| | supplier | Masking control (% recovery) | Dodecanol (% recovery) | BSA/Dodecanol (% recovery) | CaCl$_2$/BSA/SDS/Dodecanol (% recovery) |
|---|---|---|---|---|---|
| *Klebsiella pneumonia* | LMU | 0.0 | 66 | 128 | 212 |
| *Morganella morganii* | LMU | 0.0 | 81 | 110 | 120 |
| *Yersinia enterocolitica* | LMU | 0.0 | 63 | 174 | 243 |
| *Serratia marcescens* | LMU | 0.0 | 128 | 168 | 182 |
| *Neisseria meningitis* | LMU | 0.0 | 9 | 23 | 38 |
| *Acinetobacter baumanni* * | LMU | 0.0 | 0 | 124 | 655 |
| *Enterobacter cloacae* (NOE) * | Hyglos | 0.0 | 55 | 156 | 187 |
| *Salmonella enterica* | Sigma | 0.0 | 42 | 63 | 76 |
| *E. coli* K 12 | Invivogen | 3.0 | 78 | 80 | 137 |
| *Pseudomonas aeruginosa* * | Sigma | 0.0 | 14 | 5 | 179 |

* Strains which are common water contaminants, and therefore more likely to be present in processes for the production of pharmaceutical compositions

TABLE 6

Tween 80/Citrate masking system

| | supplier | Masking control (% recovery) | Dodecanol (% recovery) | BSA/Dodecanol (% recovery) | CaCl$_2$/BSA/SDS/Dodecanol (% recovery) |
|---|---|---|---|---|---|
| *Klebsiella pneumonia* | LMU | 0.0 | 12 | 173 | 353 |
| *Morganella morganii* | LMU | 15.0 | 15 | 39 | 99 |
| *Yersinia enterocolitica* | LMU | 7.0 | 22 | 168 | 309 |
| *Serratia marcescens* | LMU | 0.0 | 105 | 199 | 326 |
| *Neisseria meningitis* | LMU | 0.0 | 0 | 11 | 42 |
| *Acinetobacter baumanni* * | LMU | 0.0 | 7 | 337 | 511 |
| *Enterobacter cloacae* (NOE) * | Hyglos | 24.2 | 27 | 74 | 183 |
| *Pseudomonas aeruginosa* * | Sigma | 1.0 | 1 | 1 | 90 |
| *Salmonella enterica* | Sigma | 0.0 | 18 | 10 | 69 |
| *E. coli* K 12 | Invivogen | 1.9 | 85 | 106 | 176 |

* Strains which are common water contaminants, and therefore more likely to be present in processes for the production of pharmaceutical compositions

TABLE 7

Triton X-100/Citrate masking system

| | supplier | Masking control (% recovery) | Dodecanol (% recovery) | BSA/Dodecanol (% recovery) | CaCl₂/BSA/SDS/ Dodecanol (% recovery) |
|---|---|---|---|---|---|
| *Klebsiella pneumonia* | LMU | 9.8 | 22 | 12 | 162 |
| *Morganella morganii* | LMU | 5.5 | 35 | 23 | 48 |
| *Yersinia enterocolitica* | LMU | 0.0 | 13 | 19 | 236 |
| *Serratia marcescens* | LMU | 3.5 | 28 | 20 | 80 |
| *Neisseria meningitis* | LMU | 0.0 | 55 | 14 | 161 |
| *Acinetobacter baumanni* * | LMU | 7.8 | 0 | 57 | 918 |
| *Enterobacter cloacae* (NOE) * | Hyglos | 0.0 | 2 | 26 | 85 |
| *Pseudomonas aeruginosa* * | Sigma | 0.0 | 1 | 11 | 25 |
| *Salmonella enterica* | Sigma | 0.0 | 21 | 12 | 234 |

* Strains which are common water contaminants, and therefore more likely to be present in processes for the production of pharmaceutical compositions The above data clearly show that the ability to successfully unmask endotoxin from various masking systems is independent of the source and type of LPS used. These results are important because they show that the unmasking methods of the present invention represent a general teaching applicable to various types of endotoxin from various sources, under a variety of masking conditions.

Example 7: Unmasking of Endotoxin from Protein Masking Systems

The previous experiments have investigated the unmasking of LPS from detergent masking systems. However, as described herein above, detergents are not the only substances which can mask endotoxin from detection. Proteins (e.g. protein APIs) are also capable of masking endotoxin from detection when they contain binding sites on or within their structure in which endotoxin can bind, thus evading detection. The present experiments therefore relate to the masking of endotoxin (LPS) by a protein rather than a detergent. Lysozyme was used as the masking protein in these experiments because its ability to bind endotoxin is known (see e.g. Ohno & Morrison (1999). J. Biol. Chemistry 264(8), 4434-4441).

Materials and Methods

Endotoxin masking was performed as follows: 50 EU/ml of LPS (*E. coli* O55:65) was incubated for seven days in 10 mM citrate buffer, pH 7.5 containing 1 mg/ml hen egg white lysozyme (Sigma Aldrich) at room temperature.

Endotoxin unmasking was performed as follows: Unmasking was performed by addition of unmasking reagents (modulators as described in previous examples and agents influencing hydrogen bonding stability) in various combinations. Specifically, 100 µl of the following unmasking agents were added to 1 ml aliquots of the masked samples: 1-dodecanol, CaCl₂, BSA, SDS. All stock solutions were dissolved in water except 1-dodecanol, which was dissolved in 100% ethanol. The added concentrations of the stock solutions were 100 mM 1 M CaCl₂, 100 mg/ml BSA and 1% SDS, respectively. Unmasking was performed by sequential addition of the various components with a two-minute vortexing step after each addition. The samples were then incubated for 30 minutes at room temperature and subsequently diluted 1:10 and 1:100 in endotoxin-free water for analysis using the EndoLISA® kit (Hyglos GmbH).

Results

Table 8 (below) shows the efficiency unmasking from a protein masker (lysozyme) as dependent on the added components.

TABLE 8

| CaCl2 | BSA | SDS | 1-dodecanol | % recovery LPS |
|---|---|---|---|---|
| − | − | − | − | 0 |
| + | − | − | − | 0 |
| + | + | − | − | 4 |
| + | + | + | − | 33 |
| + | + | + | + | 115 |
| + | + | − | + | 15 |
| + | − | + | + | 0 |
| + | − | + | − | 4 |
| + | − | − | + | 2 |
| − | + | − | − | 9 |
| − | + | + | − | 0 |
| − | + | + | + | 1 |
| − | + | − | + | 6 |
| − | − | + | − | 0 |
| − | − | + | + | 0 |
| − | − | − | + | 1 |

In the case of masking by lysozyme, use of 1-dodecanol (reconfiguring modulator) alone or together with a supporting detergent (displacing modulator) as a further component of the modulator system does not efficiently unmask. Here, the lysozyme-LPS masking complex seems to be more stable due to electrostatic interactions between the negatively charged LPS and the positively charged lysozyme. Improvement of unmasking may be achieved by the addition of salt, which disrupts the electrostatic interaction, thus rendering the lysozyme-LPS complex more labile and increasing its susceptibility to disruption with modulator. To this end, good results may be achieved by using a multi-component modulator system of BSA (adsorbing modulator), SDS (displacing modulator) and 1-dodecanol (reconfiguring modulator), together with CaCl₂ to lower the stability of the initial lysozyme-LPS complex. The combination of these components is able to break up the masking complex and lead to detectable LPS structures. This model may be taken as a general model of the measures which may be used to unmask endotoxin when it is masked, in whole or in part, by a protein, e.g. a protein API in a pharmaceutical composition.

Example 8: Substances Other than 1-Alkyl Alcohols as Modulators for Unmasking

As described herein above, 1-alkyl alcohols (used as reconfiguring modulators) have been found to promote the formation of detectable LPS structures. It was therefore desired to investigate whether other types of substances than 1-alkyl alcohols might also have the ability to promote similarly detectable forms of LPS. This example shows the results of a screening for substances other than 1-alkyl-alcohols which might be able to support formation of detectable LPS structures.

Materials and Methods

LPS (*E. coli* O55:65, Sigma) 100 EU/ml was masked in polysorbate 20/citrate for 24 hours at room temperature. Unmasking was initiated by sequential addition of 1 part stock solutions of $CaCl_2$ (at 1 M), BSA (at 100 mg/mL), SDS (at 1%) and substance X into 10 parts of a solution of masked LPS, wherein "substance X" represented the substance other than a 1-alkyl alcohol, the ability of which as a reconfiguring modulator was to be tested. Substance X was titrated in different concentrations. After unmasking, samples were diluted 1:10 and 1:100 in endotoxin-free water and analyzed for detectable endotoxin using the EndoLISA® kit (Hyglos GmbH).

Results

Table 9 (below) shows the maximum LPS recoveries after unmasking as dependent on the substance used as modulator. Furthermore, suitable concentrations of stock solutions of the respective substances for unmasking are shown.

TABLE 9

| Substances | % LPS recovery | Optimum stock concentration of substance X |
|---|---|---|
| sodium octyl sulfate (SOS) | 20 | 30 mM |
| 1-decanoic acid | 57 | 100 mM |

As can be seen from the above, 1-alkyl alcohols are not the only class of compounds which may function as a reconfiguring modulator to promote the formation of a detectable form of LPS. Other substances containing higher oxidation states of oxygen (e.g. as in 1-decanoic acid) as well as other heteroatoms than oxygen (e.g. as in sodium octyl sulfate (SOS)) may also enable moderate to good unmasking.

The results indicate that substances which are similar in structure to 1-alkylalcohols are also able to support unmasking to a certain extent. It appears that OH-derivatives of alkanes, preferably $C_8$-$C_{16}$ alkanes, preferably $C_8$-$C_{12}$ alkanes, preferably $C_{12}$ alkanes serve best to render LPS susceptible to detection by Factor C-based assays.

Example 9: Unmasking Using Albumins from Different Sources and 1-Dodecanol

As part of the verification of the improvement in unmasking by the addition of bovine serum albumin (BSA) in masked samples containing polysorbate 80, albumins from different sources were tested.

Materials and Methods

Masked samples (1 ml) containing 50 EU/ml of LPS (055:65) in polysorbate 80/citrate buffer were unmasked by the addition of 100 µl of stock solutions with different concentrations of albumins (bovine serum albumin (BSA), very low endotoxin, Serva GmbH; human serum albumin (HSA, recombinantly produced in *Pichia pastoris* (Sigma Aldrich); and Ovalbumin (Ova), EndoGrade Ovalbumin, Hyglos GmbH) and subsequent addition of 100 µl of a 100 mM 1-dodecanol stock solution). Concentrations of albumin stock solutions were 100, 33, 10, 3.3 and 1 mg/ml. Due to the lower solubility of ovalbumin in water, a 100 mg/ml solution of ovalbumin was not prepared.

LPS recoveries were calculated following determination of detectable LPS content using the EndoLISA® kit (Hyglos GmbH). For EndoLISA® measurements the unmasked samples were 1:10 and 1:100 diluted in endotoxin-free water and subsequently measured according to the kit instructions.

Results

Table 10 (below) shows the unmasking efficiency from a polysorbate 80/citrate masking system, as dependent on albumins from different sources.

TABLE 10

| protein | [stock solution] (mg/ml) | % LPS recovery |
|---|---|---|
| BSA | 100 | 66.0 |
| | 33 | 46.2 |
| | 10 | 38.1 |
| | 3.3 | 28.2 |
| | 1 | 30.9 |
| HSA | 100 | 42.3 |
| | 33 | 94.5 |
| | 10 | 151.6 |
| | 3.3 | 40.4 |
| | 1 | 34.3 |
| ovalbumin | — | nd |
| | 33 | 79.4 |
| | 10 | 59.0 |
| | 3.3 | 33.0 |
| | 1 | 19.6 | nd = no data

The data show that all albumins tested are able to support unmasking from a polysorbate 80 masking system. Suitable final concentrations in the unmasked samples are 10 mg/ml for BSA, 1 mg/ml for HSA and 3.3 mg/ml for ovalbumin. The differences in optimum concentrations may result from different affinities of the albumins to the detergent in the masked sample.

Example 10: The Effect of Various Chaotropic Salts on Unmasking Efficiency

Unmasking using the combination of substances $CaCl_2$ (agent influencing hydrogen bonding), BSA (adsorbing modulator), SDS (displacing modulator) and 1-dodecanol (reconfiguring modulator) (this entire combination is referred to as "CBSD") has been shown above to efficiently unmask LPS when masked by e.g. Triton X-100. The present experiments investigate the effect of the nature of the chaotropic salt (agent influencing hydrogen bonding stability) on unmasking efficiency. To this end, the following experiments employ salts of increasing chaotropic properties: $Na^+$, $Mg^{2+}$ and $Ca^{2+}$, in each case presented as the corresponding chloride salt.

Materials and Methods Endotoxin masking was performed as follows: 50 EU/ml of E. coli LPS O55:65 was masked by allowing it to incubate for 3 days at room temperature in a 10 mM citrate buffer solution (pH 7.5) containing 0.05% Triton X-100. Here, Triton X-100 functioned as the detergent masker.

Unmasking of endotoxin was performed as follows: 300, 100, 30, 10, 3 and 1 μl of either a 5 M sodium chloride (NaCl), 1 M magnesium chloride ($MgCl_2$) or 1 M calcium chloride ($CaCl_2$) stock solution were added to 1 ml aliquots of the masked samples and mixed. Subsequently, 100 μl of the other modulator components (BSA (adsorbing modulator), SDS (disrupting and displacing modulator) and 1-dodecanol (reconfiguring modulator)) were added as described in Examples 1-5.

Results

Table 11 (below) shows the percentage of endotoxin recovery as dependent on each chaotropic salt and the most suitable final concentration of each salt in the unmasked sample.

TABLE 11

| salt | LPS recovery % | Concentration (mM) |
|---|---|---|
| NaCl | 96.7 | 357 |
| $MgCl_2$ | 139.8 | 188 |
| $CaCl_2$ | 142.5 | 72 |

The data show that all the salts tested were able to support efficient unmasking of LPS from the masking detergent Triton X-100 in combination with a multicomponent modulator system including BSA (as adsorbing modulator), SDS (here, as disrupting modulator) and 1-dodecanol (as disrupting and reconfiguring modulator). Furthermore, as described herein above, the amount of the salt required to achieve a comparable degree of unmasking efficiency decreased with increasing chaotropic properties. These results allow several general conclusions to be drawn. First, when using a salt to destabilize a masked complex between endotoxin and endotoxin masker, the chaotropic character of this salt is an important factor in achieving efficient unmasking. Second, the amount of salt required to achieve efficient unmasking will generally vary inversely with the chaotropic strength of the salt employed.

Example 11: Unmasking of Endotoxin from Samples Containing Detergent and Phosphate Buffer Most formulations of drugs which contain a protein (e.g. antibody) as an active pharmaceutical ingredient (API) contain either non-ionic detergents like polysorbate 20 or 80 together buffered in either citrate or phosphate. In such formulations, the detergent concentration is usually above the respective detergent's critical micellar concentration (CMC). Furthermore pH-values of such formulations are often adjusted in order to ensure optimum stability of the API.

With the above in mind, the investigations set out in this Example sought to investigate the influence of pH value on unmasking efficiency. In order to approximate the conditions prevailing in pharmaceutical formulations containing a protein API as closely as possible, the detergents polysorbate 20 and polysorbate 80 were used as endotoxin maskers, and the solutions were phosphate-buffered. In view of the results described herein above, unmasking was performed using a combination of $CaCl_2$ (chaotropic salt as an agent which influences hydrogen bonding stability), BSA (adsorbing modulator), SDS (here, as disrupting modulator) and 1-dodecanol (disrupting and reconfiguring modulator). As $Ca^{2+}$ and $PO_4^{3-}$ form non-soluble calcium-phosphate complexes, the calcium chloride solution was stabilized by addition of a two-fold molar excess of citrate, pH 7.5.

Materials and Methods

Masking of endotoxin was performed as follows: To 1 ml samples, each containing 10 mM of phosphate buffer of various pH-values and either 0.05% polysorbate 20 or polysorbate 80, were added 100 EU/ml of E. coli LPS O55:65. Masking was allowed to proceed by incubating these solutions for 7 days at room temperature. LPS-containing control samples of phosphate buffers lacking detergent were prepared, incubated and measured in parallel to the masking samples.

Unmasking of endotoxin was performed as follows: A combination of $CaCl_2$, BSA, SDS and 1-dodecanol was added to each of the samples as described in previous examples. To avoid calcium phosphate precipitation and to adjust the pH of the samples, a two-fold molar excess of citrate buffer pH 7.5 was added to each sample before addition of the unmasking components.

Endotoxin content of the masked samples was determined using the EndoZyme® kit of Hyglos GmbH at time zero, and after 7 days. Endotoxin content of the unmasked samples was analyzed using the EndoLISA® kit of Hyglos GmbH. The percentage of LPS recovery after 7 days of masking and after unmasking was calculated in reference to control samples at time zero.

Results

Figure 10:
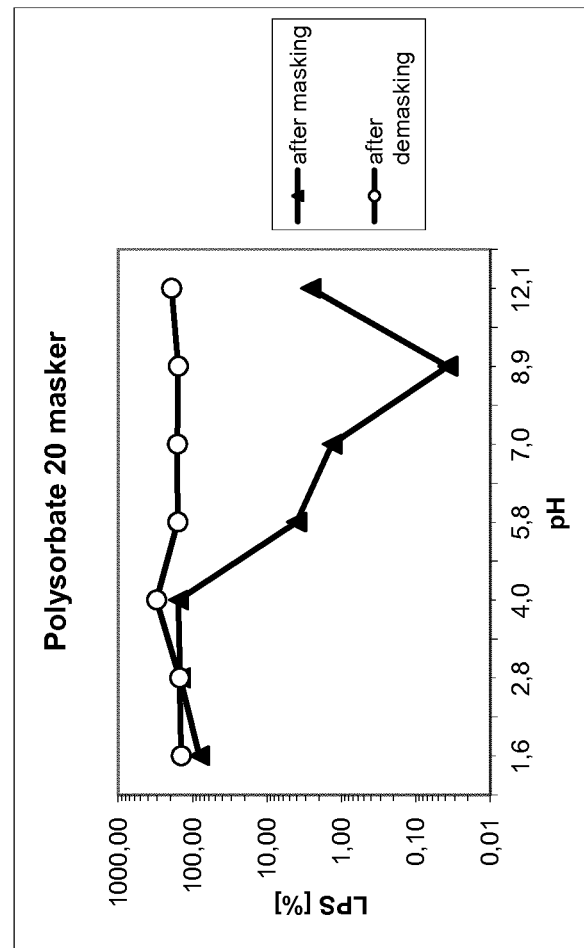
FIG. 10 is a graph showing the percent recovery of the endotoxin LPS from a masking detergent (polysorbate 20) as dependent on pH.
Figure 11:
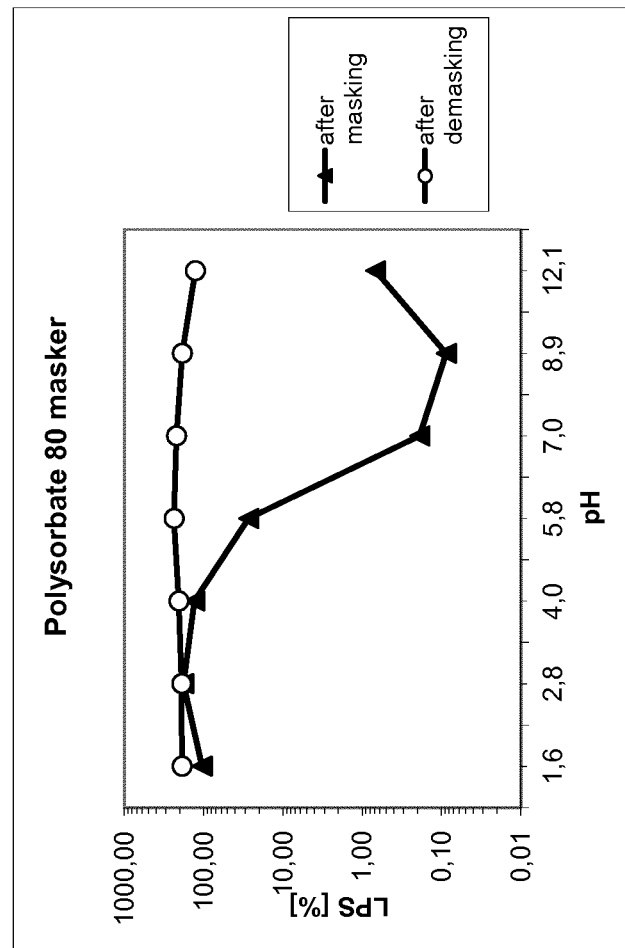
FIG. 11 is a graph showing the percent recovery of the endotoxin LPS from a masking detergent (polysorbate 80) as dependent on pH.

Table 12 (below) and FIGS. 10 and 11 show the percentage of LPS recovery after 7 days of masking as dependent on the pH-value and the percentage of LPS recovery after unmasking of the masked samples.

TABLE 12

| phosphate buffer (pH-value) | Polysorbate 20 masker | | Polysorbate 80 masker | |
|---|---|---|---|---|
| | recovery after masking [%] | recovery after unmasking [%] | recovery after masking [%] | recovery after unmasking [%] |
| 1.6 | 81 | 143 | 104 | 188 |
| 2.8 | 146 | 150 | 179 | 189 |
| 4.0 | 156 | 305 | 130 | 206 |
| 5.8 | 4 | 158 | 27 | 237 |
| 7.0 | 1 | 160 | 0 | 221 |
| 8.9 | 0 | 156 | 0 | 187 |
| 12.1 | 3 | 192 | 1 | 128 |

The data show that masking in phosphate buffer solutions containing detergent is strongly pH dependent. At pH values below 4, no masking occurs after one week of sample incubation. At pH values above 4 a strong masking effect is seen, resulting in detectable LPS recoveries less than 1%.

The data also show conclusively that the unmasking approach implemented renders the previously masked, undetectable LPS detectable. Independent of the pH-value and the extent of masking, 100% or more of LPS can be recovered, i.e. detected.

Example 12: Unmasking Using Other Displacing Modulators than SDS

As shown in the examples above, a combination of $CaCl_2$/BSA/SDS/1-doedecanol efficiently unmasked endotoxin which is masked by Triton X-100 detergent. Several of the experiments described above suggests the importance of including SDS in this scheme to achieve efficient unmasking. The aim of the experiments described in the present example is to investigate whether the modulator component SDS (here, as disrupting modulator) can be exchanged for another detergent without negatively impacting the unmasking effect observed using SDS.

Materials and Methods

Masking of endotoxin was performed as follows: 1 ml aliquots of 10 mM citrate pH 7.5 containing 0.05% Triton X-100 were prepared in endotoxin-free glass test tubes. Subsequently, 10 µl of a 10,000 EU/ml stock solution of LPS (LPS 055 B5, Sigma L2637-5MG) were added, vortexed for 1 min and stored at room temperature for at least 24 hours. A positive LPS control in water was prepared as follows: 10 µl of a 10,000 EU/ml LPS stock solution was added to 1 ml of endotoxin-free water, mixed and identically incubated as the masking preparations. Further details regarding the positive LPS-water control are indicated in Example 1.

Unmasking of endotoxin was performed as follows: To masked solutions of LPS, prepared as indicated above, $CaCl_2$, BSA, detergent X and 1-dodecanol were added as described in the previous examples, where "detergent X" (disrupting modulator) was varied in identity and concentration. The following detergents were tested: dioctyl sulfosuccinate sodium salt (AOT), sodium dodecyl benzene sulfonate (SDBS), polyethylene glycol 4-nonylphenyl-3-sulfopropyl ether potassium salt (PENS) and p-xylene-2-sulfonic acid hydrate (XSA). Unmasking was performed as described in above examples, endotoxin content was determined using the EndoLISA® kit of Hyglos GmbH, and the percentage of LPS recovery was calculated with reference to the LPS-water positive control. Further details regarding the LPS-water positive control are described in Example 1 above.

Results

Table 13 shows the percentage of LPS recovery after unmasking using detergents other than SDS in the $CaCl_2$/BSA/[detergent X]/1-dodecanol unmasking approach.

TABLE 13

| Detergent | Concentration optimum | LPS recovery [%] |
|---|---|---|
| AOT | 0.01% | 24 |
| SDBS | 0.01% | 34 |
| PENS | 0.10% | 23 |
| XSA | 0.05% | 26 |

The data show that other detergents besides SDS are able to support unmasking as a disrupting modulator in a $CaCl_2$/BSA/[detergent X]/1-dodecanol unmasking approach. Furthermore, in the absence of 1-dodecanol no detergent was able to unmask LPS from Triton X-100. As mentioned above, this suggests that 1-dodecanol may play an important role (at least) as a reconfiguring modulator which may be crucial for mediating the transition of endotoxin from a solubilized (undetectable) to an aggregated (detectable) state.

Example 13: Unmasking from Buffered Antibody Compositions as Dependent on the Masking Detergent The most commonly used formulations of protein-based drug products contain phosphate buffer and non-ionic detergents such as polysorbate 20 or polysorbate 80. Further, antibodies constitute one of the most commonly formulated pharmaceutical protein products. With this in mind, we sought to confirm whether the above unmasking approaches for detergents- or protein-masking systems are suitable for unmasking endotoxin in systems containing both detergent and protein, where the protein is an antibody buffered in phosphate. Polysorbate 20 and 80 were chosen as masking detergents in these experiments because these two detergents are the most commonly used detergents in protein drug formulations.

Materials and Methods

Endotoxin masking was performed as follows: 50 EU/ml of endotoxin (*E. coli* O55:B5; Sigma L2637-5MG) was added to 1 ml aliquots of an antibody solution containing 10 mg/ml of a bovine polyclonal IgG antibody preparation, dissolved in 10 mM sodium phosphate pH 7.5 and 50 mM NaCl. Subsequently, either polysorbate 20 or polysorbate 80 were added to a final concentration of 0.05%, and the solutions were incubated for 3 days at room temperature to allow masking to occur. Further, controls containing the buffer solution without detergent or antibody, as well as the buffer solution containing either the antibody or the respective polysorbate were prepared and treated like the masking samples. Each of the controls contained the same amount of LPS.

Unmasking was performed as follows: Unmasking was performed by addition of either 1-dodecanol or BSA/1-dodecanol or $CaCl_2$/BSA/SDS/1-dodecanol. 100 µl of the following stock solutions were added to 1 ml of sample solution: $CaCl_2$ (1 M), BSA (100 mg/ml), SDS (1%) and 1-dodecanol (100, 10 or 1 mM). Furthermore, before addition of calcium chloride to a sample, the sample was stabilized against calcium phosphate precipitation by the addition of a final concentration of 200 mM sodium citrate pH 7.5. All stock solutions were added sequentially with two-minute mixing steps following each addition. After addition and mixing of the last component the samples were incubated for at least 30 minutes at room temperature. Afterwards, the samples were diluted 1:10 and 1:100 in endotoxin-free water and analyzed for endotoxin content using the EndoLISA kit (Hyglos GmbH). The percentage of LPS recovery was calculated with reference to the determined endotoxin content in the buffer control (discussed in more detail in Example 1).

Results

Table 14a (below) shows the percentage of LPS recovery of the water control, the buffer without detergent, the buffer containing antibody or detergent and the buffer containing antibody and detergent after 3 days of incubation at room temperature.

TABLE 14a

| sample type | ingredients | polysorbate 20 LPS recovery (%) | polysorbate 80 LPS recovery (%) |
|---|---|---|---|
| water control | water | 100 | 100 |
| buffer | buffer without detergent | 102 | 99 |
| masking control | buffer + antibody | 31 | 44 |
| masking control | buffer + polysorbate | 0 | 2 |
| masking control | buffer + polysorbate + antibody | 0 | 9 |

Table 14b (below) shows the percentage of LPS recovery from an antibody solution after unmasking containing either polysorbate 20 or 80. Furthermore, it shows the concentrations of the added stock solutions.

TABLE 14b

| [CaCl2] (M) | [BSA] (mg/ml) | [SDS] (%) | [1-Dodecanol] (mM) | polysorbate 20 LPS recovery (%) | polysorbate 80 LPS recovery (%) |
|---|---|---|---|---|---|
| — | — | — | 100 | 16.6 | 9.1 |
| — | — | — | 10 | 19.9 | 6.8 |
| — | — | — | 1 | 0.0 | 5.0 |
| — | 100 | — | 100 | 40.8 | 11.2 |
| — | 100 | — | 10 | 2.6 | 6.3 |
| — | 100 | — | 1 | 1.6 | 11.5 |
| 1 | 100 | 1 | 100 | 4.8 | 3.0 |
| 1 | 100 | 1 | 10 | 15.9 | 23.1 |
| 1 | 100 | 1 | 1 | 67.3 | 90.8 |

The data show that the buffer solutions without polysorbate 20 or 80 do not mask the added LPS. The buffer solutions containing antibody but no polysorbate mask ~55% to 70% of the LPS, suggesting that the antibody protein contributes a masking effect of its own. The LPS recoveries from buffer solutions containing polysorbate or polysorbate and antibody are below 10% when no unmasking measures are taken. Thus, not only the detergent but also the antibody is responsible for masking of LPS.

LPS recoveries after unmasking from the masking complexes containing LPS, detergent and antibody are low using 1-dodecanol alone (9 and 17% for polysorbate 80 and 20, respectively). Using a combination of BSA (adsorbing modulator) and 1-dodecanol (disrupting and reconfiguring modulator) allowed moderate LPS recoveries of 11 and 41% for polysorbate 80 and 20, respectively. Unmasking using a combination of $CaCl_2$, BSA (adsorbing modulator), SDS (displacing modulator) and 1-dodecanol (disrupting and reconfiguring modulator), results in recoveries of 67% and 91% of the masked LPS for polysorbate 20 and 80, respectively. Interestingly, unmasking was achieved using a 1-dodecanol stock solution with a concentration as low as 1 mM. Furthermore, in contrast to the unmasking from detergent systems lacking protein, using 1-dodecanol (disrupting and reconfiguring modulator) or BSA (adsorbing modulator) and 1-dodecanol (disrupting and reconfiguring modulator) do not unmask with greater efficiency than 50%. As shown for lysozyme above, efficient unmasking was only be achieved in the presence of $CaCl_2$, BSA, SDS and 1-dodecanol.

Example 14: Unmasking from Compositions Containing Antibody and Polysorbate 20 as Dependent on the Buffer Substance It was determined in above Example 14 that the inventive unmasking approaches described herein are suitable for unmasking compositions which contain both detergent and buffered protein (antibody). In view of this, it was then desired to investigate the influence of buffer on unmasking efficiency. To this end, we chose 10 mM citrate or 10 mM phosphate buffer of pH 7.5, because these are the most commonly used buffers in protein drug formulations.

Materials and Methods

Endotoxin masking was performed as follows: 50 EU/ml of endotoxin (*E. coli* O55:B5; Sigma L2637-5MG) were added to 1 ml aliquots of an antibody solution containing 10 mg/ml of a bovine polyclonal IgG antibody preparation, dissolved in either 10 mM sodium phosphate containing 50 mM sodium chloride or 10 mM sodium citrate pH 7.5 containing 150 mM sodium chloride. Subsequently, polysorbate 20 was added to a final concentration of 0.05% and samples were masked for 3 days at room temperature. Further, positive controls containing the buffer solution without detergent or antibody, as well as the buffer solution containing either the antibody or the respective polysorbate were prepared and treated like the masking samples. Each of the positive controls contained the same amount of LPS.

Endotoxin unmasking was performed as follows: Unmasking was performed by addition of either 1-dodecanol or a combination of BSA (adsorbing modulator) and 1-dodecanol (disrupting and reconfiguring modulator) or $CaCl_2$, BSA (adsorbing modulator), SDS (displacing modulator) and 1-dodecanol (disrupting and reconfiguring modulator). 100 µl of each of the following stock solutions were sequentially added to 1 ml of sample solution: $CaCl_2$ (1 M), BSA (10 mg/ml), SDS (1%) and 1-dodecanol (100, 10 or 1 mM). Furthermore, before addition of calcium chloride to a phosphate buffer-containing sample, this sample was stabilized against calcium phosphate precipitation by the addition of a final concentration of 200 mM sodium citrate pH 7.5. All stock solutions were added sequentially with two-minute mixing steps after each addition. After addition and mixing of the last component the samples were incubated for at least 30 minutes at room temperature. Afterwards, the samples were diluted 1:10 and 1:100 in endotoxin-free water and analyzed for endotoxin content using the EndoLISA kit (Hyglos GmbH). The percentage of LPS recovery was calculated with reference to the determined endotoxin content in the positive control (discussed in more detail in Example 1).

Results

Table 15 (below) shows the percentage of LPS recovery from an antibody solution after masking and unmasking containing either citrate or phosphate as buffer substance.

TABLE 15

| sample type | ingredient | citrate buffer LPS recovery (%) | phosphate buffer LPS recovery (%) |
|---|---|---|---|
| water control | water | 100 | 100 |
| masking control | buffer + antibody | 40 | 31 |
| masking control | buffer + polysorbate 20 | 0 | 0 |
| masking control | buffer + polysorbate 20 + antibody | 1 | 0 |

| sample type | unmasking approach/ ingredients | LPS recovery (%) | [1-dodecanol] (mM) | LPS recovery (%) | [1-dodecanol] (mM) |
|---|---|---|---|---|---|
| unmasked sample * | 1-dodecanol | 26 | 100 | 17 | 100 |
| unmasked sample * | BSA/ 1-dodecanol | 49 | 100 | 41 | 100 |
| unmasked sample * | $CaCl_2$/ BSA/SDS/ 1-dodecanol | 87 | 100 | 67 | 1 |

* "Unmasked" samples contained antibody.

The data show that the buffer solutions containing antibody but no polysorbate, mask 60% to 70% of the LPS (based on the recovery of 40% and about 30% LPS for citrate and phosphate buffers, respectively). The LPS recoveries from buffer solutions containing polysorbate or polysorbate and antibody are below 1%. In these cases, masking is independent of the buffer present.

LPS recoveries after unmasking from the compositions containing LPS, detergent and antibody are low using 1-dodecanol alone (17% and 26% for phosphate and citrate, respectively) and moderate using a combination of BSA (adsorbing modulator) and 1-dodecanol (disrupting and reconfiguring modulator) (41% and 49% for phosphate and citrate, respectively). Unmasking using a combination of $CaCl_2$, BSA (adsorbing modulator), SDS (displacing modulator and 1-dodecanol (disrupting and reconfiguring modulator) results in recoveries of 67% and 87% of the masked LPS for phosphate and citrate, respectively. Interestingly, the necessary concentration of 1-dodecanol stock solution for efficient unmasking differs strongly between the buffer systems used (100 mM for antibody/detergent/citrate and 1 mM for antibody/detergent/phosphate). The data clearly show that efficient unmasking of endotoxin in compositions comprising both protein (antibody) and detergent can be achieved by adjustment of 1-dodecanol concentration.

Example 15: Masking and Unmasking of an Antibody Solution Containing LPS from Unknown Source To show that unmasking is not only possible from solutions containing LPS from a known source, we tested a commercially available mouse monoclonal antibody for diagnostic use which contains an LPS contamination, where the source of the LPS is unknown. Furthermore, this antibody was dissolved in a buffer composition which corresponds to the formulation of the known antibody drug product Rituximab (MabThera®, Rituxan®).

Materials and Methods

Determination of endotoxin contamination: A mouse monoclonal antibody (MAB 33, Roche Diagnostics) was dissolved in a solution containing citrate and sodium chloride of pH 6.5 and stored at 4° C. The final concentrations of citrate, sodium chloride and antibody were 25 mM, 150 mM and 10 mg/ml, respectively. Directly after solubilization of the antibody, the endotoxin content was analyzed using EndoZyme® and EndoLISA® detection kits (Hyglos GmbH). The determined endotoxin content was 11 EU/mg of antibody.

LPS masking was initiated by addition of polysorbate 80 to a final concentration of 0.07% and increasing the temperature to ambient conditions (22° C.). Afterwards, 1 ml aliquots of the samples were incubated at room temperature for 3 days to allow the endotoxin present to become masked.

Unmasking was performed as follows: Unmasking was performed by addition of either 1-dodecanol (disrupting and reconfiguring modulator); or a combination of BSA (adsorbing modulator) and 1-dodecanol (disrupting and reconfiguring modulator); or a combination of $CaCl_2$, BSA (adsorbing modulator), SDS (displacing modulator) and 1-dodecanol (disrupting and reconfiguring modulator). 100 μl of each of the following stock solutions were sequentially added to 1 ml of sample solution: $CaCl_2$ (1 M), BSA (10 mg/ml), SDS (1%) and 1-dodecanol (100, 10 or 1 mM). All stock solutions were added sequentially with two-minute mixing steps after each addition. After addition and mixing of the last component the samples were incubated for at least 30 minutes at room temperature.

Afterwards, the samples were diluted 1:10 and 1:100 in endotoxin free water and analyzed for endotoxin content using EndoLISA® (Hyglos GmbH). The percentage of LPS recovery was calculated in reference to the determined endotoxin content at time zero.

Results

Table 16 (below) shows the percentage of endotoxin recovery as dependent on the masking time, the presence or absence of polysorbate 80 and unmasking from antibody/polysorbate 80 solution.

TABLE 16

| sample type | ingredients | LPS recovery (%) | |
|---|---|---|---|
| control t(0) | buffer + antibody | 100 | |
| masking control (3 days) | buffer + antibody | 57 | |
| masking control (3 days) | buffer + polysorbate 80 | 0 | |
| masking control (3 days) | buffer + polysorbate 80 + antibody | 3 | |
| sample type | unmasking approach/ ingredients | LPS recovery (%) | [1-dodecanol] (mM) |
| unmasked sample * | 1-dodecanol | 45 | 100 |
| unmasked sample * | BSA/1-dodecanol | 68 | 100 |

* "Unmasked" samples contained antibody.

The data show that the buffer solution containing antibody but no polysorbate masks 40% of the LPS within 3 days of incubation at room temperature. However, incubation in buffer containing either polysorbate 80 or antibody and polysorbate 80, results in endotoxin recoveries smaller than 4%.

Unmasking from the antibody/detergent samples results in recoveries of 45% using 1-dodecanol (disrupting and reconfiguring modulator); 68% using a combination of BSA (adsorbing modulator) and 1-dodecanol (disrupting and reconfiguring modulator); and 179% using a combination of $CaCl_2$, BSA (adsorbing modulator), SDS (displacing modulator) and 1-dodecanol (disrupting and reconfiguring modulator). In the latter case, the best recovery is achieved using a 1 mM 1-dodecanol stock solution.

The experiments described in this example show that, when present, naturally occurring endotoxin (NOE) can be detected by a suitable endotoxin detection system. Furthermore, these experiments show that such NOE can be masked in the manner described herein above, i.e. the danger of masking applies not only for purified endotoxin, but also for NOE. The ability of the inventive methods as described herein to unmask such NOE further demonstrate their applicability to situations in which NOE has been masked, proving their effectiveness of the inventive methods to unmask masked NOE. These findings are relevant to the conditions prevailing in industry, where production processes often start with an expressed protein in the presence of NOE, and the latter is masked by incorporation of detergent to prevent unwanted protein aggregation. Overall, then, the results of the experiments described in this example demonstrate that the inventive methods are able to unmask endotoxin under conditions of relevance for the pharmaceutical industry.

These data also clearly show that unmasking is independent of the source and purity of the LPS.

In all three cases of masking in antibody solutions (Examples 13, 14 and 15), it can be seen that masking is not only due to the detergent component in the composition but also to some extent to the antibody itself. The most efficient unmasking approach is to use a combination of $CaCl_2$, BSA (adsorbing modulator), SDS (displacing modulator) and 1-dodecanol (disrupting and reconfiguring modulator) to unmask the endotoxin. Here, analogies can be seen to the lysozyme case (discussed in Example 7 above), in which the protein itself plays a role as an endotoxin masker. Interestingly, in all cases, the concentration of 1-dodecanol should be optimized for efficient unmasking.

Example 16: General Evaluation of Unmasking Approach as Applied to a New Composition in Question As shown in the above examples, the choice of the approach taken to unmask endotoxin suspected of being present, but masked in a composition will depend on a number of factors. For instance, as the foregoing examples have shown, it is sometimes possible to achieve efficient unmasking using a single-component modulator which doubles as a disrupting modulator and a reconfiguring modulator, as defined herein above. On the other hand, in some instances, the modulator should be a modulator system with two or more components, for instance a displacing modulator and/or an adsorbing modulator, depending on what measures are needed to destabilize and disrupt the endotoxin/endotoxin masker complex sufficiently such that the endotoxin is liberated and can be mediated into an aggregated form which can be detected.

The above examples start from known, controlled solution conditions in order to illustrate concepts underlying the present invention. In a real-world scenario, however, in which the methods of the invention are to be applied to a new composition in question, it is necessary to first evaluate the approach of the methods of the invention before meaningful results can be obtained. The present example addresses such a validation, setting out a generic scheme by which the methods of the invention may be calibrated to a new composition in question. To this end, an iterative unmasking approach is necessary, starting with an initial screening for the best suited unmasking approach followed by subsequent improvement steps for adjustment of optimum unmasking component concentrations.

General Description of an Evaluation Process for a Given Composition

Figure 12:
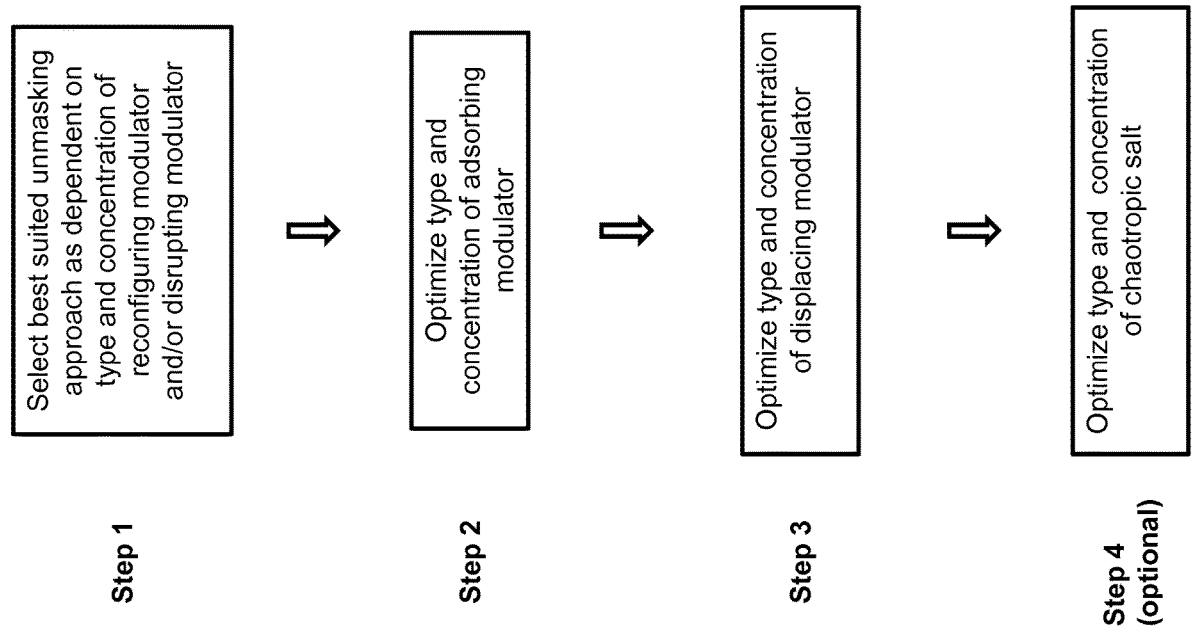
FIG. 12 is a flowchart showing a generalized validation scheme for determining and optimizing an unmasking process for a composition in question suspected of containing masked endotoxin.

Generally, FIG. 12 shows a scheme which schematically sets out the steps which one would normally take in evaluating the inventive methods for a new, unknown composition.

As will be clear from the above, ultimate detection of initially masked endotoxin depends on the ability to convert this endotoxin from stably bound (masked) form to an aggregated from which is unmasked and therefore detectable. The component of the modulator responsible for this final conversion is the reconfiguring modulator. The first step of FIG. 12 reflects this, in that it specifies a first step of determining an optimal concentration of reconfiguring modulator (e.g. 1-dodecanol). Step 2 then optimizes the concentration of adsorbing modulator, if this modulator is included. Step 3 then optimizes the concentration of displacing modulator, if this modulator is included.

It should be emphasized that not all three steps will always be needed. If one already sees that a composition, for example a pharmaceutical composition, in question contains significant amounts of endotoxin following step one, then this answer may already be enough to conclude that the composition thought to be endotoxin-free was really not.

Specific Description of Evaluation Process for a Given Composition

Figure 13:
FIG. 13 is a table showing a generalized evaluation scheme for determining and optimizing an unmasking process for a composition in question suspected of containing masked endotoxin.
Figure 13:
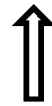
Figure 14:
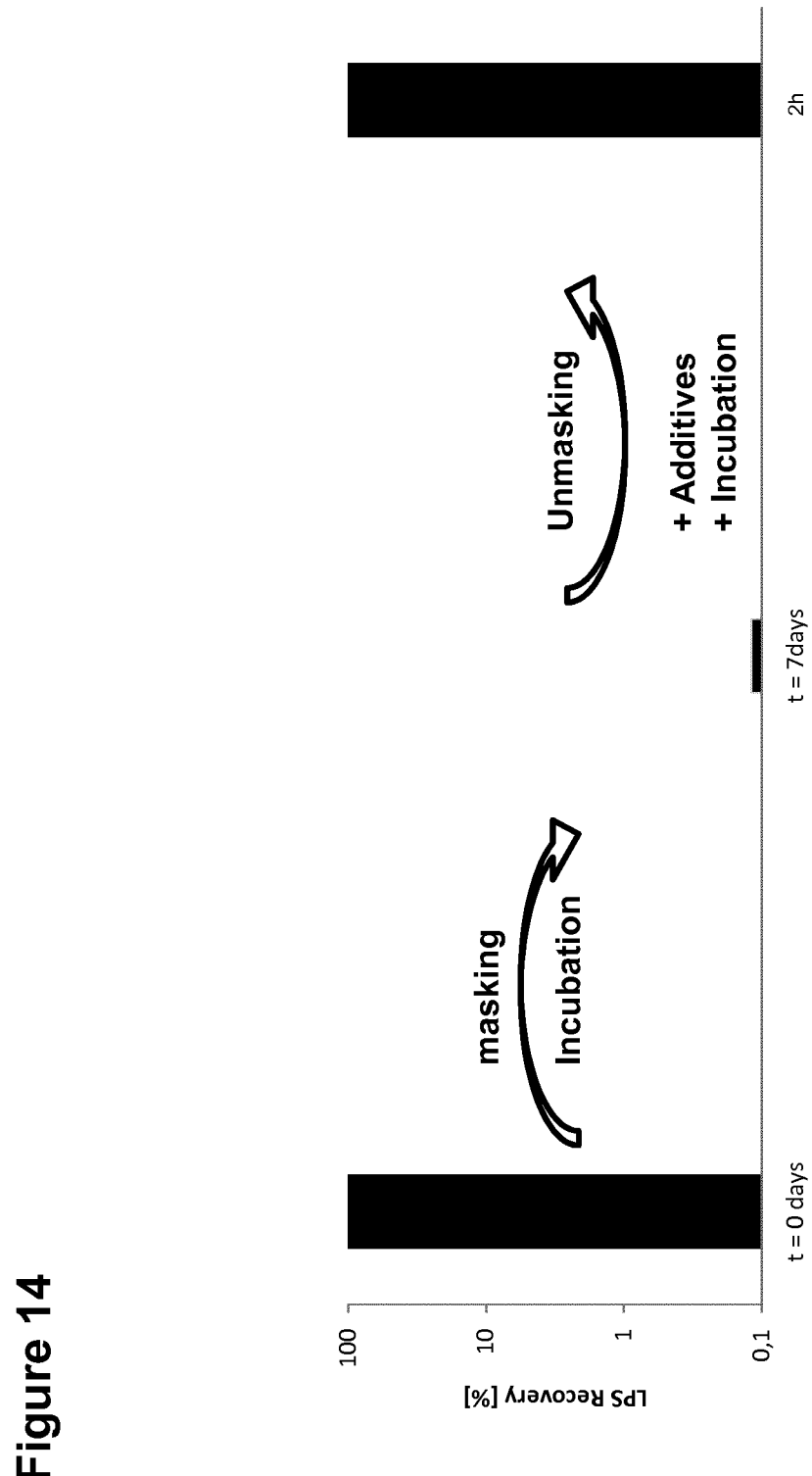
FIG. 14 is a general schematic representation of the inventive methods herein, as viewed from the standpoint of the level of LPS recovery (i.e. measured LPS activity) before and after masking (left and middle bars of figure, respectively), as well as after unmasking according to the methods of the present invention (right bar of figure). The left and middle bars of the figure thus represent the circumstances commonly prevailing in pharmaceutical formulations, in which endotoxin which is present in solution, is rendered undetectable by one or more endotoxin maskers. This endotoxin can be again rendered detectable, i.e. can be "rescued" out of its masked state, by the methods of the present invention, enabling one to detect the previously masked endotoxin.
Figure 15:
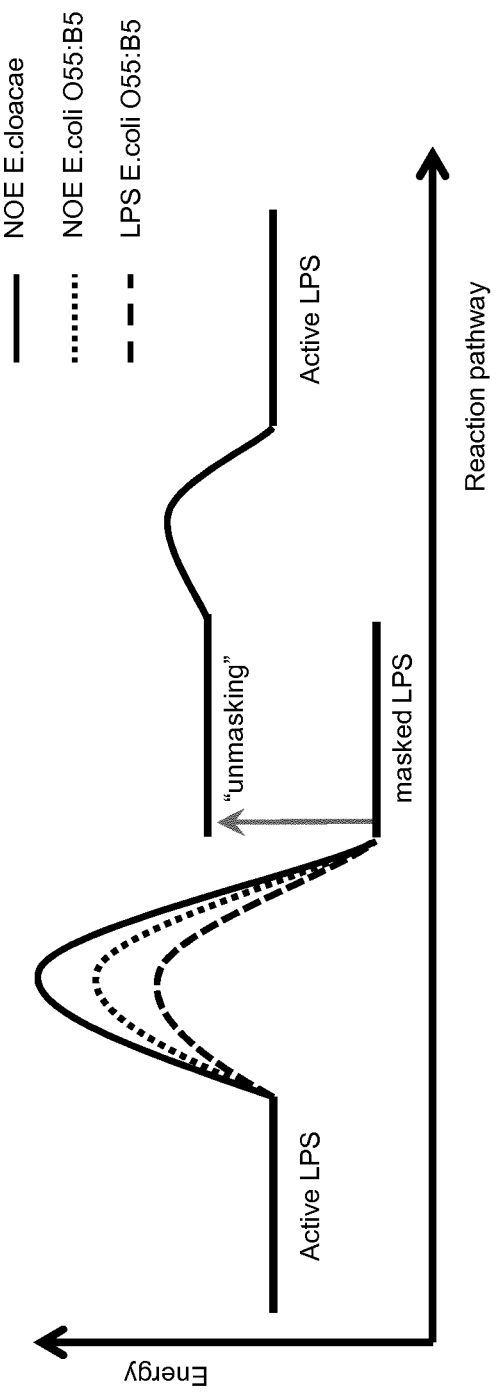
FIG. 15 shows a generic diagram illustrating the dynamics associated with the unmasking methods described herein. The transition from active (i.e. aggregated and therefore detectable) LPS at the far left to masked LPS (middle bottom; non-aggregated) is shown for several representative endotoxins. Because the energy associated with the "masked LPS" is lower than that associated with "active LPS", the LPS remains stabilized in this masked form. The inventive methods described herein effectively destabilize this masked LPS, thus raising its energy to a level above that of masked LPS, from where LPS can again fall back down in energy into aggregated form (far right of diagram). It as assumed that the reconfiguring modulator plays a key role in mediating this rescue of LPS from solubilized (masked) to aggregate (unmasked) form.

FIG. 13 shows the combinations and concentrations of stock solutions for selecting and optimizing the unmasking process. The unmasking approaches are divided into different possible scenarios A, B and C, depending on which substance or combination of substances is/are used in unmasking. Unmasking approach A describes an unmasking approach in which only 1-dodecanol is used as a modulator. Unmasking approach B describes an unmasking approach in which the modulator system is composed of 1-dodecanol and BSA. Unmasking approach C describes an unmasking approach in which the modulator system is composed of 1-dodecanol, BSA and SDS, and is performed in the presence of $CaCl_2$.

Procedure

Add 100 µl of the unmasking component stock solutions to 1 ml of masked sample. After addition of one component, mix sample thoroughly by vortexing for 2 minutes. Then, add the next component and mix. After addition of all components and subsequent mixing, incubate samples for >30 minutes at room temperature. Afterwards, analyze samples for endotoxin content using an appropriate endotoxin testing method, e.g. the EndoLISA® kit of Hyglos GmbH.

Example 17: Detection of Unmasked Endotoxin Using a Recombinant Factor C Assay

This experiment investigates the effect of unmasking endotoxin using a multi-component modulator comprising $CaCl_2$, BSA, SDS and dodecanol. Endotoxin content of the masked and unmasked samples was determined using the EndoZyme® kit of Hyglos GmbH. The experiment was performed in order to show that detection of unmasked endotoxin can be achieved using different detection assays.

Materials and Methods

Endotoxin (E. coli O55:B5, Sigma L2637-5MG) was masked in solutions containing 1×PBS-buffered 0.05 wt % Polysorbate 80 or 1×PBS buffered 0.05 wt % Polysorbate 20 for 3 days at room temperature.

Unmasking was performed as follows: Unmasking was performed by a combination of sodium citrate, $CaCl_2$, BSA, SDS and 1-dodecanol. 150 µL of sodium citrate and 100 µl of each of the following stock solutions were added to 1 ml of sample solution: sodium citrate (1.375 M pH 7.5), $CaCl_2$ (1 M), BSA (10 mg/ml), SDS (1%) and 1-dodecanol (1 mM). 1-dodecanol was solubilized in 70% EtOH. In a separate masking control, no unmasking was performed.

All stock solutions were added sequentially with two-minute mixing steps after each addition. After addition and mixing of the last component the samples were incubated for at least 30 minutes at room temperature.

Subsequently, masked (masking control) and unmasked samples were diluted stepwise 1:10 and 1:5 in depyrogenated water (final dilution 1:50). A recombinant Factor C assay (EndoZyme®) was used for detection of endotoxin.

Results

Table 17 (below) shows the percent recovery, measured using a recombinant Factor C assay (EndoZyme®), of endotoxin recovered from the two masking systems specified above in this example.

TABLE 17

Detection of unmasked endotoxin using recombinant Factor C

| | Recombinant Factor C | |
| --- | --- | --- |
| Sample | PBS + P80 [EU/mL] | PBS + P20 [EU/mL] |
| Positive control | 9.3 | 6.8 |
| | Recovery [%] | Recovery [%] |
| Masking control | 0 | 0 |
| After unmasking | 65 | 66 |

The masking control showed no endotoxin recovery in either sample. Unmasking of endotoxin in polysorbate 80 or polysorbate 20 resulted in endotoxin recovery of 65% and 66%, respectively, with reference to the positive control (endotoxin content in depyrogenated water). The results indicate the efficient demasking of endotoxin using a multi-component modulator comprising Sodium citrate, $CaCl_2$, BSA, SDS and dodecanol as detected by a recombinant Factor C detection system (EndoZyme®). This experiment proves that the detection of unmasked endotoxin is independent of the endotoxin detection system used. Accordingly, unmasked endotoxin may be detected using the endotoxin detection system employed in previous examples, but may also be detected using an endotoxin detection system differing from that used in previous examples.

Example 18: Detection of Unmasked Endotoxin Using a Limulus Ameboecyte Lysate (LAL) Assay This experiment investigates the detection of unmasked endotoxin using a detection assay different from the recombinant Factor C assay (EndoZyme®), i.e. the Limulus Ameboecyte Lysate (LAL) assay. The experiment was performed in order to further corroborate that detection of endoxin unmasking does not depend on the detection assay.

Materials and Methods

Endotoxin (*E. coli* O55:B5, Sigma L2637-5MG). was masked in solutions containing 1×PBS-buffered 0.05 wt % Polysorbate 80 or 1×PBS buffered 0.05 wt % Polysorbate 20 for 3 days at room temperature.

Unmasking was performed as follows: Unmasking was performed by a combination of sodium citrate, $CaCl_2$, BSA, SDS and 1-dodecanol. 150 μL of sodium citrate and 100 μl of each of the following stock solutions were added to 1 ml of sample solution: sodium citrate (1.375 M pH 7.5), $CaCl_2$ (1 M), BSA (10 mg/ml), SDS (1%) and 1-dodecanol (1 mM). 1-dodecanol was solubilized in 70% EtOH.

All stock solutions were added sequentially with two-minute mixing steps after each addition. After addition and mixing of the last component the samples were incubated for at least 30 minutes at room temperature.

Subsequently, masked (masking control) and unmasked samples were diluted stepwise 1:10 and 1:5 in depyrogenated water (final dilution 1:50). A kinetic LAL-based chromogenic assay (kinetic-QCL®, Lonza) was used for detection of endotoxin. Masking control reflects the detectable endotoxin content without unmasking. In a separate masking control, no unmasking was performed. Results Table 18 (below) shows the percent recovery, measured using an LAL assay (kinetic QCL®, Lonza), of endotoxin recovered from the two masking systems specified above in this example.

TABLE 18

Unmasking using an LAL assay

| Sample | LAL | |
|---|---|---|
| | PBS + P80 [EU/mL] | PBS + P20 [EU/mL] |
| Positive control | 11.6 | 7.2 |
| | Recovery [%] | Recovery [%] |
| Masking control | 3 | 0 |
| After unmasking | 96 | 47 |

The masking control showed no endotoxin recovery in both samples. Unmasking of endotoxin in polysorbate 80 or polysorbate 20 resulted in endotoxin recovery of 96% and 47%, respectively, with reference to the positive control (endotoxin content in depyrogenated water). The data clearly demonstrate that unmasking of endotoxin can be detected with the LAL detection assay and that detection of endotoxin unmasking does not depend on the detection assay.

Example 19: Variation of Alkanols (Aliphatic Alcohols) as Modulators for Unmasking Using a Multi-Component Modulator This experiment investigates unmasking of different endotoxins using different alkanols. The experiment was performed in order to investigate the unmasking efficiency of different alkanol compounds in the multi-component modulator.

Materials and Methods

Endotoxin from *E. coli* O55:B5 (Sigma L2637-5MG), *S. abortus* equi (Acila 1220302) and *K. pneumoniae* (LMU) were masked in solutions containing 10 mM sodium citrate and 0.05 wt % Polysorbate 20 for three days at room temperature.

Unmasking was performed as follows: Unmasking was performed by a combination of NaCitrate, $CaCl_2$, BSA, SDS and 1-dodecanol. 150 μL of sodium citrate and 100 μl of each of the following stock solutions were added to 1 ml of sample solution: sodium citrate (1.375 M pH 7.5), $CaCl_2$ (1 M), BSA (10 mg/ml), SDS (1%) and a certain concentration of 1-dodecanol. The alkanols and alkanol mixtures used in the multi-component modulator systems were solubilized in EtOH; concentrations are listed in Table 19a (below). In a separate masking control, no unmasking was performed.

All stock solutions were added sequentially with two-minute mixing steps after each addition. After addition and mixing of the last component the samples were incubated for at least 30 minutes at room temperature.

TABLE 19a

| Unmasking approach: | Alkanols (size) | Concentration [mM] |
|---|---|---|
| 1 | Octanol (C8) | 1.0 |
| 2 | Decanol (C10) | 1.0 |
| 3 | Dodecanol (C12) | 1.0 |
| 4 | Tetradecanol (C14) | 1.0 |
| 5 | Hexadecanol (C16) | 1.0 |
| 6 | Octanol (C8) | 0.3 |
|   | Decanol (C10) | 0.3 |
|   | Dodecanol (C12) | 0.3 |
| 7 | Decanol (C10) | 0.3 |
|   | Dodecanol (C12) | 0.3 |
|   | Tetradecanol (C14) | 0.3 |
| 8 | Dodecanol (C12) | 0.3 |
|   | Tetradecanol (C14) | 0.3 |
|   | Hexadecanol (C16) | 0.3 |

Afterwards, the samples were diluted 1:10 and 1:100 in endotoxin free water and analyzed for endotoxin content using EndoLISA® (Hyglos GmbH). The percentage of LPS recovery was calculated in reference to the determined endotoxin content at time zero (summarized in Table 19b, below).

Results

Table 19b (below) shows the percent recovery after masking (masking control) and after unmasking using the EndoLISA® assay (Hyglos) from the above masking system by various unmasking approaches employing different alkanols (aliphatic alcohols) or alkanol mixtures (aliphatic alcohol mixtures) as specified above in Table 19a.

TABLE 19b

Unmasking of different endotoxins using Ca, BSA, SDS and varying alkanols, as detected by the EndoLISA ® assay

| | Endotoxin | | |
|---|---|---|---|
| | K. pneumoniae * [EU/mL] | S. abortus equi [EU/mL] | E. coli O55:B5 [EU/mL] |
| Positive Control | 191 | 51 | 68 |
| | Recovery [%] | Recovery [%] | Recovery [%] |
| Masking Control | 0 | 0 | 0 |
| Unmasking approach (alkanol size) | | | |
| 1 (C8) | 75 | 0 | 2 |
| 2 (C10) | 52 | 0 | 0 |
| 3 (C12) | 147 | 62 | 76 |
| 4 (C14) | 94 | 108 | 71 |
| 5 (C16) | 99 | 83 | 22 |
| 6 (C8, C10, C12) | 60 | 14 | 6 |
| 7 (C10, C12, C14) | 126 | 108 | 43 |
| 8 (C12, C14, C16) | 126 | 173 | 43 |

* For unmasking of K. pneumoniae 150 µL of $CaCl_2$ were added.

The above results indicate that unmasking of K. pneumoniae was achieved with octanol (75% recovery), dodecanol (147%), tetradecanol (94%) and hexadecanol (99%), as well as with different combinations of alkanols (see e.g. unmasking approaches 7 and 8). Unmasking with decanol, however, was less efficient (52%). Unmasking of the S. abortus equi LPS was most efficient using tetradecanol (108%), hexadecanol (82%), dodecanol (62%), or different combinations of alkanols. Effective unmasking of E. coli O55:B5 was observed for dodecanol (76%) and tetradodecanol (71%). No endotoxin recovery was observed for the masking controls.

These results indicate that the most efficient unmasking (independent of the nature of the endotoxin) was achieved using dodecanol or tetradecanol, or using combinations of dodecanol and tetradecanol with a further alkanol (e.g. decanol in demasking 7). These results also indicate that all multi-component modulator systems with $C_{12}$, $C_{14}$ and/or $C_{16}$ aliphatic alcohols exhibited efficient unmasking of endotoxin.

The range of alkyl chain length of the fatty alcohols for efficient unmasking seems to depend on the endotoxin source. The differences in the unmasking efficiencies may depend to a certain extent on the heterogeneity in length of the acyl chains of the β-hydroxy-fatty acids which are present in the Lipid A portion of endotoxin. Between and within bacterial species, these acyl chains can vary in length from C10 to C28 (Endotoxin in health and disease, edited by H. Brade (1999), p98 et seq: "Chemical structure of Lipid A: Recent advances in structural analysis of biologically active molecules"; Marcel Dekker Inc, New York). However, most commonly β-hydroxy-fatty acids with chains length of C14 and C16 are appended to the diglucosamine of Lipid A. Thus, unmasking is in all cases most efficient in the presence of fatty alcohols with alkyl chain length between C12 and C14, although unmasking of endotoxin is also observed for other alkyl chain lengths in the C8-C16 range.

Example 20: Variation of Alkanols (Aliphatic Alcohols) as Modulators for Unmasking Using a Single-Component Modulator This experiment was performed to investigate the effect of various alkanols (aliphatic alcohols) on unmasking in the absence of additional modulator components. The experiment thus investigates the efficiency of endotoxin unmasking using various alkanols (aliphatic alcohols) as single-component modulators.

Materials and Methods

Endotoxin E. coli O55:B5 (Sigma L2637-5MG) was masked in solutions containing 10 mM sodium citrate and 0.05 wt % Polysorbate 20 for 3 days at room temperature.

In order to unmask the samples, samples (1 mL) were mixed with 100 µL of the particular alkanol (i.e. aliphatic alcohol). The alkanols used in the single-component modulator systems were solubilized in EtOH. Concentrations are shown in Table 20a (below).

TABLE 20a

Variation of alkanols (aliphatic alcohols)

| Unmasking Approach | Alkanols (size) | Concentration [mM] |
|---|---|---|
| 1 | Dodecanol (C12) | 50 mM |
| 2 | Tridecanol (C13) | 50 mM |
| 3 | Tetradecanol (C14) | 50 mM |

After addition of unmasking agents, the samples were incubated for 30 minutes and diluted 1:10 as well as 1:100 in depyrogenated water. Endotoxin was detected in both dilutions and the stated recovery reflects the mean recovery of both dilutions. The masking control reflects the non-treated sample after masking, i.e. the solution is not unmasked. The EndoLISA® assay was used for endotoxin detection.

Results

Table 20b (below) shows the percent recovery, measured using the EndoLISA® assay (Hyglos), of endotoxin recovered from the above masking system by various unmasking approaches employing different alkanols (aliphatic alcohols) in different unmasking approaches using single-modulator systems as specified above in Table 20a.

TABLE 20b

Unmasking using different alkanols (EndoLISA ®)

| Endotoxin | E. coli O55:B5 (gel) [EU/mL] |
|---|---|
| Positive Control | 111 |
| | Recovery [%] |
| Masking Control | 0 |
| Unmasking approach (alkanol size) | |
| 1 (C12) | 56 |
| 2 (C13) | 41 |
| 3 (C14) | 22.6 |

The results indicate that a single-component modulator consisting of dodecanol (unmasking approach 1) was most efficient in unmasking of E. coli O55:B5 (56% recovery), whereas single-component modulators consisting of tridecanol (unmasking approach 2) or tetradecanol (unmasking approach 3) resulted in less recovery of *E. coli* O55:B5 (41% and 22.6%, respectively). As expected, the masking controls showed no endotoxin recovery. In summary, the data demonstrate that the most efficient alkanol (aliphatic alcohol) for unmasking of *E. coli* O55:B5, when used as a single-component modulator system, is dodecanol, followed by tridecanol and tetradecanol.

The invention claimed is:

1. A method of unmasking an endotoxin in a composition, the composition comprising a protein active pharmaceutical ingredient (a protein API) and said endotoxin, said method comprising unmasking the endotoxin by adding to said composition a saturated unbranched 1-alkanol comprising 8 to 16 carbon atoms, a divalent cation that is Ca2+, sodium dodecyl sulfate (SDS) and an albumin,
   said protein API being selected from the group consisting of an antibody, an antibody fragment, a hormone, an enzyme, a fusion protein, and a protein conjugate.

2. The method of claim 1, further comprising detecting said endotoxin.

3. The method according to claim 1, further comprising the step of adding to said composition an agent which influences hydrogen bonding stability in solution.

4. The method according to claim 3, wherein said agent which influences hydrogen bonding stability in solution is added to said solution prior to the addition of said saturated unbranched 1-alkanol comprising 8 to 16 carbon atoms.

5. The method of claim 3, wherein the agent which influences hydrogen bonding stability in solution is a chaotropic agent, a cation or a combination thereof.

6. The method of claim 5, wherein said chaotropic agent is chosen from the group consisting of: urea; guanidinium chloride; butanol; ethanol; lithium perchlorate; lithium acetate; magnesium chloride; phenol; propanol; and thiourea.

7. The method of claim 1, wherein said saturated unbranched 1-alkanol is 1-dodecanol.

8. The method of claim 1, wherein said albumin is human serum albumin, bovine serum albumin and/or ovalbumin.

9. The method of claim 1, wherein the protein is an antibody fragment selected from the group consisting of a Fab; a Fab'; a F(ab')2; an Fv; a single chain antibody; and any combination thereof.

10. The method of claim 1, wherein the protein is an antibody selected from the group consisting of a fully human antibody; an anti-idiotype antibody; a humanized antibody; a bispecific antibody; a chimeric antibody; a CDR-grafted antibody; a monoclonal antibody; a polyclonal antibody; and any combination thereof.

11. The method of claim 1, wherein the composition is a pharmaceutical composition.

12. A method of detecting an endotoxin in a composition, the composition comprising a protein active pharmaceutical ingredient (a protein API) and said endotoxin,
    said method comprising the steps of:
    a) adding to said composition a saturated unbranched 1-alkanol comprising 8 to 16 carbon atoms, a divalent cation that is Ca2+, sodium dodecyl sulfate (SDS) and an albumin; and
    (b) detecting said endotoxin by means of a detection method,
    said protein API being selected from the group consisting of an antibody, an antibody fragment, a hormone, an enzyme, a fusion protein, and a protein conjugate.

* * * * *